(12) United States Patent
Banai et al.

(10) Patent No.: US 12,036,117 B2
(45) Date of Patent: Jul. 16, 2024

(54) PROSTHETIC VALVE WITH NATURAL BLOOD FLOW

(71) Applicant: Neovasc Tiara Inc., Richmond (CA)

(72) Inventors: Shmuel Banai, Tel Aviv (IL); Kathleen Hung, New Westminster (CA); Aaron J. Chalekian, Savage, MN (US); Karen Tsoek-Ji Wong, Richmond (CA); Eric Soun-Sang Fung, Vancouver (CA); Connor Lucas Haberl, Vancouver (CA); David Andrew Moffatt, Richmond (CA)

(73) Assignee: Neovasc Tiara Inc., Richmond (CA)

( * ) Notice: Subject to any disclaimer, the term of this patent is extended or adjusted under 35 U.S.C. 154(b) by 0 days.

(21) Appl. No.: 17/959,790

(22) Filed: Oct. 4, 2022

(65) Prior Publication Data

US 2023/0100125 A1 Mar. 30, 2023

Related U.S. Application Data

(63) Continuation of application No. 16/845,870, filed on Apr. 10, 2020, now Pat. No. 11,491,006.

(60) Provisional application No. 62/831,922, filed on Apr. 10, 2019.

(51) Int. Cl.
*A61F 2/24* (2006.01)
*A61F 2/06* (2013.01)

(52) U.S. Cl.
CPC .......... *A61F 2/2418* (2013.01); *A61F 2/2412* (2013.01); *A61F 2002/068* (2013.01); *A61F 2/2448* (2013.01); *A61F 2/2454* (2013.01); *A61F 2/2463* (2013.01); *A61F 2/2466* (2013.01)

(58) Field of Classification Search
CPC ............................ A61F 2/2418; A61F 2/2463
See application file for complete search history.

(56) References Cited

U.S. PATENT DOCUMENTS

| 2,967,856 | A | 1/1961 | Coover, Jr. et al. |
| 5,957,949 | A | 9/1999 | Leonhardt et al. |
| 6,425,916 | B1 | 7/2002 | Garrison et al. |
| 7,273,493 | B2 | 9/2007 | Ledergerber |
| 7,771,467 | B2 | 8/2010 | Svensson |
| 7,871,435 | B2 | 1/2011 | Carpentier et al. |

(Continued)

FOREIGN PATENT DOCUMENTS

| AU | 2011250606 B2 | 3/2014 |
| AU | 2014203064 A1 | 7/2014 |

(Continued)

OTHER PUBLICATIONS

"Canadian Application Serial No. 3,136,334, Examiner's Rule 86(2) Report mailed Dec. 20, 2022", 4 pgs.

(Continued)

*Primary Examiner* — Suba Ganesan
(74) *Attorney, Agent, or Firm* — Schwegman Lundberg & Woessner, P.A.

(57) ABSTRACT

A prosthetic valve may be formed to direct flow out of the outflow orifice toward a posterior portion of a heart wall. The prosthetic valve includes an expandable frame which may be covered with a cover that is suturelessly attached to the frame. The prosthetic valve may also include an outflow orifice size which is controlled. Methods of using these devices are also disclosed.

17 Claims, 52 Drawing Sheets

(56) References Cited

U.S. PATENT DOCUMENTS

| | | |
|---|---|---|
| 8,579,964 B2 | 11/2013 | Lane et al. |
| 10,433,952 B2 | 10/2019 | Lane et al. |
| 11,357,622 B2 | 6/2022 | Lane et al. |
| 11,491,006 B2 | 11/2022 | Banai et al. |
| 2004/0117009 A1 | 6/2004 | Cali et al. |
| 2004/0181238 A1 | 9/2004 | Zarbatany et al. |
| 2006/0259136 A1 | 11/2006 | Nguyen et al. |
| 2006/0282157 A1 | 12/2006 | Hill et al. |
| 2006/0293745 A1 | 12/2006 | Carpentier et al. |
| 2007/0050021 A1 | 3/2007 | Johnson |
| 2011/0319989 A1 | 12/2011 | Lane et al. |
| 2012/0239143 A1 | 9/2012 | Rankin et al. |
| 2013/0211508 A1* | 8/2013 | Lane ............... A61F 2/2427 623/2.11 |
| 2014/0039611 A1 | 2/2014 | Lane et al. |
| 2014/0052237 A1 | 2/2014 | Lane et al. |
| 2014/0155990 A1 | 6/2014 | Nyuli et al. |
| 2014/0257467 A1 | 9/2014 | Lane et al. |
| 2014/0343669 A1 | 11/2014 | Lane et al. |
| 2015/0216655 A1 | 8/2015 | Lane et al. |
| 2015/0257878 A1 | 9/2015 | Lane et al. |
| 2016/0113764 A1 | 4/2016 | Sheahan et al. |
| 2016/0157999 A1 | 6/2016 | Lane et al. |
| 2016/0235526 A1* | 8/2016 | Lashinski ............ A61F 2/2418 |
| 2017/0165064 A1 | 6/2017 | Nyuli et al. |
| 2017/0216023 A1 | 8/2017 | Lane et al. |
| 2017/0231760 A1 | 8/2017 | Lane et al. |
| 2017/0281336 A1 | 10/2017 | Lane et al. |
| 2017/0348100 A1 | 12/2017 | Lane et al. |
| 2018/0325703 A1 | 11/2018 | Shahriari |
| 2019/0021839 A1 | 1/2019 | Kölbel |
| 2019/0358032 A1 | 11/2019 | Lane et al. |
| 2019/0388219 A1 | 12/2019 | Lane et al. |
| 2020/0015965 A1 | 1/2020 | Lane et al. |
| 2020/0146818 A1 | 5/2020 | Lane et al. |
| 2020/0323637 A1 | 10/2020 | Banai et al. |
| 2022/0257370 A1 | 8/2022 | Lane et al. |

FOREIGN PATENT DOCUMENTS

| | | |
|---|---|---|
| AU | 2020271896 B2 | 10/2022 |
| CA | 2619080 A1 | 3/2007 |
| CA | 2797863 A1 | 11/2011 |
| CA | 3043737 A1 | 11/2011 |
| CA | 3007670 A1 | 8/2017 |
| CA | 2874219 C | 7/2020 |
| CN | 101262833 A | 9/2008 |
| CN | 102639179 A | 8/2012 |
| CN | 103079498 A | 5/2013 |
| CN | 105283149 A | 1/2016 |
| CN | 105287050 A | 2/2016 |
| CN | 108882981 A | 11/2018 |
| CN | 113633435 A | 11/2021 |
| CN | 113924065 A | 1/2022 |
| DE | 10103955 B4 | 11/2001 |
| DE | 10033858 B4 | 1/2002 |
| DE | 102006052564 B3 | 12/2007 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 20201111106.0 U1 | 3/2020 |
| DE | 20201111107.9 U1 | 3/2020 |
| DE | 202017007326 U1 | 10/2020 |
| DE | 102009009158 B4 | 11/2020 |
| EP | 1077072 B1 | 11/2003 |
| EP | 1140244 B1 | 11/2003 |
| EP | 1214106 B1 | 11/2003 |
| EP | 1143864 B1 | 2/2004 |
| EP | 1220651 B1 | 3/2004 |
| EP | 1265534 B1 | 6/2004 |
| EP | 1347785 B1 | 7/2004 |
| EP | 1245202 B1 | 8/2004 |
| EP | 1161204 B1 | 9/2004 |
| EP | 1266641 B1 | 10/2004 |
| EP | 1102567 B1 | 11/2004 |
| EP | 1117446 B1 | 11/2004 |
| EP | 1107710 B1 | 12/2004 |
| EP | 1121070 B1 | 12/2004 |
| EP | 1217966 B1 | 12/2004 |
| EP | 1233731 B1 | 12/2004 |
| EP | 1294318 B1 | 12/2004 |
| EP | 1237510 B1 | 1/2005 |
| EP | 1034753 B1 | 2/2005 |
| EP | 1259194 B1 | 2/2005 |
| EP | 1121069 B1 | 3/2005 |
| EP | 1143879 B1 | 3/2005 |
| EP | 1023879 B1 | 4/2005 |
| EP | 1339356 B1 | 4/2005 |
| EP | 1214022 B1 | 5/2005 |
| EP | 1318774 B1 | 5/2005 |
| EP | 1088529 B1 | 6/2005 |
| EP | 1171060 B1 | 6/2005 |
| EP | 1251803 B1 | 6/2005 |
| EP | 1259776 B1 | 6/2005 |
| EP | 1272123 B1 | 6/2005 |
| EP | 1049422 B1 | 7/2005 |
| EP | 1230901 B1 | 8/2005 |
| EP | 1335633 B1 | 8/2005 |
| EP | 1307246 B1 | 9/2005 |
| EP | 1267753 B1 | 10/2005 |
| EP | 1284688 B1 | 10/2005 |
| EP | 1343536 B1 | 10/2005 |
| EP | 1027020 B1 | 11/2005 |
| EP | 1152780 B1 | 11/2005 |
| EP | 1171059 B1 | 11/2005 |
| EP | 1237508 B1 | 11/2005 |
| EP | 1303234 B1 | 11/2005 |
| EP | 1328215 B1 | 11/2005 |
| EP | 1341487 B1 | 11/2005 |
| EP | 1392197 B1 | 11/2005 |
| EP | 1469797 B1 | 11/2005 |
| EP | 1255505 B1 | 12/2005 |
| EP | 1360942 B1 | 12/2005 |
| EP | 1322260 B1 | 1/2006 |
| EP | 1359870 B1 | 1/2006 |
| EP | 1237586 B1 | 2/2006 |
| EP | 1112043 B1 | 4/2006 |
| EP | 1309360 B1 | 4/2006 |
| EP | 1322259 B1 | 5/2006 |
| EP | 1124592 B1 | 6/2006 |
| EP | 1237516 B1 | 6/2006 |
| EP | 1098673 B1 | 7/2006 |
| EP | 1124591 B1 | 7/2006 |
| EP | 1083845 B1 | 8/2006 |
| EP | 1155666 B1 | 8/2006 |
| EP | 1463462 B1 | 8/2006 |
| EP | 1684671 A1 | 8/2006 |
| EP | 1519695 B1 | 9/2006 |
| EP | 1444993 B1 | 10/2006 |
| EP | 1117350 B1 | 11/2006 |

(56) References Cited

FOREIGN PATENT DOCUMENTS

| | | | |
|---|---|---|---|
| EP | 1212011 | B1 | 11/2006 |
| EP | 1261294 | B1 | 11/2006 |
| EP | 1318775 | B1 | 11/2006 |
| EP | 1429690 | B1 | 11/2006 |
| EP | 1173111 | B1 | 12/2006 |
| EP | 1239795 | B1 | 12/2006 |
| EP | 1299049 | B1 | 12/2006 |
| EP | 1487382 | B1 | 12/2006 |
| EP | 1112044 | B1 | 1/2007 |
| EP | 1482997 | B1 | 1/2007 |
| EP | 1117352 | B1 | 2/2007 |
| EP | 1128849 | B1 | 2/2007 |
| EP | 1392666 | B1 | 2/2007 |
| EP | 1474077 | B1 | 2/2007 |
| EP | 1251805 | B1 | 3/2007 |
| EP | 1117334 | B1 | 4/2007 |
| EP | 1263484 | B1 | 5/2007 |
| EP | 1313410 | B1 | 5/2007 |
| EP | 1370200 | B1 | 5/2007 |
| EP | 1560526 | B1 | 6/2007 |
| EP | 1173117 | B1 | 7/2007 |
| EP | 1434615 | B1 | 7/2007 |
| EP | 1465546 | B1 | 7/2007 |
| EP | 1499366 | B1 | 7/2007 |
| EP | 1225948 | B1 | 8/2007 |
| EP | 1819304 | A2 | 8/2007 |
| EP | 1519962 | B1 | 9/2007 |
| EP | 1337285 | B1 | 10/2007 |
| EP | 1112042 | B1 | 11/2007 |
| EP | 1148821 | B1 | 11/2007 |
| EP | 1143882 | B1 | 12/2007 |
| EP | 1330189 | B1 | 12/2007 |
| EP | 1489996 | B1 | 12/2007 |
| EP | 1296618 | B1 | 1/2008 |
| EP | 1401356 | B1 | 1/2008 |
| EP | 1629795 | B1 | 1/2008 |
| EP | 1128786 | B1 | 2/2008 |
| EP | 1616532 | B1 | 2/2008 |
| EP | 1289447 | B1 | 3/2008 |
| EP | 1895942 | A2 | 3/2008 |
| EP | 1115353 | B1 | 5/2008 |
| EP | 1330190 | B1 | 5/2008 |
| EP | 1924223 | A1 | 5/2008 |
| EP | 1383448 | B1 | 6/2008 |
| EP | 1251804 | B1 | 7/2008 |
| EP | 1294310 | B1 | 7/2008 |
| EP | 1313409 | B1 | 7/2008 |
| EP | 1395202 | B1 | 7/2008 |
| EP | 1395204 | B1 | 7/2008 |
| EP | 1395205 | B1 | 7/2008 |
| EP | 1423066 | B1 | 7/2008 |
| EP | 1560545 | B1 | 7/2008 |
| EP | 1605871 | B1 | 7/2008 |
| EP | 1671608 | B1 | 7/2008 |
| EP | 1690515 | B1 | 7/2008 |
| EP | 1180987 | B1 | 8/2008 |
| EP | 1337386 | B1 | 8/2008 |
| EP | 1492579 | B1 | 9/2008 |
| EP | 1524942 | B1 | 9/2008 |
| EP | 1627091 | B1 | 9/2008 |
| EP | 1827577 | B1 | 9/2008 |
| EP | 1259195 | B1 | 10/2008 |
| EP | 1704834 | B1 | 10/2008 |
| EP | 1146835 | B1 | 11/2008 |
| EP | 1498086 | B1 | 11/2008 |
| EP | 1622548 | B1 | 11/2008 |
| EP | 1235537 | B1 | 12/2008 |
| EP | 1237509 | B1 | 12/2008 |
| EP | 1355590 | B1 | 12/2008 |
| EP | 1455680 | B1 | 12/2008 |
| EP | 1472995 | B1 | 12/2008 |
| EP | 1513474 | B1 | 12/2008 |
| EP | 1562522 | B1 | 12/2008 |
| EP | 1620042 | B1 | 12/2008 |
| EP | 1690514 | B1 | 12/2008 |
| EP | 1258232 | B1 | 1/2009 |
| EP | 1420723 | B1 | 1/2009 |
| EP | 1570809 | B1 | 1/2009 |
| EP | 1395182 | B1 | 2/2009 |
| EP | 1408882 | B1 | 2/2009 |
| EP | 1482868 | B1 | 2/2009 |
| EP | 1255510 | B3 | 3/2009 |
| EP | 1330213 | B1 | 3/2009 |
| EP | 1429651 | B1 | 3/2009 |
| EP | 1610727 | B1 | 4/2009 |
| EP | 1617788 | B1 | 4/2009 |
| EP | 1634547 | B1 | 4/2009 |
| EP | 1790318 | B1 | 4/2009 |
| EP | 2040645 | A1 | 4/2009 |
| EP | 1250165 | B1 | 5/2009 |
| EP | 1842508 | B1 | 6/2009 |
| EP | 1968482 | B1 | 6/2009 |
| EP | 2072027 | A1 | 6/2009 |
| EP | 1343438 | B1 | 7/2009 |
| EP | 1406608 | B1 | 7/2009 |
| EP | 1509256 | B1 | 7/2009 |
| EP | 1626681 | B1 | 7/2009 |
| EP | 1723935 | B1 | 7/2009 |
| EP | 1803420 | B1 | 7/2009 |
| EP | 2073755 | A2 | 7/2009 |
| EP | 1401359 | B1 | 8/2009 |
| EP | 1411865 | B1 | 8/2009 |
| EP | 1485033 | B1 | 8/2009 |
| EP | 1581120 | B1 | 8/2009 |
| EP | 1620040 | B1 | 8/2009 |
| EP | 1684667 | B1 | 8/2009 |
| EP | 1872743 | B1 | 8/2009 |
| EP | 1100378 | B1 | 9/2009 |
| EP | 1198203 | B1 | 9/2009 |
| EP | 1370201 | B1 | 9/2009 |
| EP | 1408850 | B1 | 9/2009 |
| EP | 1472996 | B1 | 9/2009 |
| EP | 1478364 | B1 | 9/2009 |
| EP | 1653888 | B1 | 9/2009 |
| EP | 1785154 | B1 | 9/2009 |
| EP | 1881804 | B1 | 9/2009 |
| EP | 1903991 | B1 | 9/2009 |
| EP | 1418865 | B1 | 10/2009 |
| EP | 1561437 | B1 | 10/2009 |
| EP | 1615595 | B1 | 10/2009 |
| EP | 1353612 | B1 | 11/2009 |
| EP | 1348406 | B1 | 12/2009 |
| EP | 1370202 | B1 | 12/2009 |
| EP | 1603492 | B1 | 12/2009 |
| EP | 1670364 | B1 | 12/2009 |
| EP | 1759663 | B1 | 12/2009 |
| EP | 1994887 | B1 | 12/2009 |
| EP | 1615593 | B1 | 1/2010 |
| EP | 1643938 | B1 | 1/2010 |
| EP | 1863402 | B1 | 1/2010 |
| EP | 1943942 | B1 | 1/2010 |
| EP | 2010101 | B1 | 1/2010 |
| EP | 2081518 | B1 | 1/2010 |
| EP | 1703865 | B1 | 2/2010 |
| EP | 1276437 | B1 | 3/2010 |
| EP | 1276439 | B1 | 3/2010 |
| EP | 1411867 | B1 | 3/2010 |
| EP | 1458313 | B1 | 3/2010 |
| EP | 1520519 | B1 | 3/2010 |
| EP | 1648340 | B1 | 3/2010 |
| EP | 1682048 | B1 | 3/2010 |
| EP | 1773239 | B1 | 3/2010 |
| EP | 1935377 | B1 | 3/2010 |
| EP | 1994912 | B1 | 3/2010 |
| EP | 1154738 | B1 | 4/2010 |
| EP | 1531762 | B1 | 4/2010 |
| EP | 1600178 | B1 | 4/2010 |
| EP | 1626682 | B1 | 4/2010 |
| EP | 1511445 | B1 | 5/2010 |
| EP | 1198213 | B1 | 6/2010 |
| EP | 1250097 | B1 | 6/2010 |
| EP | 1272249 | B1 | 6/2010 |
| EP | 1978895 | B1 | 6/2010 |
| EP | 1572033 | B1 | 7/2010 |

(56) References Cited

FOREIGN PATENT DOCUMENTS

| | | | |
|---|---|---|---|
| EP | 1968491 | B1 | 7/2010 |
| EP | 2019652 | B1 | 7/2010 |
| EP | 1610722 | B1 | 8/2010 |
| EP | 1682047 | B1 | 8/2010 |
| EP | 1952772 | B1 | 8/2010 |
| EP | 1427356 | B1 | 9/2010 |
| EP | 1631218 | B1 | 9/2010 |
| EP | 1765224 | B1 | 9/2010 |
| EP | 1871290 | B1 | 9/2010 |
| EP | 1895288 | B1 | 9/2010 |
| EP | 1895913 | B1 | 9/2010 |
| EP | 2014257 | B1 | 9/2010 |
| EP | 1176913 | B1 | 10/2010 |
| EP | 1178758 | B1 | 10/2010 |
| EP | 1248579 | B1 | 10/2010 |
| EP | 1913899 | B1 | 10/2010 |
| EP | 1259193 | B1 | 11/2010 |
| EP | 1928357 | B1 | 11/2010 |
| EP | 1968660 | B1 | 11/2010 |
| EP | 2249711 | A2 | 11/2010 |
| EP | 1408895 | B1 | 12/2010 |
| EP | 1465554 | B1 | 12/2010 |
| EP | 1732473 | B1 | 12/2010 |
| EP | 1768610 | B1 | 12/2010 |
| EP | 1827314 | B1 | 12/2010 |
| EP | 1940321 | B1 | 12/2010 |
| EP | 1964532 | B1 | 12/2010 |
| EP | 2078498 | B1 | 12/2010 |
| EP | 1600182 | B1 | 1/2011 |
| EP | 1617789 | B1 | 1/2011 |
| EP | 1663332 | B1 | 1/2011 |
| EP | 2147659 | B1 | 1/2011 |
| EP | 2268231 | A2 | 1/2011 |
| EP | 2273951 | A1 | 1/2011 |
| EP | 1187582 | B1 | 2/2011 |
| EP | 1450733 | B1 | 2/2011 |
| EP | 1803421 | B1 | 2/2011 |
| EP | 1833425 | B1 | 2/2011 |
| EP | 2029053 | B1 | 2/2011 |
| EP | 2068770 | B1 | 2/2011 |
| EP | 1441784 | B1 | 3/2011 |
| EP | 1534177 | B1 | 3/2011 |
| EP | 1893132 | B1 | 3/2011 |
| EP | 1951153 | B1 | 3/2011 |
| EP | 2289467 | A1 | 3/2011 |
| EP | 2299938 | A2 | 3/2011 |
| EP | 1359978 | B1 | 4/2011 |
| EP | 1667750 | B1 | 4/2011 |
| EP | 1718249 | B1 | 4/2011 |
| EP | 1903989 | B1 | 4/2011 |
| EP | 2018122 | B1 | 4/2011 |
| EP | 1610728 | B1 | 5/2011 |
| EP | 2105110 | B1 | 5/2011 |
| EP | 1347717 | B1 | 6/2011 |
| EP | 2331018 | A1 | 6/2011 |
| EP | 1347791 | B1 | 7/2011 |
| EP | 1862128 | B1 | 7/2011 |
| EP | 2120795 | B1 | 7/2011 |
| EP | 2229920 | B1 | 7/2011 |
| EP | 1637087 | B1 | 8/2011 |
| EP | 2153799 | B1 | 8/2011 |
| EP | 2247263 | B1 | 8/2011 |
| EP | 2349095 | A1 | 8/2011 |
| EP | 2349097 | A1 | 8/2011 |
| EP | 2349098 | A1 | 8/2011 |
| EP | 2358307 | A1 | 8/2011 |
| EP | 1441672 | B1 | 9/2011 |
| EP | 1625832 | B1 | 9/2011 |
| EP | 2173279 | B1 | 9/2011 |
| EP | 2367505 | A1 | 9/2011 |
| EP | 2160150 | B1 | 10/2011 |
| EP | 2370138 | A2 | 10/2011 |
| EP | 1626679 | B1 | 11/2011 |
| EP | 1719476 | B1 | 11/2011 |
| EP | 1928355 | B1 | 11/2011 |
| EP | 2237747 | B1 | 11/2011 |
| EP | 2381895 | A2 | 11/2011 |
| EP | 2389121 | A1 | 11/2011 |
| EP | 1572031 | B1 | 12/2011 |
| EP | 1603493 | B1 | 12/2011 |
| EP | 1945109 | B1 | 12/2011 |
| EP | 1998688 | B1 | 12/2011 |
| EP | 2393442 | A2 | 12/2011 |
| EP | 2395944 | A1 | 12/2011 |
| EP | 1443877 | B1 | 1/2012 |
| EP | 2400922 | A1 | 1/2012 |
| EP | 1281375 | B1 | 2/2012 |
| EP | 1699501 | B1 | 2/2012 |
| EP | 1788984 | B1 | 2/2012 |
| EP | 1833415 | B1 | 2/2012 |
| EP | 1952785 | B1 | 2/2012 |
| EP | 2055266 | B1 | 2/2012 |
| EP | 2205184 | B1 | 2/2012 |
| EP | 2416736 | A1 | 2/2012 |
| EP | 1337188 | B1 | 3/2012 |
| EP | 1443974 | B1 | 3/2012 |
| EP | 1542623 | B1 | 3/2012 |
| EP | 1942835 | B1 | 3/2012 |
| EP | 2074964 | B1 | 3/2012 |
| EP | 2244661 | B1 | 3/2012 |
| EP | 2273928 | B1 | 3/2012 |
| EP | 2427144 | A1 | 3/2012 |
| EP | 2429455 | A1 | 3/2012 |
| EP | 1401336 | B1 | 4/2012 |
| EP | 1749544 | B1 | 4/2012 |
| EP | 2119417 | B1 | 4/2012 |
| EP | 2152330 | B1 | 4/2012 |
| EP | 2231069 | B1 | 4/2012 |
| EP | 2437688 | A2 | 4/2012 |
| EP | 2020958 | B1 | 5/2012 |
| EP | 2192875 | B1 | 5/2012 |
| EP | 2218425 | B1 | 5/2012 |
| EP | 2445450 | A2 | 5/2012 |
| EP | 1411847 | B1 | 6/2012 |
| EP | 1727499 | B1 | 6/2012 |
| EP | 2082690 | B1 | 6/2012 |
| EP | 1740747 | B1 | 7/2012 |
| EP | 1861044 | B1 | 7/2012 |
| EP | 2052699 | B1 | 7/2012 |
| EP | 2470121 | A2 | 7/2012 |
| EP | 2471492 | A1 | 7/2012 |
| EP | 1887975 | B1 | 8/2012 |
| EP | 2000116 | B1 | 8/2012 |
| EP | 2222247 | B1 | 8/2012 |
| EP | 2486894 | A1 | 8/2012 |
| EP | 1605870 | B1 | 9/2012 |
| EP | 1887980 | B1 | 9/2012 |
| EP | 2497445 | A1 | 9/2012 |
| EP | 1740126 | B1 | 10/2012 |
| EP | 1865889 | B1 | 10/2012 |
| EP | 2033593 | B1 | 10/2012 |
| EP | 2124824 | B1 | 10/2012 |
| EP | 2139431 | B1 | 10/2012 |
| EP | 2506777 | A1 | 10/2012 |
| EP | 2512952 | A2 | 10/2012 |
| EP | 1430853 | B1 | 11/2012 |
| EP | 1928512 | B1 | 11/2012 |
| EP | 2008615 | B1 | 11/2012 |
| EP | 2088965 | B1 | 11/2012 |
| EP | 2520249 | A1 | 11/2012 |
| EP | 2522307 | A1 | 11/2012 |
| EP | 1557138 | B1 | 12/2012 |
| EP | 1924221 | B1 | 12/2012 |
| EP | 2023859 | B1 | 12/2012 |
| EP | 2250970 | B1 | 12/2012 |
| EP | 2285317 | B1 | 12/2012 |
| EP | 2536353 | A1 | 12/2012 |
| EP | 2537486 | A1 | 12/2012 |
| EP | 1494731 | B1 | 1/2013 |
| EP | 1610752 | B1 | 1/2013 |
| EP | 1796597 | B1 | 1/2013 |
| EP | 1919397 | B1 | 1/2013 |
| EP | 1942834 | B1 | 1/2013 |
| EP | 2015709 | B1 | 1/2013 |

(56) References Cited

FOREIGN PATENT DOCUMENTS

| | | | |
|---|---|---|---|
| EP | 2079400 | B1 | 1/2013 |
| EP | 2238947 | B1 | 1/2013 |
| EP | 2241287 | B1 | 1/2013 |
| EP | 2359774 | B1 | 1/2013 |
| EP | 2538878 | A1 | 1/2013 |
| EP | 2538881 | A1 | 1/2013 |
| EP | 2538882 | A1 | 1/2013 |
| EP | 2538883 | A1 | 1/2013 |
| EP | 1512383 | B1 | 2/2013 |
| EP | 1578474 | B1 | 2/2013 |
| EP | 1648339 | B1 | 2/2013 |
| EP | 1750622 | B1 | 2/2013 |
| EP | 1994482 | B1 | 2/2013 |
| EP | 2250975 | B1 | 2/2013 |
| EP | 2257242 | B1 | 2/2013 |
| EP | 2265225 | B1 | 2/2013 |
| EP | 2558032 | A1 | 2/2013 |
| EP | 1659992 | B1 | 3/2013 |
| EP | 1701668 | B1 | 3/2013 |
| EP | 2151216 | B1 | 3/2013 |
| EP | 2340075 | B1 | 3/2013 |
| EP | 2566416 | A1 | 3/2013 |
| EP | 2568924 | A2 | 3/2013 |
| EP | 1781183 | B1 | 4/2013 |
| EP | 1786367 | B1 | 4/2013 |
| EP | 1850795 | B1 | 4/2013 |
| EP | 1861041 | B1 | 4/2013 |
| EP | 2319458 | B1 | 4/2013 |
| EP | 2526898 | B1 | 4/2013 |
| EP | 2537487 | B1 | 4/2013 |
| EP | 2575681 | A1 | 4/2013 |
| EP | 1901682 | B1 | 5/2013 |
| EP | 1951166 | B1 | 5/2013 |
| EP | 1994913 | B1 | 5/2013 |
| EP | 2231070 | B1 | 5/2013 |
| EP | 2401970 | B1 | 5/2013 |
| EP | 2409651 | B1 | 5/2013 |
| EP | 2594230 | A1 | 5/2013 |
| EP | 1694246 | B1 | 6/2013 |
| EP | 1948087 | B1 | 6/2013 |
| EP | 2135559 | B1 | 6/2013 |
| EP | 1115335 | B1 | 7/2013 |
| EP | 1663339 | B1 | 7/2013 |
| EP | 1864687 | B1 | 7/2013 |
| EP | 1977719 | B1 | 7/2013 |
| EP | 2111337 | B1 | 7/2013 |
| EP | 2298237 | B1 | 7/2013 |
| EP | 2309949 | B1 | 7/2013 |
| EP | 2608741 | A2 | 7/2013 |
| EP | 2611388 | A2 | 7/2013 |
| EP | 2611389 | A2 | 7/2013 |
| EP | 2618781 | A2 | 7/2013 |
| EP | 1599151 | B1 | 8/2013 |
| EP | 1761211 | B1 | 8/2013 |
| EP | 2047871 | B1 | 8/2013 |
| EP | 2142144 | B1 | 8/2013 |
| EP | 2150206 | B1 | 8/2013 |
| EP | 2319459 | B1 | 8/2013 |
| EP | 2397108 | B1 | 8/2013 |
| EP | 2623068 | A1 | 8/2013 |
| EP | 1758523 | B1 | 9/2013 |
| EP | 1545392 | B1 | 10/2013 |
| EP | 1638627 | B1 | 10/2013 |
| EP | 1779868 | B1 | 10/2013 |
| EP | 2073756 | B1 | 10/2013 |
| EP | 2111190 | B1 | 10/2013 |
| EP | 2651336 | A1 | 10/2013 |
| EP | 1848375 | B1 | 11/2013 |
| EP | 1928356 | B1 | 11/2013 |
| EP | 1933766 | B1 | 11/2013 |
| EP | 2109417 | B1 | 11/2013 |
| EP | 2194925 | B1 | 11/2013 |
| EP | 2387977 | B1 | 11/2013 |
| EP | 2476394 | B1 | 11/2013 |
| EP | 2529701 | B1 | 11/2013 |
| EP | 1945142 | B1 | 12/2013 |
| EP | 2387972 | B1 | 12/2013 |
| EP | 2477555 | B1 | 12/2013 |
| EP | 2670349 | A2 | 12/2013 |
| EP | 2670351 | A1 | 12/2013 |
| EP | 2117476 | B1 | 1/2014 |
| EP | 2526895 | B1 | 1/2014 |
| EP | 2526899 | B1 | 1/2014 |
| EP | 2529696 | B1 | 1/2014 |
| EP | 2529697 | B1 | 1/2014 |
| EP | 2529698 | B1 | 1/2014 |
| EP | 2529699 | B1 | 1/2014 |
| EP | 2679198 | A1 | 1/2014 |
| EP | 2688516 | A1 | 1/2014 |
| EP | 1395214 | B1 | 2/2014 |
| EP | 1499266 | B1 | 2/2014 |
| EP | 1838241 | B1 | 2/2014 |
| EP | 2520250 | B1 | 2/2014 |
| EP | 2526977 | B1 | 2/2014 |
| EP | 2693985 | A1 | 2/2014 |
| EP | 2698129 | A1 | 2/2014 |
| EP | 2699302 | A2 | 2/2014 |
| EP | 1629794 | B1 | 3/2014 |
| EP | 1919398 | B1 | 3/2014 |
| EP | 2099508 | B1 | 3/2014 |
| EP | 2399549 | B1 | 3/2014 |
| EP | 2422823 | B1 | 3/2014 |
| EP | 2706958 | A1 | 3/2014 |
| EP | 1804860 | B1 | 4/2014 |
| EP | 1926455 | B1 | 4/2014 |
| EP | 2081519 | B1 | 4/2014 |
| EP | 2117477 | B1 | 4/2014 |
| EP | 2405966 | B1 | 4/2014 |
| EP | 2420205 | B1 | 4/2014 |
| EP | 2593048 | B1 | 4/2014 |
| EP | 2713894 | A2 | 4/2014 |
| EP | 2713955 | A2 | 4/2014 |
| EP | 2723273 | A2 | 4/2014 |
| EP | 1499265 | B1 | 5/2014 |
| EP | 1594569 | B1 | 5/2014 |
| EP | 2029056 | B1 | 5/2014 |
| EP | 2257243 | B1 | 5/2014 |
| EP | 1791500 | B1 | 6/2014 |
| EP | 2073753 | B1 | 6/2014 |
| EP | 2306933 | B1 | 6/2014 |
| EP | 2331017 | B1 | 6/2014 |
| EP | 2337522 | B1 | 6/2014 |
| EP | 2389897 | B1 | 6/2014 |
| EP | 2606723 | B1 | 6/2014 |
| EP | 2739250 | A1 | 6/2014 |
| EP | 1487350 | B1 | 7/2014 |
| EP | 1977718 | B1 | 7/2014 |
| EP | 2117469 | B1 | 7/2014 |
| EP | 2124826 | B1 | 7/2014 |
| EP | 2258316 | B1 | 7/2014 |
| EP | 2747708 | A1 | 7/2014 |
| EP | 2750630 | A1 | 7/2014 |
| EP | 2750631 | A1 | 7/2014 |
| EP | 1667604 | B1 | 8/2014 |
| EP | 1786368 | B1 | 8/2014 |
| EP | 2211779 | B1 | 8/2014 |
| EP | 2217174 | B1 | 8/2014 |
| EP | 2293740 | B1 | 8/2014 |
| EP | 2367504 | B1 | 8/2014 |
| EP | 2453942 | B1 | 8/2014 |
| EP | 2475328 | B1 | 8/2014 |
| EP | 2545864 | B1 | 8/2014 |
| EP | 2571460 | B1 | 8/2014 |
| EP | 2763708 | A2 | 8/2014 |
| EP | 2765954 | A1 | 8/2014 |
| EP | 1935378 | B1 | 9/2014 |
| EP | 2246011 | B1 | 9/2014 |
| EP | 2422749 | B1 | 9/2014 |
| EP | 2531139 | B1 | 9/2014 |
| EP | 2609893 | B1 | 9/2014 |
| EP | 2777616 | A1 | 9/2014 |
| EP | 2779945 | A1 | 9/2014 |
| EP | 1853199 | B1 | 10/2014 |
| EP | 2133039 | B1 | 10/2014 |

(56) References Cited

FOREIGN PATENT DOCUMENTS

| | | | |
|---|---|---|---|
| EP | 2549955 B1 | 10/2014 |
| EP | 2549956 B1 | 10/2014 |
| EP | 2651335 B1 | 10/2014 |
| EP | 2785281 A1 | 10/2014 |
| EP | 2793743 A1 | 10/2014 |
| EP | 2793749 A1 | 10/2014 |
| EP | 2793752 A1 | 10/2014 |
| EP | 2049721 B1 | 11/2014 |
| EP | 2142143 B1 | 11/2014 |
| EP | 2229921 B1 | 11/2014 |
| EP | 2288403 B1 | 11/2014 |
| EP | 2415421 B1 | 11/2014 |
| EP | 1551274 B1 | 12/2014 |
| EP | 1768735 B1 | 12/2014 |
| EP | 1959865 B1 | 12/2014 |
| EP | 2077718 B1 | 12/2014 |
| EP | 2303185 B1 | 12/2014 |
| EP | 2334857 B1 | 12/2014 |
| EP | 2365840 B1 | 12/2014 |
| EP | 2420207 B1 | 12/2014 |
| EP | 2422750 B1 | 12/2014 |
| EP | 2707073 B1 | 12/2014 |
| EP | 1768630 B1 | 1/2015 |
| EP | 2254515 B1 | 1/2015 |
| EP | 2641569 B1 | 1/2015 |
| EP | 2709559 B1 | 1/2015 |
| EP | 2825203 A1 | 1/2015 |
| EP | 1903990 B1 | 2/2015 |
| EP | 2255753 B1 | 2/2015 |
| EP | 2335649 B1 | 2/2015 |
| EP | 2522308 B1 | 2/2015 |
| EP | 2591754 B1 | 2/2015 |
| EP | 2835112 A1 | 2/2015 |
| EP | 2838473 A1 | 2/2015 |
| EP | 1861045 B1 | 3/2015 |
| EP | 2029057 B1 | 3/2015 |
| EP | 2193761 B1 | 3/2015 |
| EP | 2379010 B1 | 3/2015 |
| EP | 2416737 B1 | 3/2015 |
| EP | 2849678 A1 | 3/2015 |
| EP | 1791495 B1 | 4/2015 |
| EP | 2298252 B1 | 4/2015 |
| EP | 2536359 B1 | 4/2015 |
| EP | 2538879 B1 | 4/2015 |
| EP | 2609894 B1 | 4/2015 |
| EP | 2693984 B1 | 4/2015 |
| EP | 2712633 B1 | 4/2015 |
| EP | 2747707 B1 | 4/2015 |
| EP | 2856973 A1 | 4/2015 |
| EP | 2862546 A1 | 4/2015 |
| EP | 2863842 A1 | 4/2015 |
| EP | 1465555 B1 | 5/2015 |
| EP | 1924224 B1 | 5/2015 |
| EP | 1992369 B1 | 5/2015 |
| EP | 2410947 B1 | 5/2015 |
| EP | 2484311 B1 | 5/2015 |
| EP | 2654616 B1 | 5/2015 |
| EP | 2866741 A1 | 5/2015 |
| EP | 1646332 B1 | 6/2015 |
| EP | 2745805 B1 | 6/2015 |
| EP | 2749254 B1 | 6/2015 |
| EP | 2877123 A2 | 6/2015 |
| EP | 2882374 A1 | 6/2015 |
| EP | 2884906 A1 | 6/2015 |
| EP | 1729685 B1 | 7/2015 |
| EP | 1976439 B1 | 7/2015 |
| EP | 2068767 B1 | 7/2015 |
| EP | 2068769 B1 | 7/2015 |
| EP | 2444031 B1 | 7/2015 |
| EP | 2455041 B1 | 7/2015 |
| EP | 2498719 B1 | 7/2015 |
| EP | 2558030 B1 | 7/2015 |
| EP | 2752209 B1 | 7/2015 |
| EP | 2892467 A1 | 7/2015 |
| EP | 1702247 B1 | 8/2015 |
| EP | 1729688 B1 | 8/2015 |
| EP | 1887979 B1 | 8/2015 |
| EP | 2032079 B1 | 8/2015 |
| EP | 2219558 B1 | 8/2015 |
| EP | 2234657 B1 | 8/2015 |
| EP | 2250976 B1 | 8/2015 |
| EP | 2262447 B1 | 8/2015 |
| EP | 2303384 B1 | 8/2015 |
| EP | 2387365 B1 | 8/2015 |
| EP | 2560579 B1 | 8/2015 |
| EP | 2575621 B1 | 8/2015 |
| EP | 2590595 B1 | 8/2015 |
| EP | 2709560 B1 | 8/2015 |
| EP | 2755603 B1 | 8/2015 |
| EP | 2906147 A1 | 8/2015 |
| EP | 1534185 B1 | 9/2015 |
| EP | 1765225 B1 | 9/2015 |
| EP | 1778127 B1 | 9/2015 |
| EP | 2094194 B1 | 9/2015 |
| EP | 2201911 B1 | 9/2015 |
| EP | 2306934 B1 | 9/2015 |
| EP | 2397113 B1 | 9/2015 |
| EP | 2453843 B1 | 9/2015 |
| EP | 2459127 B1 | 9/2015 |
| EP | 2675396 B1 | 9/2015 |
| EP | 2675397 B1 | 9/2015 |
| EP | 2736454 B1 | 9/2015 |
| EP | 2754414 A4 | 9/2015 |
| EP | 2790609 B1 | 9/2015 |
| EP | 2805693 B1 | 9/2015 |
| EP | 2911611 A1 | 9/2015 |
| EP | 2916781 A2 | 9/2015 |
| EP | 2919712 A1 | 9/2015 |
| EP | 1734903 B1 | 10/2015 |
| EP | 1863546 B1 | 10/2015 |
| EP | 1900343 B1 | 10/2015 |
| EP | 2081515 B1 | 10/2015 |
| EP | 2191792 B1 | 10/2015 |
| EP | 2254513 B1 | 10/2015 |
| EP | 2381896 B1 | 10/2015 |
| EP | 2450008 B1 | 10/2015 |
| EP | 2544626 B1 | 10/2015 |
| EP | 2561830 B1 | 10/2015 |
| EP | 2600798 B1 | 10/2015 |
| EP | 2626039 B1 | 10/2015 |
| EP | 2647354 B1 | 10/2015 |
| EP | 2729093 B1 | 10/2015 |
| EP | 2836165 B1 | 10/2015 |
| EP | 1863545 B1 | 11/2015 |
| EP | 2303395 B1 | 11/2015 |
| EP | 2497446 B1 | 11/2015 |
| EP | 2772228 B1 | 11/2015 |
| EP | 1482869 B1 | 12/2015 |
| EP | 1551473 B1 | 12/2015 |
| EP | 1748745 B1 | 12/2015 |
| EP | 1755459 B1 | 12/2015 |
| EP | 1850796 B1 | 12/2015 |
| EP | 1922030 B1 | 12/2015 |
| EP | 1954212 B1 | 12/2015 |
| EP | 2424472 B1 | 12/2015 |
| EP | 2470120 B1 | 12/2015 |
| EP | 2542179 B1 | 12/2015 |
| EP | 2948100 A1 | 12/2015 |
| EP | 2948103 A2 | 12/2015 |
| EP | 2950752 A2 | 12/2015 |
| EP | 2959866 A1 | 12/2015 |
| EP | 1991168 B1 | 1/2016 |
| EP | 2254512 B1 | 1/2016 |
| EP | 2422748 B1 | 1/2016 |
| EP | 2962664 A1 | 1/2016 |
| EP | 2964153 A1 | 1/2016 |
| EP | 2967700 A1 | 1/2016 |
| EP | 2967807 A2 | 1/2016 |
| EP | 2967834 A1 | 1/2016 |
| EP | 2967856 A1 | 1/2016 |
| EP | 2967858 A2 | 1/2016 |
| EP | 2967860 A1 | 1/2016 |
| EP | 2967866 A2 | 1/2016 |
| EP | 2977026 A1 | 1/2016 |

(56) References Cited

FOREIGN PATENT DOCUMENTS

| | | | |
|---|---|---|---|
| EP | 1754684 | B1 | 2/2016 |
| EP | 1835948 | B1 | 2/2016 |
| EP | 2012712 | B1 | 2/2016 |
| EP | 2285318 | B1 | 2/2016 |
| EP | 2731550 | B1 | 2/2016 |
| EP | 2926766 | B1 | 2/2016 |
| EP | 2982337 | A1 | 2/2016 |
| EP | 1585463 | B1 | 3/2016 |
| EP | 1638621 | B1 | 3/2016 |
| EP | 1804726 | B1 | 3/2016 |
| EP | 1865886 | B1 | 3/2016 |
| EP | 1887982 | B1 | 3/2016 |
| EP | 2150205 | B1 | 3/2016 |
| EP | 2278944 | B1 | 3/2016 |
| EP | 2291126 | B1 | 3/2016 |
| EP | 2517674 | B1 | 3/2016 |
| EP | 2520253 | B1 | 3/2016 |
| EP | 2526897 | B1 | 3/2016 |
| EP | 2621409 | A4 | 3/2016 |
| EP | 2670353 | B1 | 3/2016 |
| EP | 2674130 | B1 | 3/2016 |
| EP | 2780042 | B1 | 3/2016 |
| EP | 2991584 | A1 | 3/2016 |
| EP | 2991587 | A2 | 3/2016 |
| EP | 2991588 | A1 | 3/2016 |
| EP | 2994072 | A1 | 3/2016 |
| EP | 2994075 | A1 | 3/2016 |
| EP | 2996632 | A1 | 3/2016 |
| EP | 2996633 | A1 | 3/2016 |
| EP | 2996841 | A1 | 3/2016 |
| EP | 2999435 | A1 | 3/2016 |
| EP | 1420730 | B1 | 4/2016 |
| EP | 1545371 | B1 | 4/2016 |
| EP | 1592367 | B1 | 4/2016 |
| EP | 1708649 | B1 | 4/2016 |
| EP | 1871300 | B1 | 4/2016 |
| EP | 2168536 | B1 | 4/2016 |
| EP | 2399550 | B1 | 4/2016 |
| EP | 2433591 | B1 | 4/2016 |
| EP | 2478871 | B1 | 4/2016 |
| EP | 2536355 | B1 | 4/2016 |
| EP | 2572676 | B1 | 4/2016 |
| EP | 2606852 | B1 | 4/2016 |
| EP | 2621408 | B1 | 4/2016 |
| EP | 2626041 | B1 | 4/2016 |
| EP | 2633821 | B1 | 4/2016 |
| EP | 2670354 | B1 | 4/2016 |
| EP | 2702965 | B1 | 4/2016 |
| EP | 2704669 | B1 | 4/2016 |
| EP | 2815725 | B1 | 4/2016 |
| EP | 3007651 | A1 | 4/2016 |
| EP | 3010564 | A1 | 4/2016 |
| EP | 2194933 | B1 | 5/2016 |
| EP | 2237746 | B1 | 5/2016 |
| EP | 2378947 | B1 | 5/2016 |
| EP | 2542184 | B1 | 5/2016 |
| EP | 2572684 | B1 | 5/2016 |
| EP | 2582326 | B1 | 5/2016 |
| EP | 2618784 | B1 | 5/2016 |
| EP | 2654623 | B1 | 5/2016 |
| EP | 2656816 | B1 | 5/2016 |
| EP | 2680791 | B1 | 5/2016 |
| EP | 2693986 | B1 | 5/2016 |
| EP | 2806805 | B1 | 5/2016 |
| EP | 2866739 | B1 | 5/2016 |
| EP | 2889020 | B1 | 5/2016 |
| EP | 2926767 | B1 | 5/2016 |
| EP | 2949292 | B1 | 5/2016 |
| EP | 3019092 | A1 | 5/2016 |
| EP | 1734902 | B1 | 6/2016 |
| EP | 1906884 | B1 | 6/2016 |
| EP | 2111800 | B1 | 6/2016 |
| EP | 2160156 | B1 | 6/2016 |
| EP | 2190379 | B1 | 6/2016 |
| EP | 2193762 | B1 | 6/2016 |
| EP | 2416739 | B1 | 6/2016 |
| EP | 2453969 | B1 | 6/2016 |
| EP | 2515800 | B1 | 6/2016 |
| EP | 2558031 | B1 | 6/2016 |
| EP | 2563236 | B1 | 6/2016 |
| EP | 2572675 | B1 | 6/2016 |
| EP | 2626040 | B1 | 6/2016 |
| EP | 2704668 | B1 | 6/2016 |
| EP | 2777611 | B1 | 6/2016 |
| EP | 2815724 | B1 | 6/2016 |
| EP | 2854710 | B1 | 6/2016 |
| EP | 2901966 | B1 | 6/2016 |
| EP | 3024527 | A2 | 6/2016 |
| EP | 1605866 | B1 | 7/2016 |
| EP | 1933756 | B1 | 7/2016 |
| EP | 2393452 | B1 | 7/2016 |
| EP | 2410948 | B1 | 7/2016 |
| EP | 2412397 | B1 | 7/2016 |
| EP | 2724690 | B1 | 7/2016 |
| EP | 2815723 | B1 | 7/2016 |
| EP | 2870945 | B1 | 7/2016 |
| EP | 3038567 | A1 | 7/2016 |
| EP | 3040054 | A1 | 7/2016 |
| EP | 3042635 | A1 | 7/2016 |
| EP | 3043745 | A1 | 7/2016 |
| EP | 3043747 | A1 | 7/2016 |
| EP | 3043755 | A1 | 7/2016 |
| EP | 1401358 | B1 | 8/2016 |
| EP | 1915105 | B1 | 8/2016 |
| EP | 1937186 | B1 | 8/2016 |
| EP | 2292186 | B1 | 8/2016 |
| EP | 2379012 | B1 | 8/2016 |
| EP | 2385809 | B1 | 8/2016 |
| EP | 2536345 | B1 | 8/2016 |
| EP | 2537490 | B1 | 8/2016 |
| EP | 2549954 | B1 | 8/2016 |
| EP | 2618779 | B1 | 8/2016 |
| EP | 2670352 | B1 | 8/2016 |
| EP | 2829235 | B1 | 8/2016 |
| EP | 2853238 | B1 | 8/2016 |
| EP | 2866738 | B1 | 8/2016 |
| EP | 2906150 | B1 | 8/2016 |
| EP | 3052053 | A1 | 8/2016 |
| EP | 3052611 | A1 | 8/2016 |
| EP | 3060171 | A1 | 8/2016 |
| EP | 3060174 | A1 | 8/2016 |
| EP | 3061421 | A1 | 8/2016 |
| EP | 3061422 | A1 | 8/2016 |
| EP | 1156755 | B1 | 9/2016 |
| EP | 1492478 | B1 | 9/2016 |
| EP | 1912697 | B1 | 9/2016 |
| EP | 2393449 | B1 | 9/2016 |
| EP | 2670356 | B1 | 9/2016 |
| EP | 2793969 | B1 | 9/2016 |
| EP | 2809271 | B1 | 9/2016 |
| EP | 2896425 | B1 | 9/2016 |
| EP | 3068345 | A1 | 9/2016 |
| EP | 3068346 | A1 | 9/2016 |
| EP | 3071148 | A1 | 9/2016 |
| EP | 3071149 | A1 | 9/2016 |
| EP | 2023858 | B1 | 10/2016 |
| EP | 2112912 | B1 | 10/2016 |
| EP | 2640319 | B1 | 10/2016 |
| EP | 2663257 | B1 | 10/2016 |
| EP | 2727612 | B1 | 10/2016 |
| EP | 2760384 | B1 | 10/2016 |
| EP | 2806829 | B1 | 10/2016 |
| EP | 2858599 | B1 | 10/2016 |
| EP | 2918250 | B1 | 10/2016 |
| EP | 2922592 | A4 | 10/2016 |
| EP | 2934387 | B1 | 10/2016 |
| EP | 3076901 | A1 | 10/2016 |
| EP | 3079633 | A1 | 10/2016 |
| EP | 1539047 | B1 | 11/2016 |
| EP | 2282700 | B1 | 11/2016 |
| EP | 2400926 | B1 | 11/2016 |
| EP | 2467104 | B1 | 11/2016 |
| EP | 2525743 | B1 | 11/2016 |
| EP | 2575696 | B1 | 11/2016 |

(56) References Cited

FOREIGN PATENT DOCUMENTS

| | | | |
|---|---|---|---|
| EP | 2598045 | B1 | 11/2016 |
| EP | 2670355 | B1 | 11/2016 |
| EP | 2676640 | B1 | 11/2016 |
| EP | 2680792 | B1 | 11/2016 |
| EP | 2707053 | B1 | 11/2016 |
| EP | 2717803 | B1 | 11/2016 |
| EP | 2773297 | B1 | 11/2016 |
| EP | 2801387 | B1 | 11/2016 |
| EP | 2844192 | B1 | 11/2016 |
| EP | 2849679 | B1 | 11/2016 |
| EP | 2877122 | B1 | 11/2016 |
| EP | 2908778 | B1 | 11/2016 |
| EP | 2922500 | B1 | 11/2016 |
| EP | 2922501 | B1 | 11/2016 |
| EP | 2967854 | B1 | 11/2016 |
| EP | 3020365 | B1 | 11/2016 |
| EP | 3090703 | A1 | 11/2016 |
| EP | 3096713 | A1 | 11/2016 |
| EP | 1645244 | B1 | 12/2016 |
| EP | 1667614 | B1 | 12/2016 |
| EP | 1684656 | B1 | 12/2016 |
| EP | 1684670 | B1 | 12/2016 |
| EP | 1750592 | B1 | 12/2016 |
| EP | 1883375 | B1 | 12/2016 |
| EP | 2293739 | B1 | 12/2016 |
| EP | 2339988 | B1 | 12/2016 |
| EP | 2512375 | B1 | 12/2016 |
| EP | 2754417 | B1 | 12/2016 |
| EP | 2754418 | B1 | 12/2016 |
| EP | 2755562 | B1 | 12/2016 |
| EP | 2889019 | B1 | 12/2016 |
| EP | 3010442 | B1 | 12/2016 |
| EP | 3099271 | A1 | 12/2016 |
| EP | 3102150 | A1 | 12/2016 |
| EP | 3107495 | A1 | 12/2016 |
| EP | 3107498 | A2 | 12/2016 |
| EP | 3107500 | A1 | 12/2016 |
| EP | 1893127 | B1 | 1/2017 |
| EP | 1951352 | B1 | 1/2017 |
| EP | 2109419 | B1 | 1/2017 |
| EP | 2185107 | B1 | 1/2017 |
| EP | 2266503 | B1 | 1/2017 |
| EP | 2340055 | B1 | 1/2017 |
| EP | 2395941 | B1 | 1/2017 |
| EP | 2400923 | B1 | 1/2017 |
| EP | 2629699 | B1 | 1/2017 |
| EP | 2645963 | B1 | 1/2017 |
| EP | 2654622 | B1 | 1/2017 |
| EP | 2706952 | B1 | 1/2017 |
| EP | 2760347 | B1 | 1/2017 |
| EP | 2771064 | B1 | 1/2017 |
| EP | 2780077 | B1 | 1/2017 |
| EP | 2809272 | B1 | 1/2017 |
| EP | 2934385 | B1 | 1/2017 |
| EP | 2986255 | B1 | 1/2017 |
| EP | 3119351 | A1 | 1/2017 |
| EP | 1507493 | B1 | 2/2017 |
| EP | 2563238 | B1 | 2/2017 |
| EP | 2752170 | B1 | 2/2017 |
| EP | 2760371 | B1 | 2/2017 |
| EP | 2793709 | B1 | 2/2017 |
| EP | 2793748 | B1 | 2/2017 |
| EP | 2793763 | B1 | 2/2017 |
| EP | 2832317 | B1 | 2/2017 |
| EP | 2921135 | B1 | 2/2017 |
| EP | 2967931 | B1 | 2/2017 |
| EP | 2974693 | B1 | 2/2017 |
| EP | 3025680 | B1 | 2/2017 |
| EP | 3025681 | B1 | 2/2017 |
| EP | 3125826 | A1 | 2/2017 |
| EP | 3125827 | A2 | 2/2017 |
| EP | 3128927 | A1 | 2/2017 |
| EP | 3131502 | A1 | 2/2017 |
| EP | 1845895 | B1 | 3/2017 |
| EP | 2190385 | B1 | 3/2017 |
| EP | 2266504 | B1 | 3/2017 |
| EP | 2341871 | B1 | 3/2017 |
| EP | 2379011 | B1 | 3/2017 |
| EP | 2379013 | B1 | 3/2017 |
| EP | 2640316 | B1 | 3/2017 |
| EP | 2731552 | B1 | 3/2017 |
| EP | 2756109 | B1 | 3/2017 |
| EP | 2773298 | B1 | 3/2017 |
| EP | 2832316 | B1 | 3/2017 |
| EP | 2854718 | B1 | 3/2017 |
| EP | 2881083 | B1 | 3/2017 |
| EP | 2934390 | B1 | 3/2017 |
| EP | 2934391 | B1 | 3/2017 |
| EP | 3010564 | A4 | 3/2017 |
| EP | 3145451 | A2 | 3/2017 |
| EP | 3146938 | A1 | 3/2017 |
| EP | 2014239 | B1 | 4/2017 |
| EP | 2111189 | B1 | 4/2017 |
| EP | 2393451 | B1 | 4/2017 |
| EP | 2617388 | B1 | 4/2017 |
| EP | 2629700 | B1 | 4/2017 |
| EP | 2832318 | B1 | 4/2017 |
| EP | 2893904 | B1 | 4/2017 |
| EP | 2982340 | B1 | 4/2017 |
| EP | 3000436 | B1 | 4/2017 |
| EP | 3001979 | B1 | 4/2017 |
| EP | 3043749 | B1 | 4/2017 |
| EP | 3045147 | B1 | 4/2017 |
| EP | 3054893 | B1 | 4/2017 |
| EP | 3154474 | A1 | 4/2017 |
| EP | 3156007 | A1 | 4/2017 |
| EP | 3157469 | A1 | 4/2017 |
| EP | 3158975 | A1 | 4/2017 |
| EP | 1809270 | B1 | 5/2017 |
| EP | 1855614 | B1 | 5/2017 |
| EP | 2001402 | B1 | 5/2017 |
| EP | 2032080 | B1 | 5/2017 |
| EP | 2262451 | B1 | 5/2017 |
| EP | 2470119 | B1 | 5/2017 |
| EP | 2478869 | B1 | 5/2017 |
| EP | 2538880 | B1 | 5/2017 |
| EP | 2545850 | B1 | 5/2017 |
| EP | 2600799 | B1 | 5/2017 |
| EP | 2717926 | B1 | 5/2017 |
| EP | 2726024 | B1 | 5/2017 |
| EP | 2805678 | B1 | 5/2017 |
| EP | 2918245 | B1 | 5/2017 |
| EP | 2953579 | B1 | 5/2017 |
| EP | 2976043 | B1 | 5/2017 |
| EP | 2979666 | B1 | 5/2017 |
| EP | 3011931 | B1 | 5/2017 |
| EP | 3025682 | B1 | 5/2017 |
| EP | 3033135 | B1 | 5/2017 |
| EP | 3160396 | A1 | 5/2017 |
| EP | 3167847 | A1 | 5/2017 |
| EP | 3169245 | A1 | 5/2017 |
| EP | 3169276 | A1 | 5/2017 |
| EP | 2351541 | B1 | 6/2017 |
| EP | 2384165 | B1 | 6/2017 |
| EP | 2400924 | B1 | 6/2017 |
| EP | 2419041 | B1 | 6/2017 |
| EP | 2419050 | B1 | 6/2017 |
| EP | 2489331 | B1 | 6/2017 |
| EP | 2493417 | B1 | 6/2017 |
| EP | 2560585 | B1 | 6/2017 |
| EP | 2611387 | B1 | 6/2017 |
| EP | 2645967 | B1 | 6/2017 |
| EP | 2677965 | B1 | 6/2017 |
| EP | 2760349 | B1 | 6/2017 |
| EP | 2826443 | B1 | 6/2017 |
| EP | 2906148 | B1 | 6/2017 |
| EP | 2929860 | B1 | 6/2017 |
| EP | 2934669 | B1 | 6/2017 |
| EP | 2967852 | B1 | 6/2017 |
| EP | 3076901 | A4 | 6/2017 |
| EP | 3174502 | A1 | 6/2017 |
| EP | 3175823 | A1 | 6/2017 |
| EP | 3178443 | A1 | 6/2017 |
| EP | 3178445 | A1 | 6/2017 |

(56) References Cited

FOREIGN PATENT DOCUMENTS

| | | |
|---|---|---|
| EP | 3184081 A1 | 6/2017 |
| EP | 1624810 B1 | 7/2017 |
| EP | 2026703 B1 | 7/2017 |
| EP | 2293718 B1 | 7/2017 |
| EP | 2339989 B1 | 7/2017 |
| EP | 2344076 B1 | 7/2017 |
| EP | 2486893 B1 | 7/2017 |
| EP | 2536356 B1 | 7/2017 |
| EP | 2548534 B1 | 7/2017 |
| EP | 2608742 B1 | 7/2017 |
| EP | 2673038 B1 | 7/2017 |
| EP | 2676638 B1 | 7/2017 |
| EP | 2774630 B1 | 7/2017 |
| EP | 2825107 B1 | 7/2017 |
| EP | 2841020 B1 | 7/2017 |
| EP | 2934386 B1 | 7/2017 |
| EP | 2943151 B1 | 7/2017 |
| EP | 3058894 B1 | 7/2017 |
| EP | 3071151 B1 | 7/2017 |
| EP | 3191025 A1 | 7/2017 |
| EP | 3193740 A2 | 7/2017 |
| EP | 3193782 A1 | 7/2017 |
| EP | 1530441 B1 | 8/2017 |
| EP | 1722716 B1 | 8/2017 |
| EP | 1971289 B1 | 8/2017 |
| EP | 2323591 B1 | 8/2017 |
| EP | 2344070 B1 | 8/2017 |
| EP | 2393442 A4 | 8/2017 |
| EP | 2413842 B1 | 8/2017 |
| EP | 2427143 B1 | 8/2017 |
| EP | 2459077 B1 | 8/2017 |
| EP | 2480167 B1 | 8/2017 |
| EP | 2482749 B1 | 8/2017 |
| EP | 2496181 B1 | 8/2017 |
| EP | 2568925 B1 | 8/2017 |
| EP | 2617389 B1 | 8/2017 |
| EP | 2713954 B1 | 8/2017 |
| EP | 2755602 B1 | 8/2017 |
| EP | 2800602 B1 | 8/2017 |
| EP | 2809263 B1 | 8/2017 |
| EP | 2830536 B1 | 8/2017 |
| EP | 2841009 B1 | 8/2017 |
| EP | 2844190 B1 | 8/2017 |
| EP | 2849681 B1 | 8/2017 |
| EP | 2858600 B1 | 8/2017 |
| EP | 2897556 B1 | 8/2017 |
| EP | 2934388 B1 | 8/2017 |
| EP | 2979667 B1 | 8/2017 |
| EP | 3197397 A1 | 8/2017 |
| EP | 3202371 A1 | 8/2017 |
| EP | 3206629 A1 | 8/2017 |
| EP | 3206631 A2 | 8/2017 |
| EP | 1799093 B1 | 9/2017 |
| EP | 2010103 B1 | 9/2017 |
| EP | 2114304 B1 | 9/2017 |
| EP | 2344090 B1 | 9/2017 |
| EP | 2398421 B1 | 9/2017 |
| EP | 2437687 B1 | 9/2017 |
| EP | 2453970 B1 | 9/2017 |
| EP | 2509538 B1 | 9/2017 |
| EP | 2713956 B1 | 9/2017 |
| EP | 2772227 B1 | 9/2017 |
| EP | 2787924 B1 | 9/2017 |
| EP | 2803335 B1 | 9/2017 |
| EP | 2811939 B1 | 9/2017 |
| EP | 2830537 B1 | 9/2017 |
| EP | 2865355 B1 | 9/2017 |
| EP | 2872047 B1 | 9/2017 |
| EP | 2934389 B1 | 9/2017 |
| EP | 3213715 A1 | 9/2017 |
| EP | 3213716 A1 | 9/2017 |
| EP | 3215061 A1 | 9/2017 |
| EP | 3220856 A2 | 9/2017 |
| EP | 3220857 A1 | 9/2017 |
| EP | 1945141 B1 | 10/2017 |
| EP | 2317956 B1 | 10/2017 |
| EP | 2613737 B1 | 10/2017 |
| EP | 2620125 B1 | 10/2017 |
| EP | 2720642 B1 | 10/2017 |
| EP | 2741682 B1 | 10/2017 |
| EP | 2872077 B1 | 10/2017 |
| EP | 3021925 B1 | 10/2017 |
| EP | 3231395 A1 | 10/2017 |
| EP | 3232989 A1 | 10/2017 |
| EP | 1651148 B1 | 11/2017 |
| EP | 1913901 B1 | 11/2017 |
| EP | 2222248 B1 | 11/2017 |
| EP | 2296581 B1 | 11/2017 |
| EP | 2326264 B1 | 11/2017 |
| EP | 2427142 B1 | 11/2017 |
| EP | 2456483 B1 | 11/2017 |
| EP | 2493423 B1 | 11/2017 |
| EP | 2611391 B1 | 11/2017 |
| EP | 2618780 B1 | 11/2017 |
| EP | 2658480 B1 | 11/2017 |
| EP | 2710978 B1 | 11/2017 |
| EP | 2832315 B1 | 11/2017 |
| EP | 2954875 B1 | 11/2017 |
| EP | 2967861 B1 | 11/2017 |
| EP | 2982338 B1 | 11/2017 |
| EP | 3027144 B1 | 11/2017 |
| EP | 3043746 B1 | 11/2017 |
| EP | 3049026 B1 | 11/2017 |
| EP | 3068311 B1 | 11/2017 |
| EP | 3110368 B1 | 11/2017 |
| EP | 3110369 B1 | 11/2017 |
| EP | 3132773 B1 | 11/2017 |
| EP | 3238662 A1 | 11/2017 |
| EP | 3245980 A1 | 11/2017 |
| EP | 3247312 A1 | 11/2017 |
| EP | 1667603 B1 | 12/2017 |
| EP | 1670351 A4 | 12/2017 |
| EP | 1874954 B1 | 12/2017 |
| EP | 2427145 B1 | 12/2017 |
| EP | 2542185 B1 | 12/2017 |
| EP | 2723274 B1 | 12/2017 |
| EP | 2736455 B1 | 12/2017 |
| EP | 2736457 B1 | 12/2017 |
| EP | 2830534 B1 | 12/2017 |
| EP | 2830535 B1 | 12/2017 |
| EP | 2911592 B1 | 12/2017 |
| EP | 2916772 B1 | 12/2017 |
| EP | 2967922 B1 | 12/2017 |
| EP | 3009105 B1 | 12/2017 |
| EP | 3088037 B1 | 12/2017 |
| EP | 3115023 B1 | 12/2017 |
| EP | 3251633 A1 | 12/2017 |
| EP | 3253332 A2 | 12/2017 |
| EP | 3256073 A1 | 12/2017 |
| EP | 3256074 A1 | 12/2017 |
| EP | 3256076 A1 | 12/2017 |
| EP | 3256178 A1 | 12/2017 |
| EP | 1492458 B1 | 1/2018 |
| EP | 1768604 B1 | 1/2018 |
| EP | 1951154 B1 | 1/2018 |
| EP | 2091465 B1 | 1/2018 |
| EP | 2345380 B1 | 1/2018 |
| EP | 2456363 B1 | 1/2018 |
| EP | 2531143 B1 | 1/2018 |
| EP | 2621407 B1 | 1/2018 |
| EP | 2694123 B1 | 1/2018 |
| EP | 2775962 B1 | 1/2018 |
| EP | 2874568 B1 | 1/2018 |
| EP | 2967863 B1 | 1/2018 |
| EP | 2967869 B1 | 1/2018 |
| EP | 3033047 B1 | 1/2018 |
| EP | 3037065 B1 | 1/2018 |
| EP | 3049025 B1 | 1/2018 |
| EP | 3052052 B1 | 1/2018 |
| EP | 3078350 B1 | 1/2018 |
| EP | 3266417 A1 | 1/2018 |
| EP | 3267946 A1 | 1/2018 |
| EP | 3269331 A1 | 1/2018 |
| EP | 3273911 A1 | 1/2018 |

(56) References Cited

FOREIGN PATENT DOCUMENTS

| | | |
|---|---|---|
| EP | 3275404 A1 | 1/2018 |
| EP | 2197512 B1 | 2/2018 |
| EP | 2248486 B1 | 2/2018 |
| EP | 2344066 B1 | 2/2018 |
| EP | 2381854 B1 | 2/2018 |
| EP | 2667823 B1 | 2/2018 |
| EP | 2699169 B1 | 2/2018 |
| EP | 2714177 B1 | 2/2018 |
| EP | 2736544 B1 | 2/2018 |
| EP | 2846736 B1 | 2/2018 |
| EP | 2886082 B1 | 2/2018 |
| EP | 2886084 B1 | 2/2018 |
| EP | 2931178 B1 | 2/2018 |
| EP | 2934392 B1 | 2/2018 |
| EP | 3150173 B1 | 2/2018 |
| EP | 3277221 A1 | 2/2018 |
| EP | 3277222 A1 | 2/2018 |
| EP | 3280358 A1 | 2/2018 |
| EP | 3281608 A1 | 2/2018 |
| EP | 3283009 A1 | 2/2018 |
| EP | 3283011 A1 | 2/2018 |
| EP | 3287099 A1 | 2/2018 |
| EP | 1959864 B1 | 3/2018 |
| EP | 2513200 B1 | 3/2018 |
| EP | 2608815 B1 | 3/2018 |
| EP | 2858711 B1 | 3/2018 |
| EP | 2938292 B1 | 3/2018 |
| EP | 2943132 B1 | 3/2018 |
| EP | 2983620 B1 | 3/2018 |
| EP | 3003219 B1 | 3/2018 |
| EP | 3005979 B1 | 3/2018 |
| EP | 3037064 B1 | 3/2018 |
| EP | 3046511 B1 | 3/2018 |
| EP | 3142603 B1 | 3/2018 |
| EP | 3288479 A1 | 3/2018 |
| EP | 3288491 A1 | 3/2018 |
| EP | 3288494 A1 | 3/2018 |
| EP | 3288497 A2 | 3/2018 |
| EP | 3288498 A1 | 3/2018 |
| EP | 3288499 A1 | 3/2018 |
| EP | 3290004 A1 | 3/2018 |
| EP | 3290007 A1 | 3/2018 |
| EP | 3294214 A1 | 3/2018 |
| EP | 3294215 A1 | 3/2018 |
| EP | 3294218 A1 | 3/2018 |
| EP | 3296979 A1 | 3/2018 |
| EP | 3298970 A1 | 3/2018 |
| EP | 3298987 A1 | 3/2018 |
| EP | 3298988 A1 | 3/2018 |
| EP | 2209440 B1 | 4/2018 |
| EP | 2536357 B1 | 4/2018 |
| EP | 2605725 B1 | 4/2018 |
| EP | 2608743 B1 | 4/2018 |
| EP | 2709561 B1 | 4/2018 |
| EP | 2787925 B1 | 4/2018 |
| EP | 2789314 B1 | 4/2018 |
| EP | 2900150 B1 | 4/2018 |
| EP | 2908779 B1 | 4/2018 |
| EP | 2922502 B1 | 4/2018 |
| EP | 2964441 B1 | 4/2018 |
| EP | 2967868 B1 | 4/2018 |
| EP | 2979665 B1 | 4/2018 |
| EP | 2994073 B1 | 4/2018 |
| EP | 3095394 B1 | 4/2018 |
| EP | 3128927 A4 | 4/2018 |
| EP | 3134033 B1 | 4/2018 |
| EP | 3137146 A4 | 4/2018 |
| EP | 3280482 A4 | 4/2018 |
| EP | 3302297 A2 | 4/2018 |
| EP | 3302362 A1 | 4/2018 |
| EP | 3302367 A1 | 4/2018 |
| EP | 3307208 A1 | 4/2018 |
| EP | 3308745 A1 | 4/2018 |
| EP | 3310301 A1 | 4/2018 |
| EP | 3311774 A1 | 4/2018 |
| EP | 3311775 A1 | 4/2018 |
| EP | 3311783 A1 | 4/2018 |
| EP | 1945112 B1 | 5/2018 |
| EP | 2007313 B1 | 5/2018 |
| EP | 2316381 B2 | 5/2018 |
| EP | 2377469 B1 | 5/2018 |
| EP | 2531115 B1 | 5/2018 |
| EP | 2561831 B1 | 5/2018 |
| EP | 2605724 B1 | 5/2018 |
| EP | 2723277 B1 | 5/2018 |
| EP | 2741711 B1 | 5/2018 |
| EP | 2755573 B1 | 5/2018 |
| EP | 2768429 B1 | 5/2018 |
| EP | 2819618 B1 | 5/2018 |
| EP | 2833836 B1 | 5/2018 |
| EP | 2886083 B1 | 5/2018 |
| EP | 2926840 B1 | 5/2018 |
| EP | 2943157 B1 | 5/2018 |
| EP | 2948099 B1 | 5/2018 |
| EP | 3000437 B1 | 5/2018 |
| EP | 3145448 B1 | 5/2018 |
| EP | 3154475 B1 | 5/2018 |
| EP | 3316819 A1 | 5/2018 |
| EP | 3316821 A1 | 5/2018 |
| EP | 3322381 A1 | 5/2018 |
| EP | 3322383 A1 | 5/2018 |
| EP | 3323353 A1 | 5/2018 |
| EP | 3323439 A1 | 5/2018 |
| EP | 3324892 A1 | 5/2018 |
| EP | 3326584 A1 | 5/2018 |
| EP | 2150312 B1 | 6/2018 |
| EP | 2379322 B1 | 6/2018 |
| EP | 2400925 B1 | 6/2018 |
| EP | 2552355 B1 | 6/2018 |
| EP | 2560589 B1 | 6/2018 |
| EP | 2661305 B1 | 6/2018 |
| EP | 2736456 B1 | 6/2018 |
| EP | 2782523 B1 | 6/2018 |
| EP | 3056170 B1 | 6/2018 |
| EP | 3062745 B1 | 6/2018 |
| EP | 3130320 B1 | 6/2018 |
| EP | 3187150 B1 | 6/2018 |
| EP | 3334378 A1 | 6/2018 |
| EP | 3334380 A1 | 6/2018 |
| EP | 3334381 A1 | 6/2018 |
| EP | 3335670 A1 | 6/2018 |
| EP | 3337412 A1 | 6/2018 |
| EP | 3337424 A1 | 6/2018 |
| EP | 2479872 B1 | 7/2018 |
| EP | 2563277 B1 | 7/2018 |
| EP | 2563278 B1 | 7/2018 |
| EP | 2616004 B1 | 7/2018 |
| EP | 2779943 B1 | 7/2018 |
| EP | 2802290 B1 | 7/2018 |
| EP | 2816980 B1 | 7/2018 |
| EP | 2938293 B1 | 7/2018 |
| EP | 3107496 B1 | 7/2018 |
| EP | 3178450 B1 | 7/2018 |
| EP | 3212097 B1 | 7/2018 |
| EP | 3340923 A1 | 7/2018 |
| EP | 3340932 A1 | 7/2018 |
| EP | 3340934 A1 | 7/2018 |
| EP | 3340936 A1 | 7/2018 |
| EP | 3340945 A1 | 7/2018 |
| EP | 3342355 A1 | 7/2018 |
| EP | 3342377 A1 | 7/2018 |
| EP | 3344158 A1 | 7/2018 |
| EP | 3346952 A1 | 7/2018 |
| EP | 3347182 A1 | 7/2018 |
| EP | 3348235 A1 | 7/2018 |
| EP | 3349693 A1 | 7/2018 |
| EP | 2536354 B1 | 8/2018 |
| EP | 2616006 B1 | 8/2018 |
| EP | 2797556 B1 | 8/2018 |
| EP | 2822473 B1 | 8/2018 |
| EP | 2854711 B1 | 8/2018 |
| EP | 2866847 B1 | 8/2018 |
| EP | 2918246 B1 | 8/2018 |
| EP | 2967845 B1 | 8/2018 |

(56) References Cited

FOREIGN PATENT DOCUMENTS

| | | | |
|---|---|---|---|
| EP | 2999436 | B1 | 8/2018 |
| EP | 3013281 | B1 | 8/2018 |
| EP | 3060170 | B1 | 8/2018 |
| EP | 3104811 | B1 | 8/2018 |
| EP | 3143944 | B1 | 8/2018 |
| EP | 3157467 | B1 | 8/2018 |
| EP | 3193791 | B1 | 8/2018 |
| EP | 3241526 | B1 | 8/2018 |
| EP | 3355800 | A1 | 8/2018 |
| EP | 3360513 | A1 | 8/2018 |
| EP | 3360514 | A1 | 8/2018 |
| EP | 3361988 | A1 | 8/2018 |
| EP | 3361991 | A1 | 8/2018 |
| EP | 2114305 | B1 | 9/2018 |
| EP | 2155115 | B1 | 9/2018 |
| EP | 2601910 | B1 | 9/2018 |
| EP | 2617390 | B1 | 9/2018 |
| EP | 2734157 | B1 | 9/2018 |
| EP | 2968674 | B1 | 9/2018 |
| EP | 2999415 | B1 | 9/2018 |
| EP | 3106130 | B1 | 9/2018 |
| EP | 3151763 | B1 | 9/2018 |
| EP | 3213717 | B1 | 9/2018 |
| EP | 3245985 | B1 | 9/2018 |
| EP | 3367979 | A1 | 9/2018 |
| EP | 3370649 | A1 | 9/2018 |
| EP | 3370650 | A1 | 9/2018 |
| EP | 3377000 | A1 | 9/2018 |
| EP | 1827256 | B1 | 10/2018 |
| EP | 1850790 | B1 | 10/2018 |
| EP | 2063823 | B1 | 10/2018 |
| EP | 2124825 | B1 | 10/2018 |
| EP | 2249746 | B1 | 10/2018 |
| EP | 2254514 | B1 | 10/2018 |
| EP | 2285309 | B1 | 10/2018 |
| EP | 2455042 | B1 | 10/2018 |
| EP | 2571561 | B1 | 10/2018 |
| EP | 2616008 | B1 | 10/2018 |
| EP | 2647393 | B1 | 10/2018 |
| EP | 2739214 | B1 | 10/2018 |
| EP | 2739247 | B1 | 10/2018 |
| EP | 2776114 | B1 | 10/2018 |
| EP | 2836171 | B1 | 10/2018 |
| EP | 2842581 | B1 | 10/2018 |
| EP | 2870946 | B1 | 10/2018 |
| EP | 2923665 | B1 | 10/2018 |
| EP | 2964277 | B1 | 10/2018 |
| EP | 3001978 | B1 | 10/2018 |
| EP | 3010562 | B1 | 10/2018 |
| EP | 3072475 | B1 | 10/2018 |
| EP | 3081161 | B1 | 10/2018 |
| EP | 3081195 | B1 | 10/2018 |
| EP | 3099345 | B1 | 10/2018 |
| EP | 3120809 | B1 | 10/2018 |
| EP | 3238663 | B1 | 10/2018 |
| EP | 3275404 | A4 | 10/2018 |
| EP | 3384879 | A1 | 10/2018 |
| EP | 3388027 | A1 | 10/2018 |
| EP | 3389557 | A1 | 10/2018 |
| EP | 3390706 | A1 | 10/2018 |
| EP | 1708650 | B1 | 11/2018 |
| EP | 1945143 | B1 | 11/2018 |
| EP | 2205183 | B1 | 11/2018 |
| EP | 2663258 | B1 | 11/2018 |
| EP | 2790615 | B1 | 11/2018 |
| EP | 2854709 | B1 | 11/2018 |
| EP | 2898859 | B1 | 11/2018 |
| EP | 2921139 | B1 | 11/2018 |
| EP | 2928538 | B1 | 11/2018 |
| EP | 3075354 | B1 | 11/2018 |
| EP | 3082949 | B1 | 11/2018 |
| EP | 3145452 | B1 | 11/2018 |
| EP | 3216424 | B1 | 11/2018 |
| EP | 3260084 | B1 | 11/2018 |
| EP | 3397206 | A1 | 11/2018 |
| EP | 3398562 | A1 | 11/2018 |
| EP | 3400908 | A1 | 11/2018 |
| EP | 3403616 | A1 | 11/2018 |
| EP | 3405139 | A1 | 11/2018 |
| EP | 1858450 | B1 | 12/2018 |
| EP | 2150208 | B1 | 12/2018 |
| EP | 2326261 | B1 | 12/2018 |
| EP | 2344075 | B1 | 12/2018 |
| EP | 2370028 | B1 | 12/2018 |
| EP | 2555709 | B1 | 12/2018 |
| EP | 2564812 | B1 | 12/2018 |
| EP | 2777618 | B1 | 12/2018 |
| EP | 2814427 | B1 | 12/2018 |
| EP | 2829240 | B1 | 12/2018 |
| EP | 2911594 | B1 | 12/2018 |
| EP | 2911729 | B1 | 12/2018 |
| EP | 2954876 | B1 | 12/2018 |
| EP | 2958520 | B1 | 12/2018 |
| EP | 2958605 | B1 | 12/2018 |
| EP | 3010446 | B1 | 12/2018 |
| EP | 3064174 | B1 | 12/2018 |
| EP | 3206628 | B1 | 12/2018 |
| EP | 3242629 | B1 | 12/2018 |
| EP | 3260085 | B1 | 12/2018 |
| EP | 3266416 | B1 | 12/2018 |
| EP | 3326583 | B1 | 12/2018 |
| EP | 3407834 | A1 | 12/2018 |
| EP | 3410984 | A1 | 12/2018 |
| EP | 3410987 | A1 | 12/2018 |
| EP | 3415120 | A1 | 12/2018 |
| EP | 3417813 | A1 | 12/2018 |
| EP | 2129332 | B1 | 1/2019 |
| EP | 2196159 | B1 | 1/2019 |
| EP | 2370025 | B1 | 1/2019 |
| EP | 2549957 | B1 | 1/2019 |
| EP | 2819619 | B1 | 1/2019 |
| EP | 2849680 | B1 | 1/2019 |
| EP | 2856972 | B1 | 1/2019 |
| EP | 2866742 | B1 | 1/2019 |
| EP | 2884946 | B1 | 1/2019 |
| EP | 2948102 | B1 | 1/2019 |
| EP | 2979664 | B1 | 1/2019 |
| EP | 3043748 | B1 | 1/2019 |
| EP | 3145449 | B1 | 1/2019 |
| EP | 3288491 | A4 | 1/2019 |
| EP | 3332743 | B1 | 1/2019 |
| EP | 3427695 | A1 | 1/2019 |
| EP | 3429507 | A1 | 1/2019 |
| EP | 3432832 | A1 | 1/2019 |
| EP | 3432834 | A1 | 1/2019 |
| EP | 1895943 | B1 | 2/2019 |
| EP | 2070490 | B1 | 2/2019 |
| EP | 2308425 | B1 | 2/2019 |
| EP | 2379009 | B1 | 2/2019 |
| EP | 2575685 | B1 | 2/2019 |
| EP | 2688562 | B1 | 2/2019 |
| EP | 2714068 | B1 | 2/2019 |
| EP | 2720641 | B1 | 2/2019 |
| EP | 2760375 | B1 | 2/2019 |
| EP | 2862590 | B1 | 2/2019 |
| EP | 2925259 | B1 | 2/2019 |
| EP | 2931179 | B1 | 2/2019 |
| EP | 3005983 | B1 | 2/2019 |
| EP | 3023117 | B1 | 2/2019 |
| EP | 3184083 | B1 | 2/2019 |
| EP | 3202333 | B1 | 2/2019 |
| EP | 3261583 | B1 | 2/2019 |
| EP | 3278832 | B1 | 2/2019 |
| EP | 3409454 | A4 | 2/2019 |
| EP | 3435919 | A1 | 2/2019 |
| EP | 3441045 | A1 | 2/2019 |
| EP | 3442469 | A1 | 2/2019 |
| EP | 3443937 | A1 | 2/2019 |
| EP | 3445290 | A1 | 2/2019 |
| EP | 1771132 | B1 | 3/2019 |
| EP | 1959866 | B1 | 3/2019 |
| EP | 2120794 | B1 | 3/2019 |
| EP | 2259728 | B1 | 3/2019 |
| EP | 2344074 | B1 | 3/2019 |

(56) References Cited

FOREIGN PATENT DOCUMENTS

| | | | |
|---|---|---|---|
| EP | 2552356 B1 | 3/2019 |
| EP | 2598044 B1 | 3/2019 |
| EP | 2659861 B1 | 3/2019 |
| EP | 2670357 B1 | 3/2019 |
| EP | 2898902 B1 | 3/2019 |
| EP | 2948098 B1 | 3/2019 |
| EP | 2948101 B1 | 3/2019 |
| EP | 2967865 B1 | 3/2019 |
| EP | 2974695 B1 | 3/2019 |
| EP | 3027243 B1 | 3/2019 |
| EP | 3116446 B1 | 3/2019 |
| EP | 3145445 B1 | 3/2019 |
| EP | 3151783 B1 | 3/2019 |
| EP | 3151784 B1 | 3/2019 |
| EP | 3278768 B1 | 3/2019 |
| EP | 3320943 B1 | 3/2019 |
| EP | 3448314 A1 | 3/2019 |
| EP | 3448315 A1 | 3/2019 |
| EP | 3449969 A1 | 3/2019 |
| EP | 3454785 A1 | 3/2019 |
| EP | 3454786 A1 | 3/2019 |
| EP | 3454789 A1 | 3/2019 |
| EP | 3454794 A1 | 3/2019 |
| EP | 3454795 A1 | 3/2019 |
| EP | 3457987 A1 | 3/2019 |
| EP | 3457988 A1 | 3/2019 |
| EP | 3457990 A1 | 3/2019 |
| EP | 3458136 A2 | 3/2019 |
| EP | 3459499 A2 | 3/2019 |
| EP | 1793745 B1 | 4/2019 |
| EP | 1855623 B1 | 4/2019 |
| EP | 2129333 B1 | 4/2019 |
| EP | 2149349 B1 | 4/2019 |
| EP | 2438888 B1 | 4/2019 |
| EP | 2484309 B1 | 4/2019 |
| EP | 2519268 B1 | 4/2019 |
| EP | 2528545 B1 | 4/2019 |
| EP | 2536358 B1 | 4/2019 |
| EP | 2661239 B1 | 4/2019 |
| EP | 2709563 B1 | 4/2019 |
| EP | 2736451 B1 | 4/2019 |
| EP | 2810619 B1 | 4/2019 |
| EP | 2810622 B1 | 4/2019 |
| EP | 2879589 B1 | 4/2019 |
| EP | 2921198 B1 | 4/2019 |
| EP | 2986256 B1 | 4/2019 |
| EP | 3090704 B1 | 4/2019 |
| EP | 3116445 B1 | 4/2019 |
| EP | 3141217 B1 | 4/2019 |
| EP | 3193745 B1 | 4/2019 |
| EP | 3241525 B1 | 4/2019 |
| EP | 3344167 A4 | 4/2019 |
| EP | 3461531 A1 | 4/2019 |
| EP | 3463120 A1 | 4/2019 |
| EP | 3466373 A1 | 4/2019 |
| EP | 3471662 A1 | 4/2019 |
| EP | 1703870 B1 | 5/2019 |
| EP | 1708642 B1 | 5/2019 |
| EP | 2240121 B1 | 5/2019 |
| EP | 2663259 B1 | 5/2019 |
| EP | 2695586 B1 | 5/2019 |
| EP | 2726018 B1 | 5/2019 |
| EP | 2954872 B1 | 5/2019 |
| EP | 3071150 B1 | 5/2019 |
| EP | 3110370 B1 | 5/2019 |
| EP | 3111890 B1 | 5/2019 |
| EP | 3182932 B1 | 5/2019 |
| EP | 3192472 B1 | 5/2019 |
| EP | 3238661 B1 | 5/2019 |
| EP | 3284503 B1 | 5/2019 |
| EP | 3302364 B1 | 5/2019 |
| EP | 3315094 B1 | 5/2019 |
| EP | 3316818 B1 | 5/2019 |
| EP | 3474778 A1 | 5/2019 |
| EP | 3476366 A1 | 5/2019 |
| EP | 3476424 A1 | 5/2019 |
| EP | 3478224 A1 | 5/2019 |
| EP | 3479797 A1 | 5/2019 |
| EP | 3481335 A1 | 5/2019 |
| EP | 3481336 A1 | 5/2019 |
| EP | 3481338 A1 | 5/2019 |
| EP | 3481339 A1 | 5/2019 |
| EP | 3482718 A1 | 5/2019 |
| EP | 3484412 A1 | 5/2019 |
| EP | 3485847 A1 | 5/2019 |
| EP | 3485848 A1 | 5/2019 |
| EP | 3485933 A1 | 5/2019 |
| EP | 3487420 A1 | 5/2019 |
| EP | 3487451 A1 | 5/2019 |
| EP | 3487452 A1 | 5/2019 |
| EP | 3488822 A1 | 5/2019 |
| EP | 1624792 B1 | 6/2019 |
| EP | 1737394 B1 | 6/2019 |
| EP | 1858451 B1 | 6/2019 |
| EP | 1895944 B1 | 6/2019 |
| EP | 1968487 B1 | 6/2019 |
| EP | 2004095 B1 | 6/2019 |
| EP | 2010102 B1 | 6/2019 |
| EP | 2131788 B1 | 6/2019 |
| EP | 2560580 B1 | 6/2019 |
| EP | 2618782 B1 | 6/2019 |
| EP | 2868296 B1 | 6/2019 |
| EP | 2961358 B1 | 6/2019 |
| EP | 2967847 B1 | 6/2019 |
| EP | 2985006 B1 | 6/2019 |
| EP | 3033048 B1 | 6/2019 |
| EP | 3119451 B1 | 6/2019 |
| EP | 3131503 B1 | 6/2019 |
| EP | 3213718 B1 | 6/2019 |
| EP | 3275390 B1 | 6/2019 |
| EP | 3300692 B1 | 6/2019 |
| EP | 3326585 B1 | 6/2019 |
| EP | 3338737 B1 | 6/2019 |
| EP | 3357457 B1 | 6/2019 |
| EP | 3372198 B1 | 6/2019 |
| EP | 3490465 A1 | 6/2019 |
| EP | 3490500 A1 | 6/2019 |
| EP | 3490657 A1 | 6/2019 |
| EP | 3490659 A1 | 6/2019 |
| EP | 3496626 A1 | 6/2019 |
| EP | 3496664 A1 | 6/2019 |
| EP | 3498224 A1 | 6/2019 |
| EP | 1659981 B1 | 7/2019 |
| EP | 1924223 B1 | 7/2019 |
| EP | 2249745 B1 | 7/2019 |
| EP | 2296744 B1 | 7/2019 |
| EP | 2331019 B1 | 7/2019 |
| EP | 2368527 B1 | 7/2019 |
| EP | 2509542 B1 | 7/2019 |
| EP | 2555710 B1 | 7/2019 |
| EP | 2575682 B1 | 7/2019 |
| EP | 2575683 B1 | 7/2019 |
| EP | 2640431 B1 | 7/2019 |
| EP | 2641572 B1 | 7/2019 |
| EP | 2649964 B1 | 7/2019 |
| EP | 2767260 B1 | 7/2019 |
| EP | 2777615 B1 | 7/2019 |
| EP | 2838476 B1 | 7/2019 |
| EP | 2861186 B1 | 7/2019 |
| EP | 2877124 B1 | 7/2019 |
| EP | 2877132 B1 | 7/2019 |
| EP | 2921565 B1 | 7/2019 |
| EP | 2938291 B1 | 7/2019 |
| EP | 2999433 B1 | 7/2019 |
| EP | 3145450 B1 | 7/2019 |
| EP | 3254644 B1 | 7/2019 |
| EP | 3315093 B1 | 7/2019 |
| EP | 3344189 B1 | 7/2019 |
| EP | 3503813 A1 | 7/2019 |
| EP | 3503846 A1 | 7/2019 |
| EP | 3503847 A1 | 7/2019 |
| EP | 3503848 A1 | 7/2019 |
| EP | 3505077 A1 | 7/2019 |
| EP | 3512465 A1 | 7/2019 |

(56) References Cited

FOREIGN PATENT DOCUMENTS

| | | |
|---|---|---|
| EP | 3515365 A1 | 7/2019 |
| EP | 3517075 A1 | 7/2019 |
| EP | 1861043 B1 | 8/2019 |
| EP | 2303190 B1 | 8/2019 |
| EP | 2593171 B1 | 8/2019 |
| EP | 2632393 B1 | 8/2019 |
| EP | 2663355 B1 | 8/2019 |
| EP | 2665509 B1 | 8/2019 |
| EP | 2688525 B1 | 8/2019 |
| EP | 2699201 B1 | 8/2019 |
| EP | 2755564 B1 | 8/2019 |
| EP | 2769681 B1 | 8/2019 |
| EP | 2793751 B1 | 8/2019 |
| EP | 2900177 B1 | 8/2019 |
| EP | 2967536 B1 | 8/2019 |
| EP | 3050541 B1 | 8/2019 |
| EP | 3102152 B1 | 8/2019 |
| EP | 3157607 B1 | 8/2019 |
| EP | 3231392 B1 | 8/2019 |
| EP | 3284411 B1 | 8/2019 |
| EP | 3328318 B1 | 8/2019 |
| EP | 3348233 B1 | 8/2019 |
| EP | 3366262 B1 | 8/2019 |
| EP | 3527170 A1 | 8/2019 |
| EP | 3530236 A1 | 8/2019 |
| EP | 2358297 B1 | 9/2019 |
| EP | 2368525 B1 | 9/2019 |
| EP | 2542186 B1 | 9/2019 |
| EP | 2656863 B1 | 9/2019 |
| EP | 3003221 B1 | 9/2019 |
| EP | 3003452 B1 | 9/2019 |
| EP | 3220971 B1 | 9/2019 |
| EP | 3223874 B1 | 9/2019 |
| EP | 3288495 B1 | 9/2019 |
| EP | 3311776 B1 | 9/2019 |
| EP | 3334379 B1 | 9/2019 |
| EP | 3501454 A1 | 9/2019 |
| EP | 3531975 A1 | 9/2019 |
| EP | 3534840 A1 | 9/2019 |
| EP | 3534841 A1 | 9/2019 |
| EP | 3534845 A2 | 9/2019 |
| EP | 3535010 A1 | 9/2019 |
| EP | 3538026 A1 | 9/2019 |
| EP | 3538027 A1 | 9/2019 |
| EP | 3539508 A1 | 9/2019 |
| EP | 3539509 A1 | 9/2019 |
| EP | 3541316 A1 | 9/2019 |
| EP | 3541325 A1 | 9/2019 |
| EP | 3541328 A1 | 9/2019 |
| EP | 3542758 A1 | 9/2019 |
| EP | 1740265 B1 | 10/2019 |
| EP | 2039756 B1 | 10/2019 |
| EP | 2456506 B1 | 10/2019 |
| EP | 2470122 B1 | 10/2019 |
| EP | 2613738 B1 | 10/2019 |
| EP | 2637607 B1 | 10/2019 |
| EP | 2674174 B1 | 10/2019 |
| EP | 2811923 B1 | 10/2019 |
| EP | 2901967 B1 | 10/2019 |
| EP | 3010431 B1 | 10/2019 |
| EP | 3019091 B1 | 10/2019 |
| EP | 3019123 B1 | 10/2019 |
| EP | 3057522 B1 | 10/2019 |
| EP | 3067075 B1 | 10/2019 |
| EP | 3146937 B1 | 10/2019 |
| EP | 3238777 B1 | 10/2019 |
| EP | 3359211 B1 | 10/2019 |
| EP | 3388026 B1 | 10/2019 |
| EP | 3432806 B1 | 10/2019 |
| EP | 3496626 A4 | 10/2019 |
| EP | 3544548 A1 | 10/2019 |
| EP | 3545905 A1 | 10/2019 |
| EP | 3547936 A1 | 10/2019 |
| EP | 3547966 A1 | 10/2019 |
| EP | 3549555 A1 | 10/2019 |
| EP | 3549556 A1 | 10/2019 |
| EP | 3552585 A1 | 10/2019 |
| EP | 3554424 A1 | 10/2019 |
| EP | 3556323 A1 | 10/2019 |
| EP | 3558165 A1 | 10/2019 |
| EP | 3558168 A1 | 10/2019 |
| EP | 3558169 A2 | 10/2019 |
| EP | 2043559 B1 | 11/2019 |
| EP | 2358308 B1 | 11/2019 |
| EP | 2405863 B1 | 11/2019 |
| EP | 2701633 B1 | 11/2019 |
| EP | 2898857 B1 | 11/2019 |
| EP | 2967853 B1 | 11/2019 |
| EP | 3009104 B1 | 11/2019 |
| EP | 3021792 B1 | 11/2019 |
| EP | 3076900 B1 | 11/2019 |
| EP | 3111889 B1 | 11/2019 |
| EP | 3142607 B1 | 11/2019 |
| EP | 3167850 B1 | 11/2019 |
| EP | 3397205 B1 | 11/2019 |
| EP | 3563799 A1 | 11/2019 |
| EP | 3563806 A1 | 11/2019 |
| EP | 3570779 A1 | 11/2019 |
| EP | 3572045 A1 | 11/2019 |
| EP | 3572117 A1 | 11/2019 |
| EP | 3479800 A4 | 12/2019 |
| EP | 3576677 A1 | 12/2019 |
| EP | 3579761 A2 | 12/2019 |
| EP | 3579788 A1 | 12/2019 |
| EP | 3582697 A1 | 12/2019 |
| EP | 3583922 A1 | 12/2019 |
| EP | 3445443 A4 | 1/2020 |
| EP | 3590471 A1 | 1/2020 |
| EP | 3590472 A1 | 1/2020 |
| EP | 3592284 A1 | 1/2020 |
| EP | 3592288 A1 | 1/2020 |
| EP | 3592289 A1 | 1/2020 |
| EP | 3593763 A1 | 1/2020 |
| EP | 3595588 A1 | 1/2020 |
| EP | 3600156 A1 | 2/2020 |
| EP | 3600159 A1 | 2/2020 |
| EP | 3606443 A1 | 2/2020 |
| EP | 3606472 A1 | 2/2020 |
| EP | 2241287 B2 | 3/2020 |
| EP | 2376013 B1 | 3/2020 |
| EP | 2911593 B1 | 3/2020 |
| EP | 2995279 B1 | 3/2020 |
| EP | 3009103 B1 | 3/2020 |
| EP | 3038664 B1 | 3/2020 |
| EP | 3167848 B1 | 3/2020 |
| EP | 3175822 B1 | 3/2020 |
| EP | 3179960 B1 | 3/2020 |
| EP | 3280479 B1 | 3/2020 |
| EP | 3616651 A1 | 3/2020 |
| EP | 3619136 A1 | 3/2020 |
| EP | 3626208 A1 | 3/2020 |
| EP | 1667614 B2 | 4/2020 |
| EP | 2119417 B2 | 4/2020 |
| EP | 2155114 B1 | 4/2020 |
| EP | 2299937 B1 | 4/2020 |
| EP | 2331016 B1 | 4/2020 |
| EP | 2376013 B8 | 4/2020 |
| EP | 2413843 B1 | 4/2020 |
| EP | 2854705 B1 | 4/2020 |
| EP | 2918249 B1 | 4/2020 |
| EP | 2922593 B1 | 4/2020 |
| EP | 2950753 B1 | 4/2020 |
| EP | 2967810 B1 | 4/2020 |
| EP | 3110367 B1 | 4/2020 |
| EP | 3111888 B1 | 4/2020 |
| EP | 3128927 B1 | 4/2020 |
| EP | 3134032 B1 | 4/2020 |
| EP | 3142606 B1 | 4/2020 |
| EP | 3270825 B1 | 4/2020 |
| EP | 3300696 B1 | 4/2020 |
| EP | 3316823 B1 | 4/2020 |
| EP | 3334487 B1 | 4/2020 |
| EP | 3342355 B1 | 4/2020 |
| EP | 3373863 B1 | 4/2020 |

(56) References Cited

FOREIGN PATENT DOCUMENTS

| | | | |
|---|---|---|---|
| EP | 3459498 B1 | 4/2020 |
| EP | 3470105 B1 | 4/2020 |
| EP | 3628239 A1 | 4/2020 |
| EP | 3628274 A1 | 4/2020 |
| EP | 3632338 A1 | 4/2020 |
| EP | 3636312 A1 | 4/2020 |
| EP | 3639792 A1 | 4/2020 |
| EP | 3639888 A1 | 4/2020 |
| EP | 3643273 A1 | 4/2020 |
| EP | 1895942 B1 | 5/2020 |
| EP | 2120821 B1 | 5/2020 |
| EP | 2437688 B1 | 5/2020 |
| EP | 2785281 B1 | 5/2020 |
| EP | 2852354 B1 | 5/2020 |
| EP | 2884906 B1 | 5/2020 |
| EP | 2999412 B1 | 5/2020 |
| EP | 3060174 B1 | 5/2020 |
| EP | 3071147 B1 | 5/2020 |
| EP | 3104812 B1 | 5/2020 |
| EP | 3139861 B1 | 5/2020 |
| EP | 3232989 B1 | 5/2020 |
| EP | 3294219 B1 | 5/2020 |
| EP | 3298970 B1 | 5/2020 |
| EP | 3302366 B1 | 5/2020 |
| EP | 3323389 B1 | 5/2020 |
| EP | 3332744 B1 | 5/2020 |
| EP | 3402440 B1 | 5/2020 |
| EP | 3417813 B1 | 5/2020 |
| EP | 3417831 B1 | 5/2020 |
| EP | 3457987 B1 | 5/2020 |
| EP | 3484413 B1 | 5/2020 |
| EP | 3531975 B1 | 5/2020 |
| EP | 3644866 A1 | 5/2020 |
| EP | 3646822 A1 | 5/2020 |
| EP | 3646824 A1 | 5/2020 |
| EP | 3646825 A1 | 5/2020 |
| EP | 3648706 A1 | 5/2020 |
| EP | 3648709 A1 | 5/2020 |
| EP | 3656354 A1 | 5/2020 |
| EP | 1648339 B2 | 6/2020 |
| EP | 2072027 B1 | 6/2020 |
| EP | 2331016 B8 | 6/2020 |
| EP | 2616007 B1 | 6/2020 |
| EP | 2967856 B1 | 6/2020 |
| EP | 3042635 B1 | 6/2020 |
| EP | 3060165 B1 | 6/2020 |
| EP | 3280338 B1 | 6/2020 |
| EP | 3283010 B1 | 6/2020 |
| EP | 3400908 B1 | 6/2020 |
| EP | 3494928 B1 | 6/2020 |
| EP | 3498225 B1 | 6/2020 |
| EP | 3583920 B1 | 6/2020 |
| EP | 3659553 A1 | 6/2020 |
| EP | 3661429 A1 | 6/2020 |
| EP | 3661436 A1 | 6/2020 |
| EP | 3668450 A1 | 6/2020 |
| EP | 3668452 A1 | 6/2020 |
| EP | 3669828 A1 | 6/2020 |
| EP | 3669829 A1 | 6/2020 |
| EP | 2271284 B1 | 7/2020 |
| EP | 2291145 B1 | 7/2020 |
| EP | 2512952 B1 | 7/2020 |
| EP | 2558029 B1 | 7/2020 |
| EP | 2693985 B1 | 7/2020 |
| EP | 2858708 B1 | 7/2020 |
| EP | 2862546 B1 | 7/2020 |
| EP | 2967807 B1 | 7/2020 |
| EP | 2967866 B1 | 7/2020 |
| EP | 3061421 B1 | 7/2020 |
| EP | 3107497 B1 | 7/2020 |
| EP | 3139862 B1 | 7/2020 |
| EP | 3423000 B1 | 7/2020 |
| EP | 3441045 B1 | 7/2020 |
| EP | 3451972 B1 | 7/2020 |
| EP | 3501454 B1 | 7/2020 |
| EP | 3512466 B1 | 7/2020 |
| EP | 3616652 B1 | 7/2020 |
| EP | 3672528 A1 | 7/2020 |
| EP | 3672529 A1 | 7/2020 |
| EP | 3672532 A1 | 7/2020 |
| EP | 3673925 A1 | 7/2020 |
| EP | 3679894 A1 | 7/2020 |
| EP | 3681439 A1 | 7/2020 |
| EP | 3681441 A1 | 7/2020 |
| EP | 3682852 A1 | 7/2020 |
| EP | 3682854 A1 | 7/2020 |
| EP | 3685802 A1 | 7/2020 |
| EP | 2367505 B1 | 8/2020 |
| EP | 2497445 B1 | 8/2020 |
| EP | 2537486 B1 | 8/2020 |
| EP | 2777616 B1 | 8/2020 |
| EP | 3007651 B1 | 8/2020 |
| EP | 3052053 B1 | 8/2020 |
| EP | 3237033 B1 | 8/2020 |
| EP | 3388005 B1 | 8/2020 |
| EP | 3410986 B1 | 8/2020 |
| EP | 3451974 B1 | 8/2020 |
| EP | 3463192 B1 | 8/2020 |
| EP | 3554423 B1 | 8/2020 |
| EP | 3568089 A4 | 8/2020 |
| EP | 3573544 B1 | 8/2020 |
| EP | 3634255 B1 | 8/2020 |
| EP | 3689299 A1 | 8/2020 |
| EP | 3691567 A1 | 8/2020 |
| EP | 3695810 A1 | 8/2020 |
| EP | 3697342 A1 | 8/2020 |
| EP | 3697346 A1 | 8/2020 |
| EP | 2485795 B1 | 9/2020 |
| EP | 3125777 B1 | 9/2020 |
| EP | 3182930 B1 | 9/2020 |
| EP | 3285690 B1 | 9/2020 |
| EP | 3459500 B1 | 9/2020 |
| EP | 3570782 B1 | 9/2020 |
| EP | 3700467 A1 | 9/2020 |
| EP | 3711711 A1 | 9/2020 |
| EP | 3714936 A1 | 9/2020 |
| EP | 2979667 B2 | 10/2020 |
| EP | 3193783 B1 | 10/2020 |
| EP | 3490501 B1 | 10/2020 |
| EP | 3718509 A1 | 10/2020 |
| EP | 3720363 A1 | 10/2020 |
| EP | 3721811 A1 | 10/2020 |
| EP | 2387973 B1 | 11/2020 |
| EP | 2427144 B1 | 11/2020 |
| EP | 2506777 B1 | 11/2020 |
| EP | 2793743 B1 | 11/2020 |
| EP | 2825203 B1 | 11/2020 |
| EP | 2863842 B1 | 11/2020 |
| EP | 2967700 B1 | 11/2020 |
| EP | 2977026 B1 | 11/2020 |
| EP | 3139864 B1 | 11/2020 |
| EP | 3145451 B1 | 11/2020 |
| EP | 3156007 B1 | 11/2020 |
| EP | 3244834 B1 | 11/2020 |
| EP | 3298987 B1 | 11/2020 |
| EP | 3302362 B1 | 11/2020 |
| EP | 3311777 B1 | 11/2020 |
| EP | 3316819 B1 | 11/2020 |
| EP | 3361988 B1 | 11/2020 |
| EP | 3503813 B1 | 11/2020 |
| EP | 3527170 B1 | 11/2020 |
| EP | 3530236 B1 | 11/2020 |
| EP | 3590471 B1 | 11/2020 |
| EP | 3593762 B1 | 11/2020 |
| EP | 3737336 A1 | 11/2020 |
| EP | 3740162 A1 | 11/2020 |
| EP | 2370138 B1 | 12/2020 |
| EP | 2445450 B1 | 12/2020 |
| EP | 2739250 B1 | 12/2020 |
| EP | 2877123 B1 | 12/2020 |
| EP | 2967834 B1 | 12/2020 |
| EP | 2996632 B1 | 12/2020 |
| EP | 3090703 B1 | 12/2020 |
| EP | 3191025 B1 | 12/2020 |

(56) References Cited

FOREIGN PATENT DOCUMENTS

| | | | |
|---|---|---|---|
| EP | 3202371 | B1 | 12/2020 |
| EP | 3316822 | B1 | 12/2020 |
| EP | 3334382 | B1 | 12/2020 |
| EP | 3337424 | B1 | 12/2020 |
| EP | 3367896 | B1 | 12/2020 |
| EP | 3368582 | B1 | 12/2020 |
| EP | 3397208 | B1 | 12/2020 |
| EP | 3476366 | B1 | 12/2020 |
| EP | 3481303 | B1 | 12/2020 |
| EP | 3538028 | B1 | 12/2020 |
| EP | 3539510 | B1 | 12/2020 |
| EP | 3544548 | B1 | 12/2020 |
| EP | 3545906 | B1 | 12/2020 |
| EP | 3572117 | B1 | 12/2020 |
| EP | 3593763 | B1 | 12/2020 |
| EP | 3744291 | A1 | 12/2020 |
| EP | 3749254 | A1 | 12/2020 |
| EP | 3753535 | A1 | 12/2020 |
| EP | 3756623 | A1 | 12/2020 |
| EP | 1906883 | B1 | 1/2021 |
| EP | 2334261 | B1 | 1/2021 |
| EP | 2349096 | B1 | 1/2021 |
| EP | 2568924 | B1 | 1/2021 |
| EP | 2699202 | B1 | 1/2021 |
| EP | 2713894 | B1 | 1/2021 |
| EP | 3040054 | B1 | 1/2021 |
| EP | 3131502 | B1 | 1/2021 |
| EP | 3197397 | B1 | 1/2021 |
| EP | 3256178 | B1 | 1/2021 |
| EP | 3290007 | B1 | 1/2021 |
| EP | 3316821 | B1 | 1/2021 |
| EP | 3337412 | B1 | 1/2021 |
| EP | 3432834 | B1 | 1/2021 |
| EP | 3454786 | B1 | 1/2021 |
| EP | 3474778 | B1 | 1/2021 |
| EP | 3528748 | B1 | 1/2021 |
| EP | 3547966 | B1 | 1/2021 |
| EP | 3603576 | B1 | 1/2021 |
| EP | 3758651 | A1 | 1/2021 |
| EP | 3760164 | A1 | 1/2021 |
| EP | 3763331 | A1 | 1/2021 |
| EP | 3769721 | A1 | 1/2021 |
| EP | 2273951 | B1 | 2/2021 |
| EP | 2379008 | B1 | 2/2021 |
| EP | 2835112 | B1 | 2/2021 |
| EP | 2996641 | B1 | 2/2021 |
| EP | 3043747 | B1 | 2/2021 |
| EP | 3340936 | B1 | 2/2021 |
| EP | 3454794 | B1 | 2/2021 |
| EP | 3457985 | B1 | 2/2021 |
| EP | 3503847 | B1 | 2/2021 |
| EP | 3538027 | B1 | 2/2021 |
| EP | 3558168 | B1 | 2/2021 |
| EP | 3581232 | B1 | 2/2021 |
| EP | 3646354 | B1 | 2/2021 |
| EP | 3697324 | B1 | 2/2021 |
| EP | 3773271 | A1 | 2/2021 |
| EP | 3773329 | A1 | 2/2021 |
| EP | 2299938 | B1 | 3/2021 |
| EP | 2470121 | B1 | 3/2021 |
| EP | 2564811 | B1 | 3/2021 |
| EP | 2679198 | B1 | 3/2021 |
| EP | 3068346 | B1 | 3/2021 |
| EP | 3160394 | B1 | 3/2021 |
| EP | 3169245 | B1 | 3/2021 |
| EP | 3178443 | B1 | 3/2021 |
| EP | 3184081 | B1 | 3/2021 |
| EP | 3226956 | B1 | 3/2021 |
| EP | 3324892 | B1 | 3/2021 |
| EP | 3334354 | B1 | 3/2021 |
| EP | 3402446 | B1 | 3/2021 |
| EP | 3442469 | B1 | 3/2021 |
| EP | 3503851 | B1 | 3/2021 |
| EP | 3506855 | B1 | 3/2021 |
| EP | 3531979 | B1 | 3/2021 |
| EP | 3535010 | B1 | 3/2021 |
| EP | 3581151 | B1 | 3/2021 |
| EP | 3590472 | B1 | 3/2021 |
| EP | 3593760 | B1 | 3/2021 |
| EP | 3646825 | B1 | 3/2021 |
| EP | 3649985 | B1 | 3/2021 |
| EP | 3787561 | A1 | 3/2021 |
| EP | 3790501 | A1 | 3/2021 |
| EP | 3791795 | A1 | 3/2021 |
| EP | 3791828 | A1 | 3/2021 |
| EP | 3796872 | A1 | 3/2021 |
| EP | 3796873 | A1 | 3/2021 |
| EP | 3796875 | A1 | 3/2021 |
| EP | 3796876 | A1 | 3/2021 |
| EP | 1734872 | B1 | 4/2021 |
| EP | 2594230 | B1 | 4/2021 |
| EP | 2624785 | B1 | 4/2021 |
| EP | 2670349 | B1 | 4/2021 |
| EP | 2793752 | B1 | 4/2021 |
| EP | 2823769 | B1 | 4/2021 |
| EP | 2964152 | B1 | 4/2021 |
| EP | 3253331 | B1 | 4/2021 |
| EP | 3290004 | B1 | 4/2021 |
| EP | 3311778 | B1 | 4/2021 |
| EP | 3367979 | B1 | 4/2021 |
| EP | 3487420 | B1 | 4/2021 |
| EP | 3558165 | B1 | 4/2021 |
| EP | 3616651 | B1 | 4/2021 |
| EP | 3619136 | B1 | 4/2021 |
| EP | 3626208 | B1 | 4/2021 |
| EP | 3632379 | B1 | 4/2021 |
| EP | 3646823 | B1 | 4/2021 |
| EP | 3646824 | B1 | 4/2021 |
| EP | 3653173 | B1 | 4/2021 |
| EP | 1951155 | B1 | 5/2021 |
| EP | 2073755 | B1 | 5/2021 |
| EP | 2948100 | B1 | 5/2021 |
| EP | 3099270 | B1 | 5/2021 |
| EP | 3150172 | B1 | 5/2021 |
| EP | 3178445 | B1 | 5/2021 |
| EP | 3310301 | B | 5/2021 |
| EP | 3582697 | B1 | 5/2021 |
| EP | 3592295 | B1 | 5/2021 |
| EP | 3639888 | B1 | 5/2021 |
| EP | 3669828 | B1 | 5/2021 |
| EP | 2471492 | B1 | 6/2021 |
| EP | 2486894 | B1 | 6/2021 |
| EP | 2750630 | B1 | 6/2021 |
| EP | 3247312 | B1 | 6/2021 |
| EP | 3294215 | B1 | 6/2021 |
| EP | 3323353 | B1 | 6/2021 |
| EP | 3360513 | B1 | 6/2021 |
| EP | 3488821 | B1 | 6/2021 |
| EP | 3549555 | B1 | 6/2021 |
| EP | 3576677 | B1 | 6/2021 |
| EP | 3632338 | B1 | 6/2021 |
| EP | 3834879 | A1 | 6/2021 |
| EP | 2381895 | B1 | 7/2021 |
| EP | 2611389 | B1 | 7/2021 |
| EP | 2779945 | B1 | 7/2021 |
| EP | 3193740 | B1 | 7/2021 |
| EP | 3206629 | B1 | 7/2021 |
| EP | 3277222 | B1 | 7/2021 |
| EP | 3400907 | B1 | 7/2021 |
| EP | 3435919 | B1 | 7/2021 |
| EP | 3522800 | B1 | 7/2021 |
| EP | 3539508 | B1 | 7/2021 |
| EP | 3539509 | B1 | 7/2021 |
| EP | 3572044 | B1 | 7/2021 |
| EP | 3592289 | B1 | 7/2021 |
| EP | 3668450 | B1 | 7/2021 |
| EP | 3681439 | B1 | 7/2021 |
| EP | 3691567 | B1 | 7/2021 |
| EP | 3789077 | A4 | 7/2021 |
| EP | 3846740 | A1 | 7/2021 |
| EP | 3849472 | A1 | 7/2021 |
| EP | 2558032 | B1 | 8/2021 |
| EP | 2992857 | B1 | 8/2021 |
| EP | 2994075 | B1 | 8/2021 |

(56) References Cited

FOREIGN PATENT DOCUMENTS

| | | | |
|---|---|---|---|
| EP | 3038539 | B1 | 8/2021 |
| EP | 3287099 | B1 | 8/2021 |
| EP | 3348235 | B1 | 8/2021 |
| EP | 3643273 | B1 | 8/2021 |
| EP | 3646822 | B1 | 8/2021 |
| EP | 3658215 | B1 | 8/2021 |
| EP | 3659553 | B1 | 8/2021 |
| EP | 3723665 | B1 | 8/2021 |
| EP | 3744290 | B1 | 8/2021 |
| EP | 3860530 | A1 | 8/2021 |
| EP | 3863567 | A1 | 8/2021 |
| EP | 2040645 | B1 | 9/2021 |
| EP | 2329796 | B1 | 9/2021 |
| EP | 3125827 | B1 | 9/2021 |
| EP | 3137146 | B1 | 9/2021 |
| EP | 3288494 | B1 | 9/2021 |
| EP | 3288497 | B1 | 9/2021 |
| EP | 3446660 | B1 | 9/2021 |
| EP | 3454784 | B1 | 9/2021 |
| EP | 3456293 | B1 | 9/2021 |
| EP | 3457989 | B1 | 9/2021 |
| EP | 3496664 | B1 | 9/2021 |
| EP | 3503848 | B1 | 9/2021 |
| EP | 3512465 | B1 | 9/2021 |
| EP | 3544664 | B1 | 9/2021 |
| EP | 3568089 | B1 | 9/2021 |
| EP | 3592288 | B1 | 9/2021 |
| EP | 3606472 | B1 | 9/2021 |
| EP | 3669829 | B1 | 9/2021 |
| EP | 3672528 | B1 | 9/2021 |
| EP | 3833302 | A4 | 9/2021 |
| EP | 3870110 | A1 | 9/2021 |
| EP | 2249711 | B1 | 10/2021 |
| EP | 2538883 | B1 | 10/2021 |
| EP | 2723273 | B1 | 10/2021 |
| EP | 3119351 | B1 | 10/2021 |
| EP | 3267946 | B1 | 10/2021 |
| EP | 3275404 | B1 | 10/2021 |
| EP | 3280482 | B1 | 10/2021 |
| EP | 3334381 | B1 | 10/2021 |
| EP | 3639792 | B1 | 10/2021 |
| EP | 3886762 | A1 | 10/2021 |
| EP | 3886763 | A1 | 10/2021 |
| EP | 3892240 | A1 | 10/2021 |
| EP | 3897454 | A1 | 10/2021 |
| EP | 3900679 | A1 | 10/2021 |
| EP | 2331018 | B1 | 11/2021 |
| EP | 2429455 | B1 | 11/2021 |
| EP | 2538878 | B1 | 11/2021 |
| EP | 2699302 | B1 | 11/2021 |
| EP | 2706958 | B1 | 11/2021 |
| EP | 2892467 | B1 | 11/2021 |
| EP | 2999434 | B1 | 11/2021 |
| EP | 3024527 | B1 | 11/2021 |
| EP | 3061422 | B1 | 11/2021 |
| EP | 3107500 | B1 | 11/2021 |
| EP | 3110468 | B1 | 11/2021 |
| EP | 3154474 | B1 | 11/2021 |
| EP | 3213715 | B1 | 11/2021 |
| EP | 3256076 | B1 | 11/2021 |
| EP | 3288499 | B1 | 11/2021 |
| EP | 3360514 | B1 | 11/2021 |
| EP | 3429507 | B1 | 11/2021 |
| EP | 3445443 | B1 | 11/2021 |
| EP | 3454785 | B1 | 11/2021 |
| EP | 3505077 | B1 | 11/2021 |
| EP | 3672529 | B1 | 11/2021 |
| EP | 3760164 | B1 | 11/2021 |
| EP | 3908228 | A1 | 11/2021 |
| EP | 3912595 | A1 | 11/2021 |
| EP | 3912596 | A1 | 11/2021 |
| EP | 2358307 | B1 | 12/2021 |
| EP | 2765954 | B1 | 12/2021 |
| EP | 2777608 | B1 | 12/2021 |
| EP | 2991584 | B1 | 12/2021 |
| EP | 3283011 | B1 | 12/2021 |
| EP | 3288479 | B1 | 12/2021 |
| EP | 3344167 | B1 | 12/2021 |
| EP | 3410987 | B1 | 12/2021 |
| EP | 3481339 | B1 | 12/2021 |
| EP | 3482718 | B1 | 12/2021 |
| EP | 3490465 | B1 | 12/2021 |
| EP | 3498224 | B1 | 12/2021 |
| EP | 3503846 | B1 | 12/2021 |
| EP | 3592284 | B1 | 12/2021 |
| EP | 3624705 | B1 | 12/2021 |
| EP | 3749254 | B1 | 12/2021 |
| EP | 3914191 | A1 | 12/2021 |
| EP | 3915493 | A1 | 12/2021 |
| EP | 2400922 | B1 | 1/2022 |
| EP | 2545885 | B1 | 1/2022 |
| EP | 2747708 | B1 | 1/2022 |
| EP | 2763708 | B1 | 1/2022 |
| EP | 2994072 | B1 | 1/2022 |
| EP | 3220856 | B1 | 1/2022 |
| EP | 3288498 | B1 | 1/2022 |
| EP | 3534840 | B1 | 1/2022 |
| EP | 3558169 | B1 | 1/2022 |
| EP | 3668452 | B1 | 1/2022 |
| EP | 3682854 | B1 | 1/2022 |
| EP | 3697346 | B1 | 1/2022 |
| EP | 3700467 | B1 | 1/2022 |
| EP | 3740162 | B1 | 1/2022 |
| EP | 3294218 | B1 | 2/2022 |
| EP | 3457988 | B1 | 2/2022 |
| EP | 3481336 | B1 | 2/2022 |
| EP | 3673925 | B1 | 2/2022 |
| EP | 3689299 | B1 | 2/2022 |
| EP | 3753535 | B1 | 2/2022 |
| EP | 3860530 | B1 | 2/2022 |
| EP | 2520249 | B1 | 3/2022 |
| EP | 2558033 | B1 | 3/2022 |
| EP | 2623068 | B1 | 3/2022 |
| EP | 2866737 | B1 | 3/2022 |
| EP | 3107495 | B1 | 3/2022 |
| EP | 3160396 | B1 | 3/2022 |
| EP | 3179800 | B1 | 3/2022 |
| EP | 3193782 | B1 | 3/2022 |
| EP | 3334380 | B1 | 3/2022 |
| EP | 3355800 | B1 | 3/2022 |
| EP | 3479797 | B1 | 3/2022 |
| EP | 3547936 | B1 | 3/2022 |
| EP | 3628274 | B1 | 3/2022 |
| EP | 3679894 | B1 | 3/2022 |
| EP | 3711711 | B1 | 3/2022 |
| EP | 3714936 | B1 | 3/2022 |
| EP | 3787561 | B1 | 3/2022 |
| EP | 3791795 | B1 | 3/2022 |
| EP | 3962415 | A1 | 3/2022 |
| EP | 2488126 | B1 | 4/2022 |
| EP | 2536360 | B1 | 4/2022 |
| EP | 2611388 | B1 | 4/2022 |
| EP | 2651336 | B1 | 4/2022 |
| EP | 2699200 | B1 | 4/2022 |
| EP | 2916781 | B1 | 4/2022 |
| EP | 3174502 | B1 | 4/2022 |
| EP | 3209221 | B1 | 4/2022 |
| EP | 3302297 | B1 | 4/2022 |
| EP | 3349693 | B1 | 4/2022 |
| EP | 3487451 | B1 | 4/2022 |
| EP | 3500184 | B1 | 4/2022 |
| EP | 3600159 | B1 | 4/2022 |
| EP | 3628239 | B1 | 4/2022 |
| EP | 3644866 | B1 | 4/2022 |
| EP | 3681441 | B1 | 4/2022 |
| EP | 3796873 | B1 | 4/2022 |
| EP | 2268231 | B1 | 5/2022 |
| EP | 2856973 | B1 | 5/2022 |
| EP | 2962664 | B1 | 5/2022 |
| EP | 3311774 | B1 | 5/2022 |
| EP | 3335670 | B1 | 5/2022 |
| EP | 3403616 | B1 | 5/2022 |
| EP | 3445290 | B1 | 5/2022 |
| EP | 3541316 | B1 | 5/2022 |

(56) References Cited

FOREIGN PATENT DOCUMENTS

| | | | |
|---|---|---|---|
| EP | 3648709 | B1 | 5/2022 |
| EP | 3695810 | B1 | 5/2022 |
| EP | 3721811 | B1 | 5/2022 |
| EP | 3773271 | B1 | 5/2022 |
| EP | 2538893 | B1 | 6/2022 |
| EP | 2575681 | B1 | 6/2022 |
| EP | 2583640 | B1 | 6/2022 |
| EP | 3071149 | B1 | 6/2022 |
| EP | 3253332 | B1 | 6/2022 |
| EP | 3283009 | B1 | 6/2022 |
| EP | 3296979 | B1 | 6/2022 |
| EP | 3298988 | B1 | 6/2022 |
| EP | 3342377 | B1 | 6/2022 |
| EP | 3365349 | B1 | 6/2022 |
| EP | 3397206 | B1 | 6/2022 |
| EP | 3426194 | B1 | 6/2022 |
| EP | 3595588 | B1 | 6/2022 |
| EP | 3636312 | B1 | 6/2022 |
| EP | 3661436 | B1 | 6/2022 |
| EP | 3790501 | B1 | 6/2022 |
| EP | 3846740 | B1 | 6/2022 |
| EP | 3849472 | B1 | 6/2022 |
| EP | 3897454 | B1 | 6/2022 |
| EP | 4014928 | A1 | 6/2022 |
| EP | 2621409 | B1 | 7/2022 |
| EP | 2787926 | B1 | 7/2022 |
| EP | 2836473 | B1 | 7/2022 |
| EP | 2950752 | B1 | 7/2022 |
| EP | 3060171 | B1 | 7/2022 |
| EP | 3206631 | B1 | 7/2022 |
| EP | 3245980 | B1 | 7/2022 |
| EP | 3256073 | B1 | 7/2022 |
| EP | 3311783 | B1 | 7/2022 |
| EP | 3347182 | B1 | 7/2022 |
| EP | 3389557 | B1 | 7/2022 |
| EP | 3463120 | B1 | 7/2022 |
| EP | 3579788 | B1 | 7/2022 |
| EP | 3756623 | B1 | 7/2022 |
| EP | 3796872 | B1 | 7/2022 |
| EP | 3796876 | B1 | 7/2022 |
| EP | 2313152 | B1 | 8/2022 |
| EP | 2688516 | B1 | 8/2022 |
| EP | 2849678 | B1 | 8/2022 |
| EP | 2950751 | B1 | 8/2022 |
| EP | 2964153 | B1 | 8/2022 |
| EP | 3019092 | B1 | 8/2022 |
| EP | 3184082 | B1 | 8/2022 |
| EP | 3231395 | B1 | 8/2022 |
| EP | 3266417 | B1 | 8/2022 |
| EP | 3407834 | B1 | 8/2022 |
| EP | 3458136 | B1 | 8/2022 |
| EP | 3459499 | B1 | 8/2022 |
| EP | 3471662 | B1 | 8/2022 |
| EP | 3484412 | B1 | 8/2022 |
| EP | 3534841 | B1 | 8/2022 |
| EP | 3541328 | B1 | 8/2022 |
| EP | 3672532 | B1 | 8/2022 |
| EP | 3718509 | B1 | 8/2022 |
| EP | 3769721 | B1 | 8/2022 |
| EP | 3789077 | B1 | 8/2022 |
| EP | 3808228 | B1 | 8/2022 |
| EP | 3915493 | B1 | 8/2022 |
| EP | 3967274 | B1 | 8/2022 |
| EP | 1670351 | B1 | 9/2022 |
| EP | 2777617 | B1 | 9/2022 |
| EP | 2810620 | B1 | 9/2022 |
| EP | 2922592 | B1 | 9/2022 |
| EP | 3038567 | B1 | 9/2022 |
| EP | 3096713 | B1 | 9/2022 |
| EP | 3220857 | B1 | 9/2022 |
| EP | 3448315 | B1 | 9/2022 |
| EP | 3481335 | B1 | 9/2022 |
| EP | 3520715 | B1 | 9/2022 |
| EP | 3645065 | B1 | 9/2022 |
| EP | 3737336 | B1 | 9/2022 |
| EP | 2104470 | B1 | 10/2022 |
| EP | 2536353 | B1 | 10/2022 |
| EP | 2991588 | B1 | 10/2022 |
| EP | 3043755 | B1 | 10/2022 |
| EP | 3288491 | B1 | 10/2022 |
| EP | 3466373 | B1 | 10/2022 |
| EP | 3552585 | B1 | 10/2022 |
| EP | 3791828 | B1 | 10/2022 |
| EP | 3914191 | B1 | 10/2022 |
| EP | 2538882 | B1 | 11/2022 |
| EP | 2698129 | B1 | 11/2022 |
| EP | 2959866 | B1 | 11/2022 |
| EP | 3175823 | B1 | 11/2022 |
| EP | 3280358 | B1 | 11/2022 |
| EP | 3340923 | B1 | 11/2022 |
| EP | 3478224 | B1 | 11/2022 |
| EP | 3490659 | B1 | 11/2022 |
| EP | 3744291 | B1 | 11/2022 |
| FR | 2815844 | B1 | 1/2003 |
| FR | 2826863 | B1 | 9/2003 |
| FR | 2828091 | B1 | 11/2003 |
| FR | 2847800 | B1 | 10/2005 |
| FR | 2858543 | B1 | 2/2006 |
| FR | 2828263 | B1 | 5/2007 |
| FR | 2874812 | B1 | 6/2007 |
| FR | 2874813 | B1 | 6/2007 |
| FR | 2883721 | B1 | 6/2007 |
| FR | 2894131 | B1 | 12/2008 |
| FR | 2899096 | B1 | 12/2008 |
| FR | 2910269 | B1 | 2/2009 |
| FR | 2909857 | B1 | 3/2009 |
| FR | 2906454 | B1 | 4/2009 |
| FR | 2906998 | B1 | 4/2009 |
| FR | 2913879 | B1 | 6/2009 |
| FR | 2916959 | B1 | 9/2009 |
| FR | 2892939 | B1 | 1/2010 |
| FR | 2915678 | B1 | 4/2010 |
| FR | 2930137 | B1 | 4/2010 |
| FR | 2915903 | B1 | 6/2010 |
| FR | 2916627 | B1 | 9/2010 |
| FR | 2920664 | B1 | 9/2010 |
| FR | 2932376 | B1 | 4/2011 |
| FR | 2947716 | B1 | 9/2011 |
| FR | 2945440 | B1 | 12/2012 |
| FR | 2951549 | B1 | 8/2013 |
| FR | 2964855 | B1 | 10/2013 |
| FR | 2977792 | B1 | 10/2013 |
| FR | 2980968 | B1 | 12/2013 |
| FR | 2986149 | B1 | 12/2014 |
| FR | 2997288 | B1 | 1/2015 |
| FR | 2998167 | B1 | 1/2015 |
| FR | 2996747 | B1 | 2/2015 |
| FR | 2996748 | B1 | 2/2015 |
| FR | 3004638 | B1 | 5/2015 |
| FR | 3004914 | B1 | 6/2015 |
| FR | 2982763 | B1 | 7/2015 |
| FR | 2991162 | B1 | 7/2015 |
| FR | 3006582 | B1 | 7/2015 |
| FR | 3001121 | B1 | 1/2016 |
| FR | 2998166 | B1 | 2/2016 |
| FR | 3021862 | B1 | 5/2016 |
| FR | 3006884 | B1 | 6/2016 |
| FR | 3023704 | B1 | 8/2016 |
| FR | 3008885 | B1 | 12/2016 |
| FR | 3033494 | B1 | 3/2017 |
| FR | 3057154 | B1 | 10/2018 |
| FR | 3058631 | B1 | 1/2019 |
| FR | 3058632 | B1 | 1/2019 |
| FR | 3060292 | B1 | 1/2019 |
| FR | 3063631 | B1 | 3/2019 |
| FR | 3020265 | B1 | 9/2019 |
| FR | 3072013 | B1 | 9/2019 |
| GB | 243370 | A | 8/1926 |
| GB | 2407146 | B | 4/2006 |
| GB | 2398245 | B | 3/2007 |
| GB | 2433700 | B | 12/2007 |
| GB | 2478498 | B | 7/2012 |
| GB | 2530487 | B | 12/2016 |
| GB | 2517609 | B | 5/2017 |

(56) References Cited

FOREIGN PATENT DOCUMENTS

| | | |
|---|---|---|
| GB | 2538749 B | 8/2017 |
| GB | 2538072 B | 11/2017 |
| GB | 2536538 B | 7/2018 |
| GB | 2548891 B | 7/2018 |
| JP | 2009505731 A | 2/2009 |
| JP | 2013525039 A | 6/2013 |
| JP | 2013526388 A | 6/2013 |
| JP | 2013539331 A | 10/2013 |
| JP | 2016185404 A | 10/2016 |
| JP | 2019069241 A | 5/2019 |
| JP | 7006940 B2 | 1/2022 |
| JP | 2022037201 A | 3/2022 |
| WO | WO-2007024755 A1 | 3/2007 |
| WO | WO-2009134701 A2 | 11/2009 |
| WO | WO-2011069048 A2 | 6/2011 |
| WO | WO-2011137531 A1 | 11/2011 |
| WO | WO-2011159342 A1 | 12/2011 |
| WO | WO-2016178126 A1 | 11/2016 |
| WO | WO-2017127939 A1 | 8/2017 |
| WO | WO-2020210652 A1 | 10/2020 |

OTHER PUBLICATIONS

"European Application Serial No. 20788456.0, Extended European Search Report mailed Dec. 2, 2022", 4 pgs.
"U.S. Appl. No. 15/418,511, Corrected Notice of Allowability mailed Aug. 21, 2019", 3 pgs.
"U.S. Appl. No. 15/418,511, Non Final Office Action mailed Mar. 8, 2019", 12 pgs.
"U.S. Appl. No. 15/418,511, Notice of Allowance mailed May 30, 2019", 8 pgs.
"U.S. Appl. No. 15/418,511, Preliminary Amendment filed Mar. 7, 2017", 11 pgs.
"U.S. Appl. No. 15/418,511, Response filed Jan. 9, 2019 to Restriction Requirement mailed Nov. 8, 2018", 11 pgs.
"U.S. Appl. No. 15/418,511, Response filed May 6, 2019 to Non Final Office Action mailed Mar. 8, 2019", 9 pgs.
"U.S. Appl. No. 15/418,511, Restriction Requirement mailed Nov. 8, 2018", 5 pgs.
"U.S. Appl. No. 16/559,169, Corrected Notice of Allowability mailed Feb. 23, 2022", 2 pgs.
"U.S. Appl. No. 16/559,169, Corrected Notice of Allowability mailed May 9, 2022", 2 pgs.
"U.S. Appl. No. 16/559,169, Notice of Allowance mailed Feb. 9, 2022", 11 pgs.
"U.S. Appl. No. 16/559,169, Response filed Nov. 29, 2021 to Restriction Requirement mailed Oct. 28, 2021", 7 pgs.
"U.S. Appl. No. 16/559,169, Restriction Requirement mailed Oct. 28, 2021", 5 pgs.
"U.S. Appl. No. 16/845,870, Advisory Action mailed Jun. 13, 2022", 3 pgs.
"U.S. Appl. No. 16/845,870, Final Office Action mailed Mar. 29, 2022", 12 pgs.
"U.S. Appl. No. 16/845,870, Non Final Office Action mailed Dec. 8, 2021", 10 pgs.
"U.S. Appl. No. 16/845,870, Notice of Allowance mailed Jul. 5, 2022", 5 pgs.
"U.S. Appl. No. 16/845,870, Response filed Mar. 4, 2022 to Non Final Office Action mailed Dec. 8, 2021", 15 pgs.
"U.S. Appl. No. 16/845,870, Response filed May 27, 2022 to Final Office Action mailed Mar. 29, 2022", 13 pgs.
"U.S. Appl. No. 16/845,870, Response filed Nov. 4, 2021 to Restriction Requirement mailed Sep. 9, 2021", 7 pgs.
"U.S. Appl. No. 16/845,870, Restriction Requirement mailed Sep. 9, 2021", 7 pgs.
"U.S. Appl. No. 16/845,870, Supplemental Amendment and Response filed Jun. 10, 2022 to Final Office Action mailed Mar. 29, 2022", 11 pgs.
"Australian Application Serial No. 2020271896, First Examination Report mailed Jun. 22, 2022", 3 pgs.
"Australian Application Serial No. 2020271896, Response filed Sep. 21, 2022 to First Examination Report mailed Jun. 22, 2022", 24 pgs.
"Chinese Application Serial No. 201780021798.X, Office Action mailed Feb. 10, 2021", with machine translation, 14 pgs.
"Chinese Application Serial No. 201780021798.X, Office Action mailed Jul. 16, 2020", with English translation of claims, 14 pgs.
"Chinese Application Serial No. 201780021798.X, Office Action mailed Oct. 29, 2019", with English translation of claims, 13 pgs.
"Chinese Application Serial No. 201780021798.X, Response filed Mar. 12, 2020 to Office Action mailed Oct. 29, 2019", w/English Claims, 15 pgs.
"Chinese Application Serial No. 201780021798.X, Response filed Apr. 9, 2021 to Office Action mailed Feb. 10, 2021", w/English Claims, 14 pgs.
"Chinese Application Serial No. 201780021798.X, Response filed Sep. 30, 2020 to Office Action mailed Jul. 16, 2020", with machine translation, 12 pgs.
"Chinese Application Serial No. 202110837427.7, Response filed Oct. 13, 2021", with machine translation, 180 pgs.
"Chinese Application Serial No. 202110837427.7, Voluntary Amendment filed Feb. 18, 2022", w/ English Claims, 20 pgs.
"European Application Serial No. 20788456.0, Response to Communication pursuant to Rules 161 and 162 filed May 26, 2022", 6 pgs.
"European Application Serial No. 17743534.4, Extended European Search Report mailed May 24, 2019", 8 pgs.
"European Application Serial No. 17743534.4, Response filed Dec. 20, 2019 to Extended European Search Report mailed May 24, 2019", 8 pgs.
"International Application Serial No. PCT/CA2017/050097, International Preliminary Report on Patentability mailed Aug. 9, 2018", 9 pgs.
"International Application Serial No. PCT/CA2017/050097, International Search Report mailed Jun. 12, 2017", 5 pgs.
"International Application Serial No. PCT/CA2017/050097, Written Opinion mailed Jun. 12, 2017", 7 pgs.
"International Application Serial No. PCT/US2020/027705, International Preliminary Report on Patentability mailed Oct. 21, 2021", 10 pgs.
"International Application Serial No. PCT/US2020/027705, International Search Report mailed Jul. 24, 2020", 2 pgs.
"International Application Serial No. PCT/US2020/027705, Written Opinion mailed Jul. 24, 2020", 8 pgs.
"Japanese Application Serial No. 2018-539080, Notification of Reasons for Refusal mailed Jan. 22, 2021", w/ English translation, 13 pgs.
"Japanese Application Serial No. 2018-539080, Response filed Apr. 22, 2021 to Notification of Reasons for Refusal mailed Jan. 22, 2021", English translation of claims, 10 pgs.
"Canadian Application Serial No. 3,136,334, Examiners Rule 86(2) Report mailed Jun. 30, 2023", 4 pgs.
"Canadian Application Serial No. 3,136,334, Response filed Apr. 18, 2023 to Examiner's Rule 86(2) Report mailed Dec. 20, 2022", 28 pgs.
"European Application Serial No. 20788456.0, Response filed Jun. 27, 2023 to Extended European Search Report mailed Dec. 2, 2022", 11 pgs.
"Australian Application Serial No. 2022291496, First Examination Report mailed Dec. 6, 2023", 4 pgs.

* cited by examiner

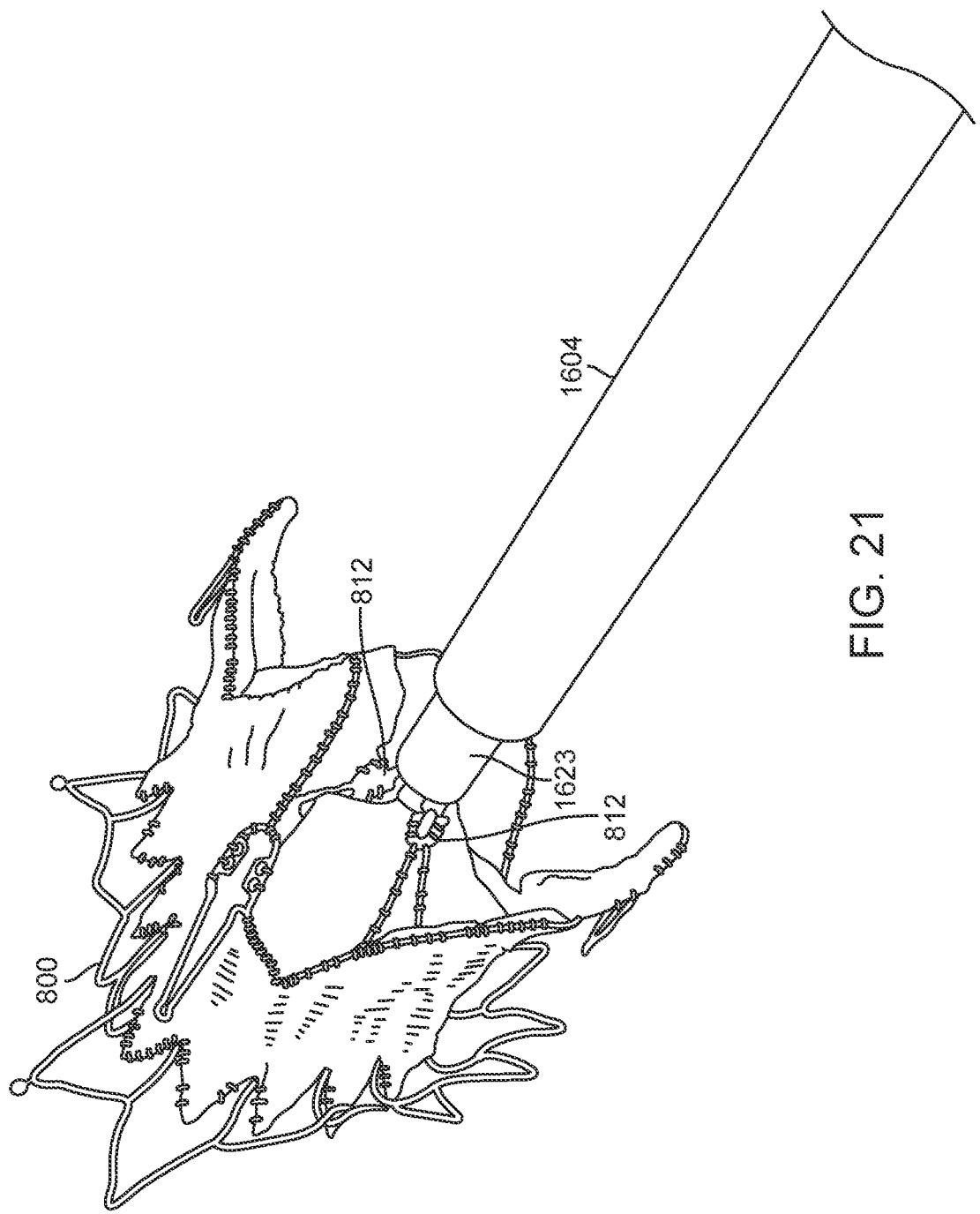

PROSTHETIC VALVE WITH NATURAL BLOOD FLOW

CLAIM OF PRIORITY

The present application is a continuation of U.S. patent application Ser. No. 16/845,870 filed on Apr. 10, 2020, which application is a non-provisional of, and claims the benefit of U.S. Provisional Patent Application No. 62/831,922 filed on Apr. 10, 2019; the entire contents of each of which are incorporated herein by reference.

CROSS-REFERENCE TO RELATED PATENT DOCUMENTS

The present application is related to U.S. patent application Ser. No. 16/559,169 filed Sep. 3, 2019; Ser. No. 15/418,511 filed Jan. 27, 2017 now U.S. Pat. No. 10,433,952; and U.S. Provisional Patent Application No. 62/288,987 filed on Jan. 29, 2016; the entire contents of each of which is incorporated herein by reference.

BACKGROUND

The heart of vertebrate animals is divided into four chambers, and is equipped with four valves (the mitral, aortic, pulmonary and tricuspid valves) that ensure that blood pumped by the heart flows in a forward direction (sometime also referred to as a downstream or antegrade direction) through the cardiovascular system. The mitral valve of a healthy heart prevents the backflow (sometime also referred to as retrograde or upstream flow) of blood from the left ventricle into the left atrium of the heart, and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (also known as regurgitate) from the left ventricle back into the left atrium. Any such impairments compromise cardiac function, and can be debilitating or life threatening.

Numerous surgical methods and devices have accordingly been developed to treat mitral valve dysfunction, including open-heart surgical techniques for replacing, repairing or reshaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped state on the end of a flexible catheter and advanced through a blood vessel or the body of the patient until the valve reaches the implantation site. The prosthetic valve is then expanded to its functional size at the site of the defective native valve. The present application discloses examples directed at mitral valves but this is not intended to be limiting and one of skill in the art will appreciate that the prosthetic valves disclosed herein may be used in another cardiac valves such as the tricuspid valve, aortic valve, pulmonary valve, or any other valve in the body such as a venous valve.

BRIEF DESCRIPTION OF THE DRAWINGS

In the drawings, which are not necessarily drawn to scale, like numerals may describe similar components in different views or similar steps. Like numerals having different letter suffixes may represent different instances of similar components. The drawings illustrate generally, by way of example, but not by way of limitation, various examples discussed in the present document.

FIG. 21 illustrates engagement of the delivery device in FIG. 16 with the prosthetic valve of FIG. 8A.

DETAILED DESCRIPTION

While some of the surgical and less invasive treatments for valvar regurgitation are promising, they can be difficult to deliver, expensive to manufacture, or may not be indicated for all patients or provide the best clinical results. Therefore, it would be desirable to provide improved devices and methods for the treatment of valvar insufficiency such as mitral insufficiency. At least some of these objectives will be met by the devices and methods disclosed.

Specific examples of the disclosed device, delivery system, and method will now be described with reference to the drawings. Nothing in this detailed description is intended to imply that any particular component, feature, or step is essential to the invention.

Cardiac Anatomy

Figure 1:
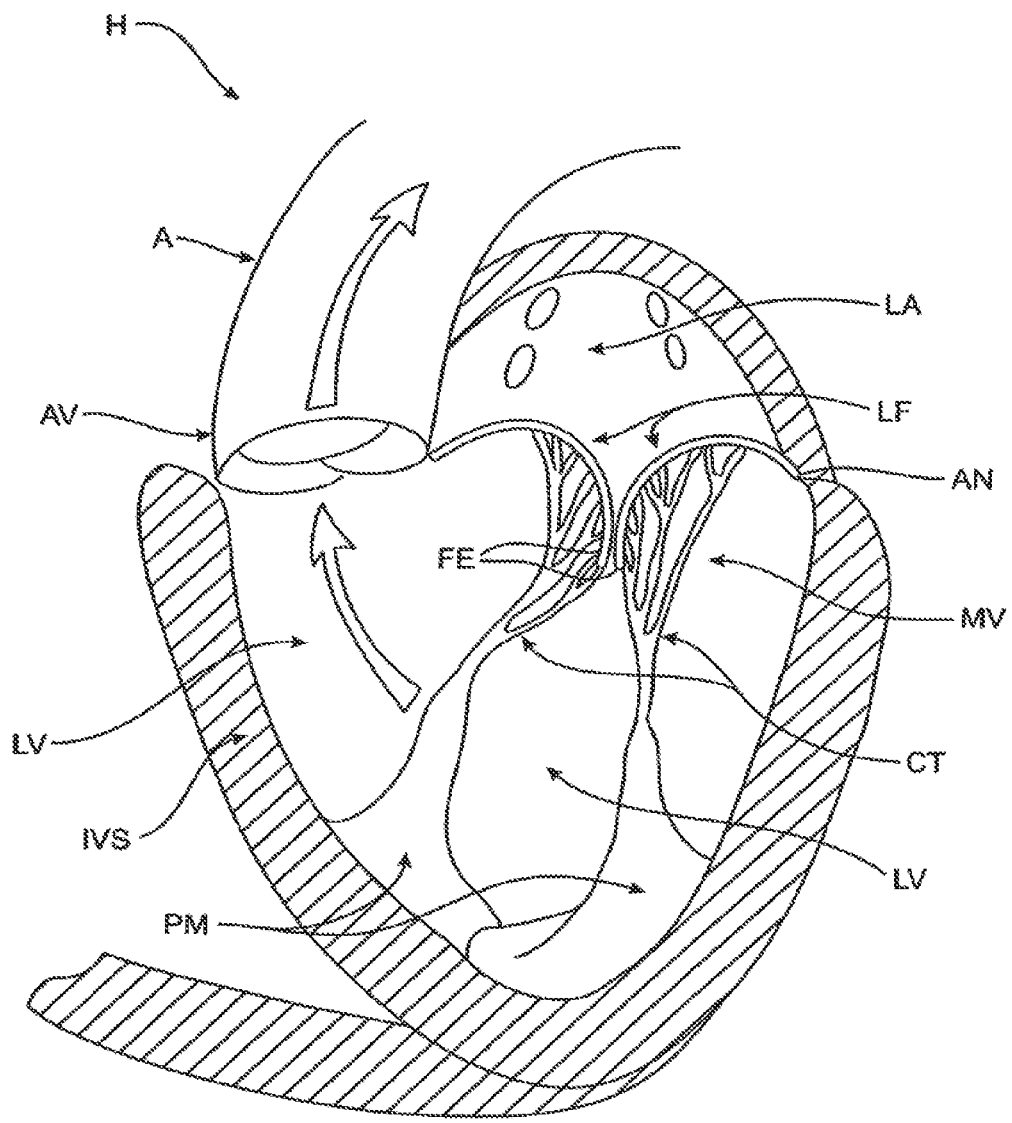
FIG. 1 is a schematic illustration of the left ventricle of a heart showing blood flow during systole with arrows.

The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
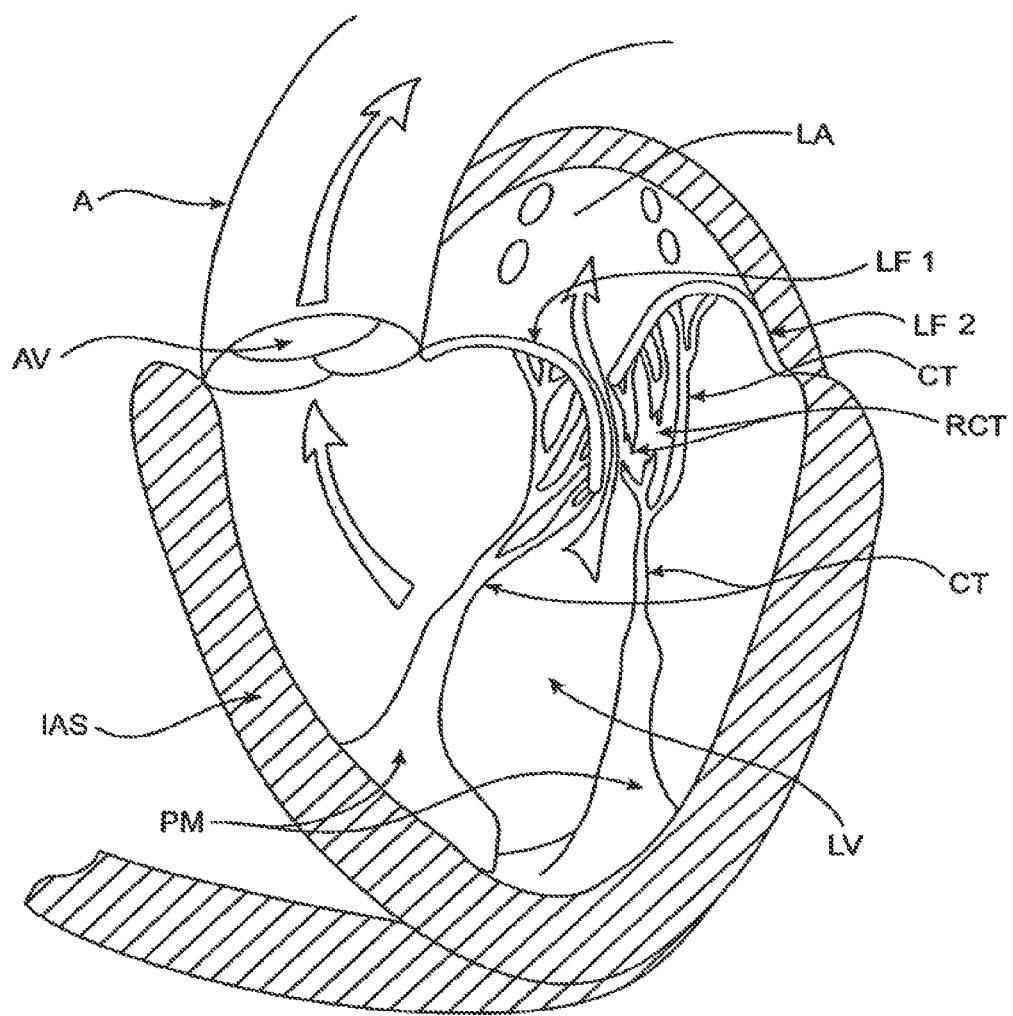
FIG. 2 is a schematic illustration of the left ventricle of a heart having prolapsed leaflets in the mitral valve.
Figure 3:
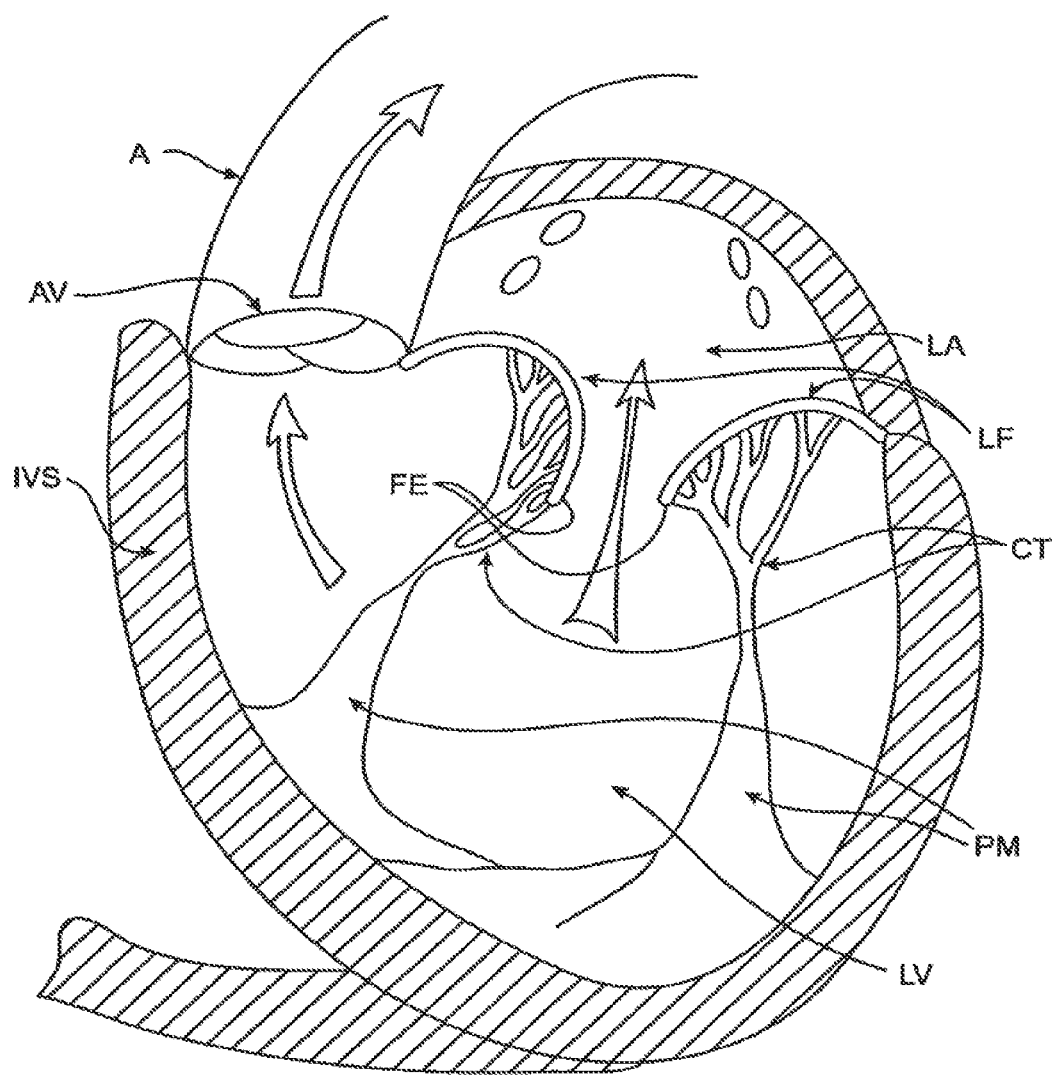
FIG. 3 is a schematic illustration of a heart in a patient suffering from cardiomyopathy where the heart is dilated and the leaflets do not meet.
Figure 4:
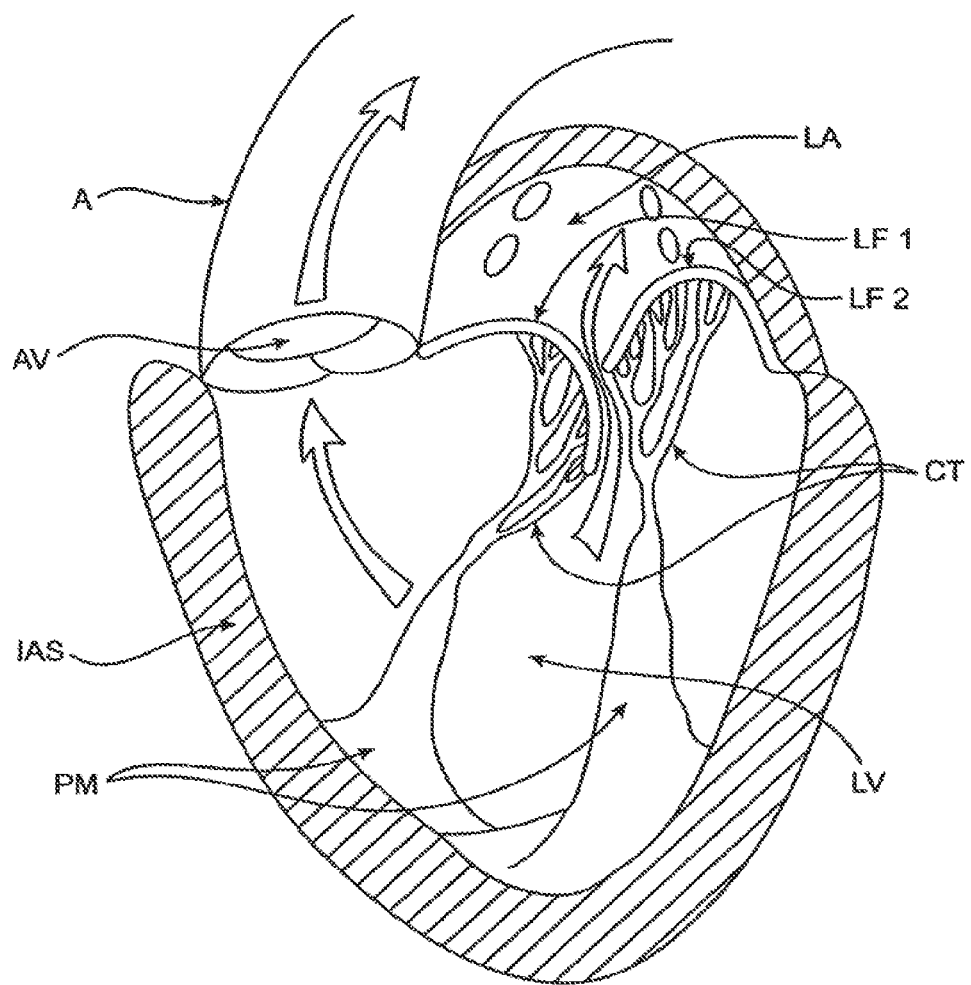
FIG. 4 illustrates mitral valve regurgitation in the left ventricle of a heart having impaired papillary muscles.

Referring now to FIGS. 2-4, a number of structural defects in the heart can cause mitral prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
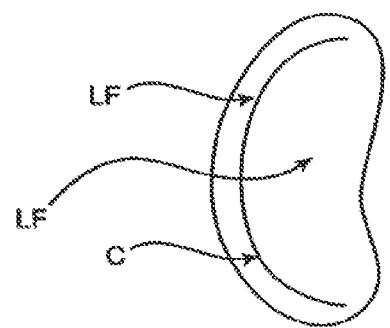
FIG. 3A shows normal closure of the leaflets.
Figure 3B:
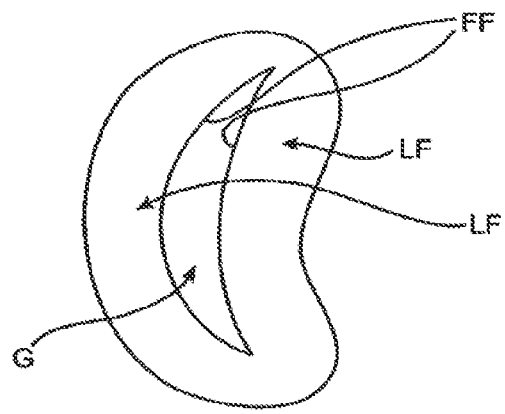
FIG. 3B shows abnormal leaflet closure in the dilated heart.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
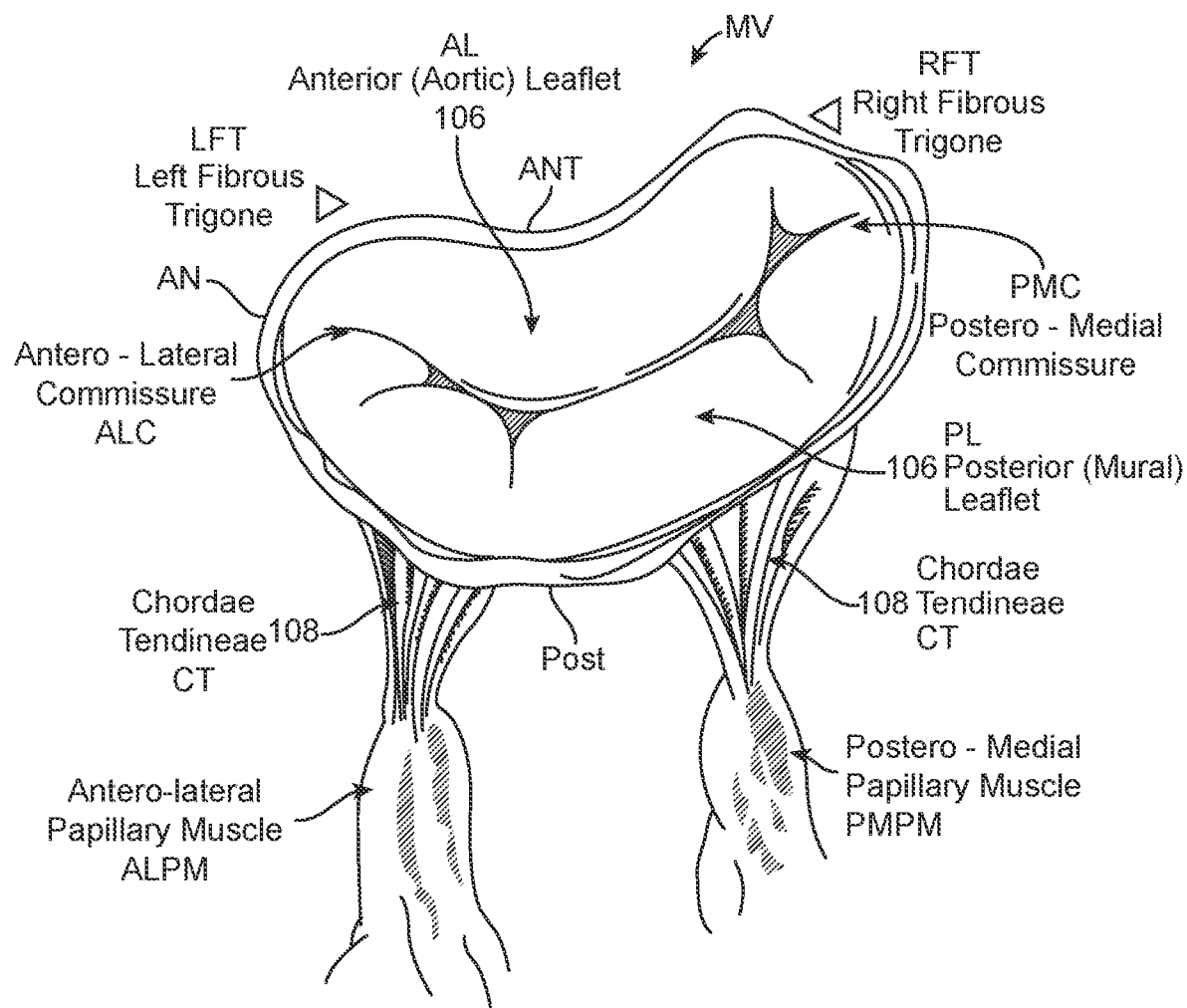
FIGS. 5A-5B illustrate basic anatomy of the mitral valve.
Figure 5B:
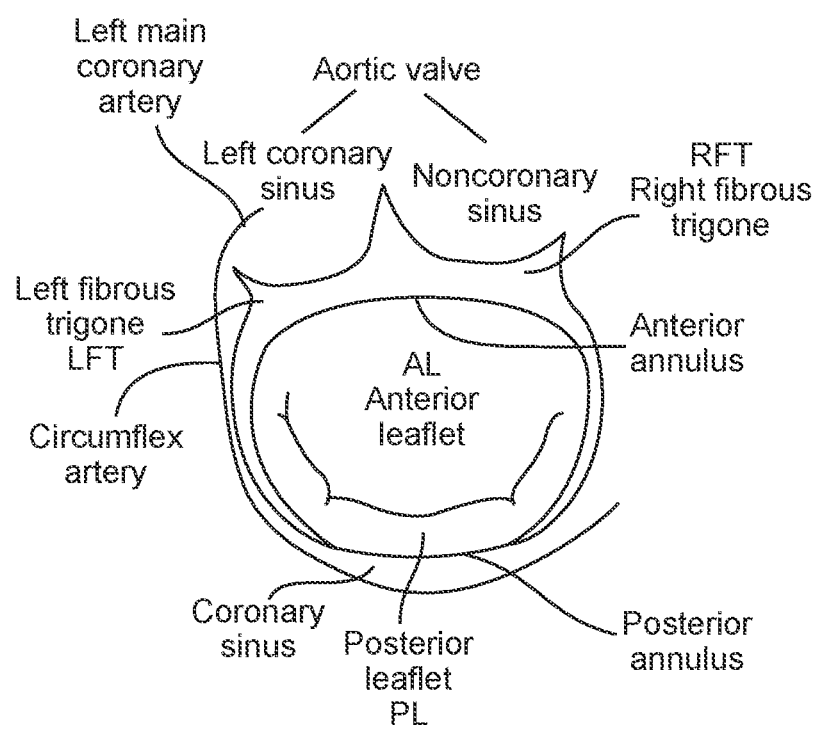

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted by generally by the solid triangles. FIG. 5B more clearly illustrates the left and right fibrous trigones, LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices and methods for treating mitral regurgitation. While the examples disclosed herein are directed to an implantable prosthetic mitral valve for treating mitral regurgitation, one of skill in the art will appreciate that this is not intended to be limiting, and the device and methods disclosed herein may also be used to treat other cardiac valves such as the tricuspid valve, aortic valve, pulmonary valve, etc, as well as other valves in the body such as venous valves or non-vascular valves.

Prosthetic Valve

Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the valve to the patient's heart, and a valve mechanism, either a mechanical valve, a valve with animal tissue, or combinations thereof. The prosthetic valve once implanted, takes over for malfunctioning native valve, thereby reducing or eliminating valvar insufficiency. While some of these valves appear promising, there still is a need for improved valves. The following discloses examples of a prosthetic valve, a delivery system for the prosthetic valve, and methods of delivering the valve that may overcome some of the challenges associated with existing prosthetic valves.

Figure 6:
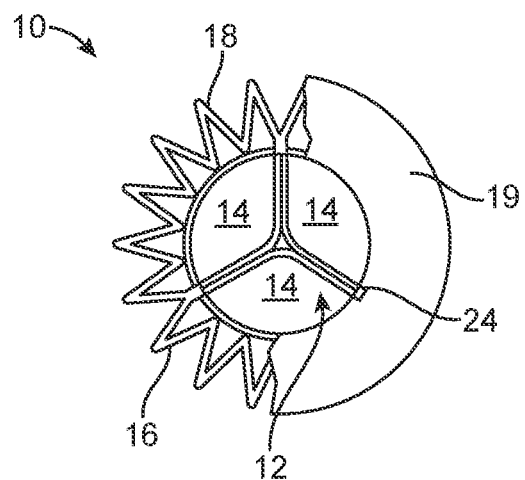
FIG. 6 illustrates a bottom, partial cross-sectional view of a prosthetic mitral valve.
Figure 7:
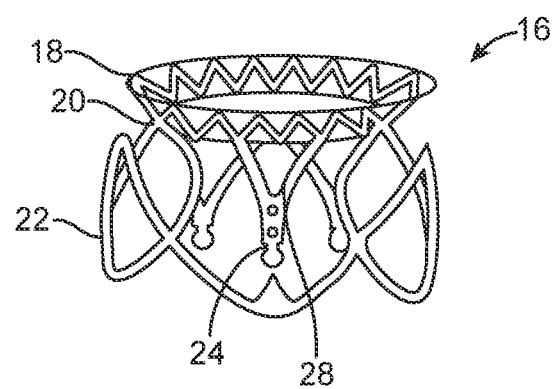
FIG. 7 is a perspective view of the anchor portion of the prosthetic mitral valve seen in FIG. 6.

Referring now to FIGS. 6-7, examples of a mitral valve prosthesis generally designated with reference numeral 10 comprise tricuspid tissue-type prosthetic one-way valve structure 12 comprising leaflets 14 affixed within self-expanding or expandable anchor portion 16 having a geometry that expands into low profile atrial skirt region 18, annular region 20, ventricular skirt region 22, and a plurality of leaflet commissures 24 (also referred to herein as commissure posts) extending axially in a cantilevered fashion downstream into the sub-annular space defined by ventricular skirt region 22.

FIG. 6 shows a partial cross-section of the valve 10 from the patient's left ventricle looking upward toward the right atrium. The atrial skirt region 18 is anchored to a lower portion of the right atrium 19. The valve leaflets 14 have an open position (not illustrated) and a closed position illustrated in FIG. 6. In the open position, the leaflets 14 are displaced away from one another to allow blood flow therepast, and in the closed position, the leaflets 14 engage one another to close the valve and prevent retrograde blood flow therepast. The valve commissures 24 may be configured to optimize the efficiency of the prosthetic valve structure 12 and the load distribution on the leaflets 14 by providing for the attachment of the leaflets 14 along arcuate seams 28 (best seen in FIG. 7), and by being made selectively flexible at different points or zones along their axial length through the addition/deletion of reinforcing struts.

FIG. 7 shows a perspective view of the anchor portion 16 of the valve 10 which has been formed from a series of interconnected struts. The atrial skirt region 18 forms an annular flanged region on the anchor to help secure an upper portion of the prosthetic valve in the atrium, and the annular region 20 is a cylindrical region for anchoring the valve along the native valve annulus. The ventricular skirt region 22 similarly is cylindrically shaped and helps anchor a lower portion of the valve in the patient's left ventricle. Any portion, or all of the anchor may be covered with tissue such as pericardium or other tissues disclosed herein, or a synthetic material such as Dacron or ePTFE may be used to cover the anchor. The covering helps to seal the anchor to the native valve, and this helps funnel blood into and through the prosthetic valve, rather than around the valve. In some examples, the anchor may remain uncovered. The prosthetic valve has an expanded configuration and a collapsed configuration. The collapsed configuration has a low-profile cylindrical shape that is suitable for mounting on a delivery system and delivery is preferably made either transluminally on a catheter, or transapically through the heart wall. The expanded configuration (as illustrated) allow the prosthetic valve to be anchored into a desired position.

Figure 8A:
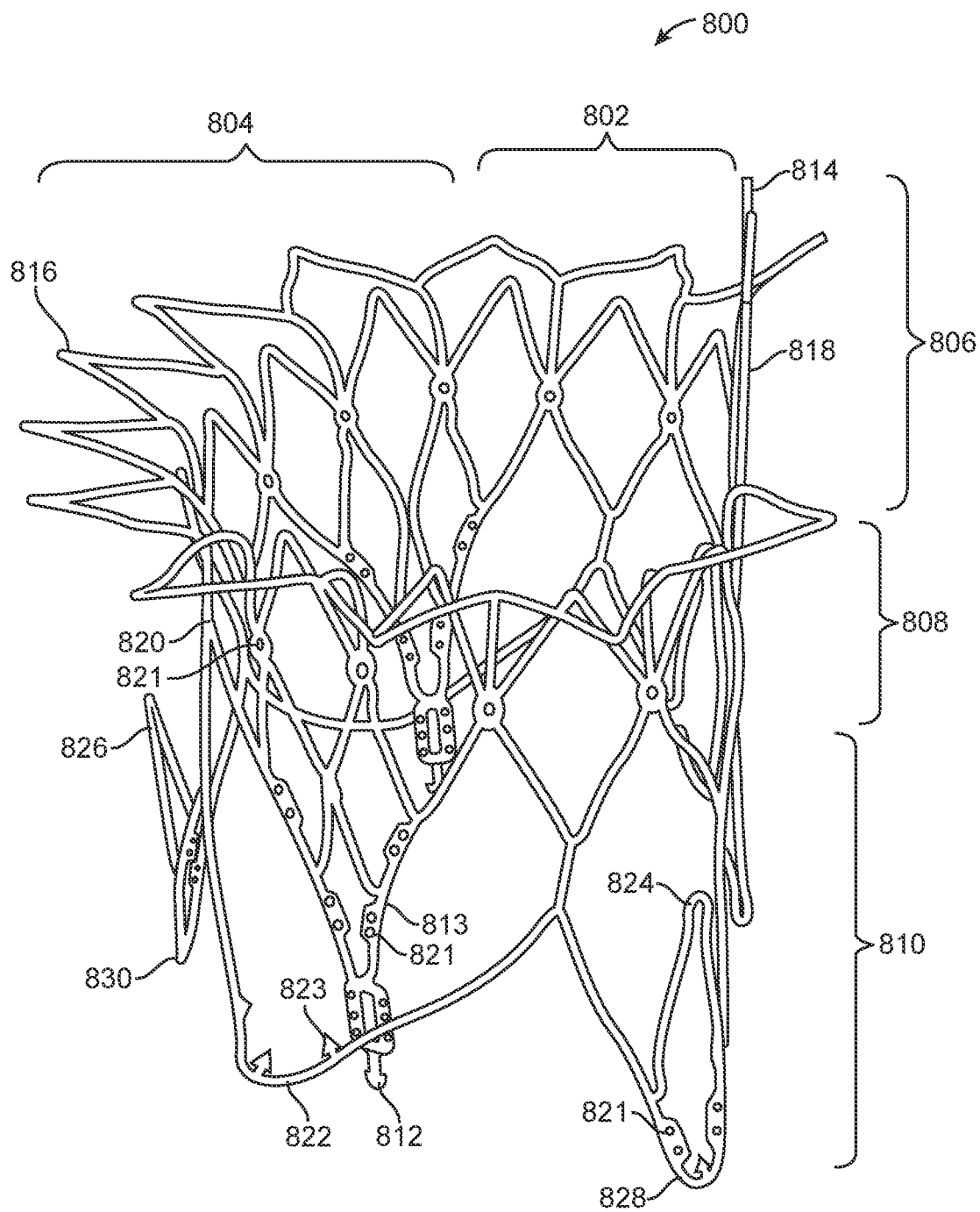
FIG. 8A is a perspective view of a prosthetic mitral valve.
Figure 8B:
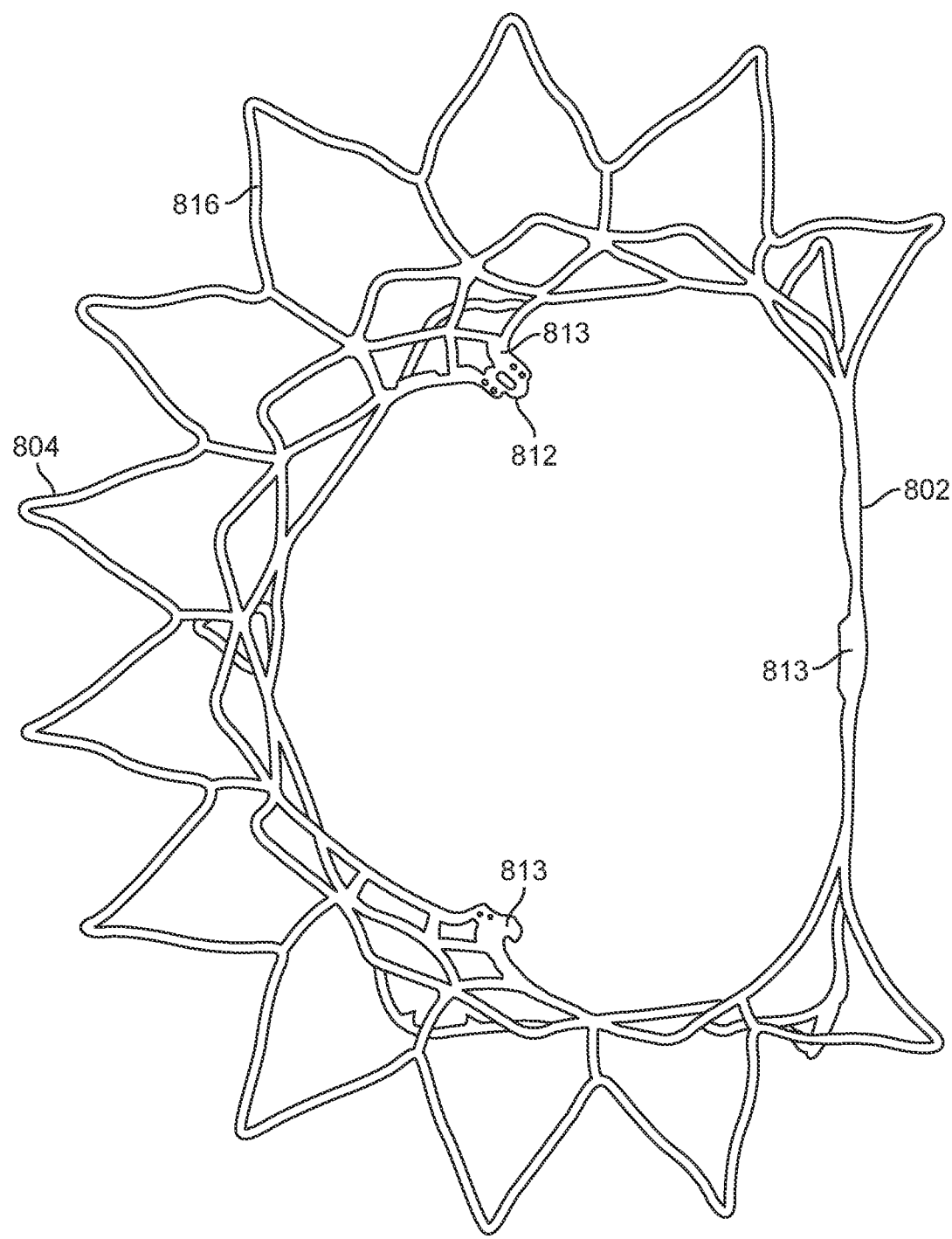
FIG. 8B is a top view from the atrium of the prosthetic valve in FIG. 8A.

FIG. 8A illustrates a perspective view of an example of a prosthetic mitral valve with optional coverings removed to allow visibility of the anchor struts and frame. FIG. 8B illustrates a top view of the prosthetic valve in FIG. 8A from the atrium looking down into the ventricle. The valve 800 includes an asymmetrical expanded anchor portion having a D-shaped cross-section. As shown, the anchor portion generally comprises anterior 802 and posterior 804 aspects along the longitudinal axis thereof, as well as atrial 806, annular 808 and ventricular 810 regions that correspond generally to the atrial skirt 18, annular 20 and ventricular skirt 22 regions of the example described above in FIGS. 6-7. Commissures (also referred to herein as commissure posts) 813 also correspond generally to the leaflets 14 of the example in FIGS. 6-7. The prosthetic valve 800 has a collapsed configuration and an expanded configuration. The collapsed configuration is adapted to loading on a shaft such as a delivery catheter for transluminal delivery to the heart, or on a shaft for transapical delivery through the heart wall. The radially expanded configuration is adapted to anchor the valve to the patient's native heart adjacent the diseased or damaged valve. In order to allow the valve to expand from the collapsed configuration to the expanded configuration, the anchor portion of the valve may be fabricated from a self-expanding material such as a nickel titanium alloy like nitinol, or it may also be made from spring temper stainless steel, cobalt-chromium alloy, or a resilient polymer. In still other examples, the anchor may be expandable with an expandable member such as a balloon. In some examples, the anchor is fabricated by laser cutting, electrical discharge machining (EDM), or photochemically etching a tube. The anchor may also be fabricated by photochemically etching a flat sheet of material which is then rolled up with the opposing ends welded together.

The atrial skirt portion 816 forms a flanged region that helps to anchor the prosthetic valve to the atrium, above the mitral valve. The atrial skirt includes a plurality of triangular fingers which extend radially outward from the anchor to form the flange. The posterior 804 portion of the atrial skirt 816 is generally round or circular, while a portion of the anterior 802 part of the atrial skirt 816 is flat. Thus, the atrial skirt region may have a D-shaped cross-section. This allows the prosthetic valve to conform to the patient's cardiac anatomy without obstructing other portions of the heart, as will be discussed below. Each triangular finger is formed from a pair of interconnected struts. The triangular fingers of the atrial skirt generally are bent radially outward from the central axis of the prosthetic valve and lie in a plane that is transverse to the valve central axis. In some examples, the atrial skirt lies in a plane that is substantially perpendicular to the central axis of the valve. The anterior portion 802 of the atrial skirt 806 optionally includes an alignment element 814 which may be one or more struts which extend vertically upward and substantially parallel to the prosthetic valve. The alignment element 814 may include radiopaque markers (not illustrated) to facilitate visualization under fluoroscopy. The alignment element helps the physician to align the prosthetic valve with the native mitral valve anatomy, as will be discussed later.

Disposed under the atrial skirt region is the annular region 820 which also has a collapsed configuration for delivery, and an expanded configuration for anchoring the prosthetic valve along the native valve annulus. The annular region is also comprised of a plurality of interconnected struts that form a series of cells, either closed cells or open cells. Suture holes 821 in some of the struts allow tissue or other coverings (not illustrated) to be attached to the annular region. Covering all or a portion of the anchor with tissue or another covering helps seal the anchor against the heart valve and adjacent tissue, thereby ensuring that blood is funneled through the valve, and not around it. The annular region may be cylindrical, but in some examples has a posterior portion 804 which is circular, and an anterior portion 802 which is flat, thereby forming a D-shaped cross-section. This D-shaped cross-section conforms better to the native mitral valve anatomy without obstructing blood flow in other areas of the heart.

The lower portion of the prosthetic valve includes the ventricular skirt region 828. The ventricular skirt region also has a collapsed configuration for delivery, and an expanded configuration for anchoring. It is formed from a plurality of interconnected struts that form a series of cells, preferably closed, that can radially expand. The ventricular skirt in the expanded configuration anchors the prosthetic valve to the ventricle by expanding against the native mitral valve leaflets. Optional barbs 823 in the ventricular skirt may be used to further help anchor the prosthetic valve into the ventricular tissue. Barbs may optionally also be included in the atrial skirt portion as well as the annular region of the anchor. Additionally, optional suture holes 821 in the ventricular skirt may be used to help suture tissue or another material to the ventricular skirt region, similarly as discussed above. The anterior 802 portion of the ventricular skirt may be flat, and the posterior 804 portion of the ventricular skirt may be circular, similarly forming a D-shaped cross-section to anchor and conform to the native anatomy without obstructing other portions of the heart. Also, the lower portions of the ventricular skirt serve as deployment control regions since the lower portions can remain sheathed thereby constraining the ventricular skirt from radial expansion until after the optional ventricular trigonal tabs and posterior tab have expanded, as will be explained in greater detail below.

The ventricular skirt portion may optionally also include a pair of ventricular trigonal tabs 824 on the anterior portion of the anchor (only 1 visible in this view) for helping to anchor the prosthetic valve as will be discussed in greater detail below. The ventricular skirt may also optionally include a posterior tab 826 on a posterior portion 804 of the ventricular skirt for anchoring the prosthetic valve to a posterior portion of the annulus. The trigonal tabs 824 or the posterior tab 826 are tabs that extend radially outward from the anchor, and they are inclined upward in the upstream direction.

The actual valve mechanism is formed from three commissure posts (also referred to as commissures) 813 which extend downstream substantially parallel with the longitudinal axis of the prosthetic valve or radially inward toward the central axis of the anchor in a funnel or cone-like shape. The commissures 813 are formed from a plurality of interconnected struts that create the triangular shaped commissures. The struts of the commissures may include one or more suture holes 821 that allow tissue or a synthetic material to be attached to the commissures. In this example, the valve is a tricuspid valve, therefore it includes three commissures 813. The tips of the commissures may include a commissure tab 812 (also referred to as a tab) for engaging a delivery catheter. In this example, the tabs have enlarged head regions connected to a narrower neck, forming a mushroom-like shape. The commissures may be biased in any position, but preferably angle inward slightly toward the central axis of the prosthetic valve so that retrograde blood flow forces the commissures into apposition with one another to close the valve, and antegrade blood flow pushes the commissures radially outward, to fully open the valve. FIG. 8B is a top view illustrating the prosthetic valve of FIG. 8A from the atrial side, and shows the preferred D-shaped cross-section.

Figure 9A:
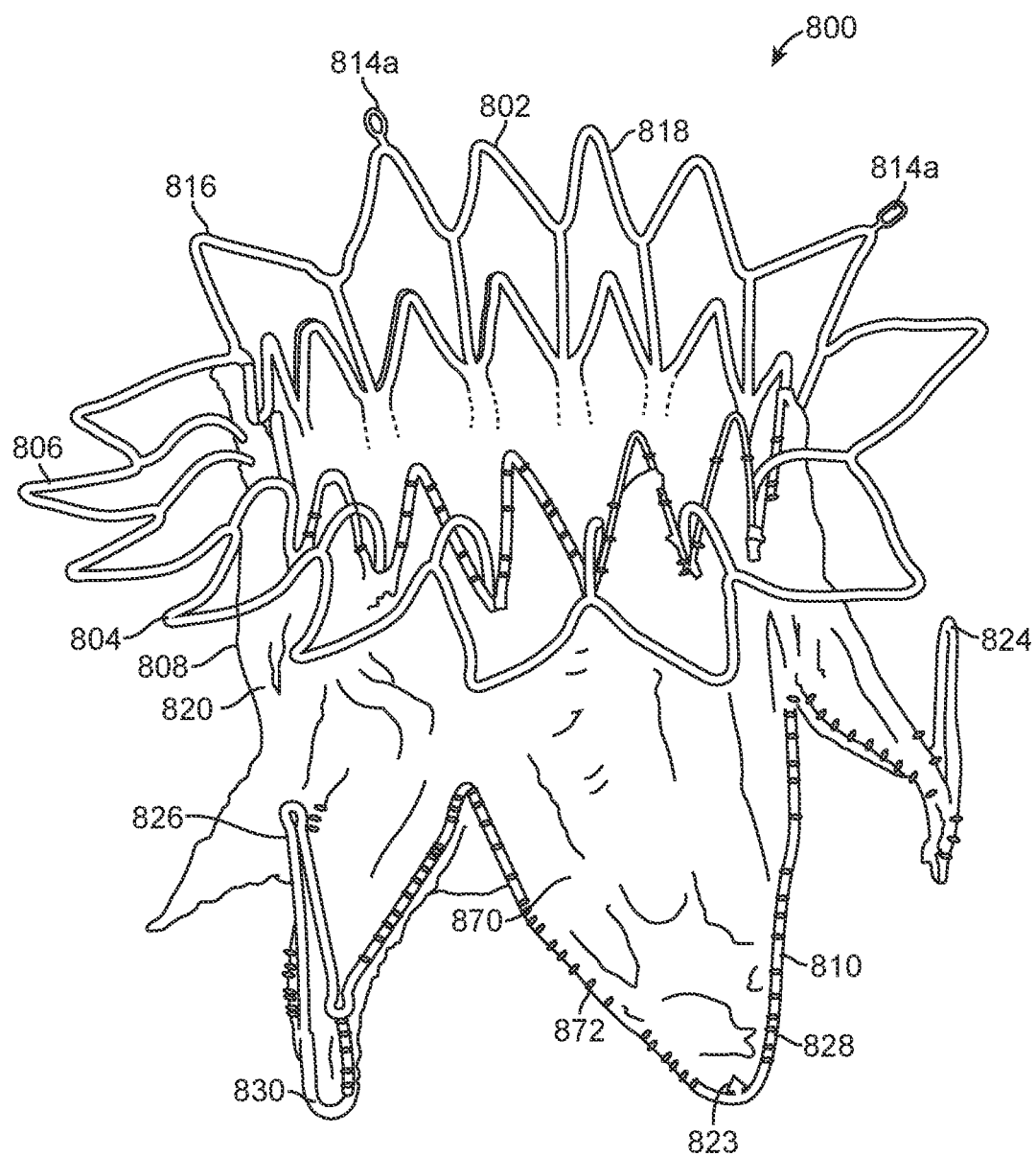
FIG. 9A illustrates a perspective view of the prosthetic valve in FIG. 8A from the atrium.

FIG. 9A illustrates the prosthetic mitral valve of FIGS. 8A-8B with a covering 870 coupled to portions of the anchor with suture 872. This view is taken from an atrial perspective. In this example, the covering may be pericardium which may come from a number of sources as disclosed elsewhere in this specification. In alternative examples, the covering may be a polymer such as Dacron polyester, ePTFE, or another synthetic material. The covering is may be disposed over the annular region 820 and the ventricular skirt region 828, and in some example the anterior ventricular trigonal 824 tabs and the ventricular posterior tab 830 may also be covered with the same or a different material. The covering helps seal the anchor against the adjacent tissue so that blood funnels through the valve mechanism. In this example, the atrial skirt is left uncovered, as well as tabs 824, 830. Additionally, radiopaque markers 814*a* form a portion of the alignment element and facilitate visualization of the prosthetic valve under fluoroscopy which is important during alignment of the valve.

Figure 9B:
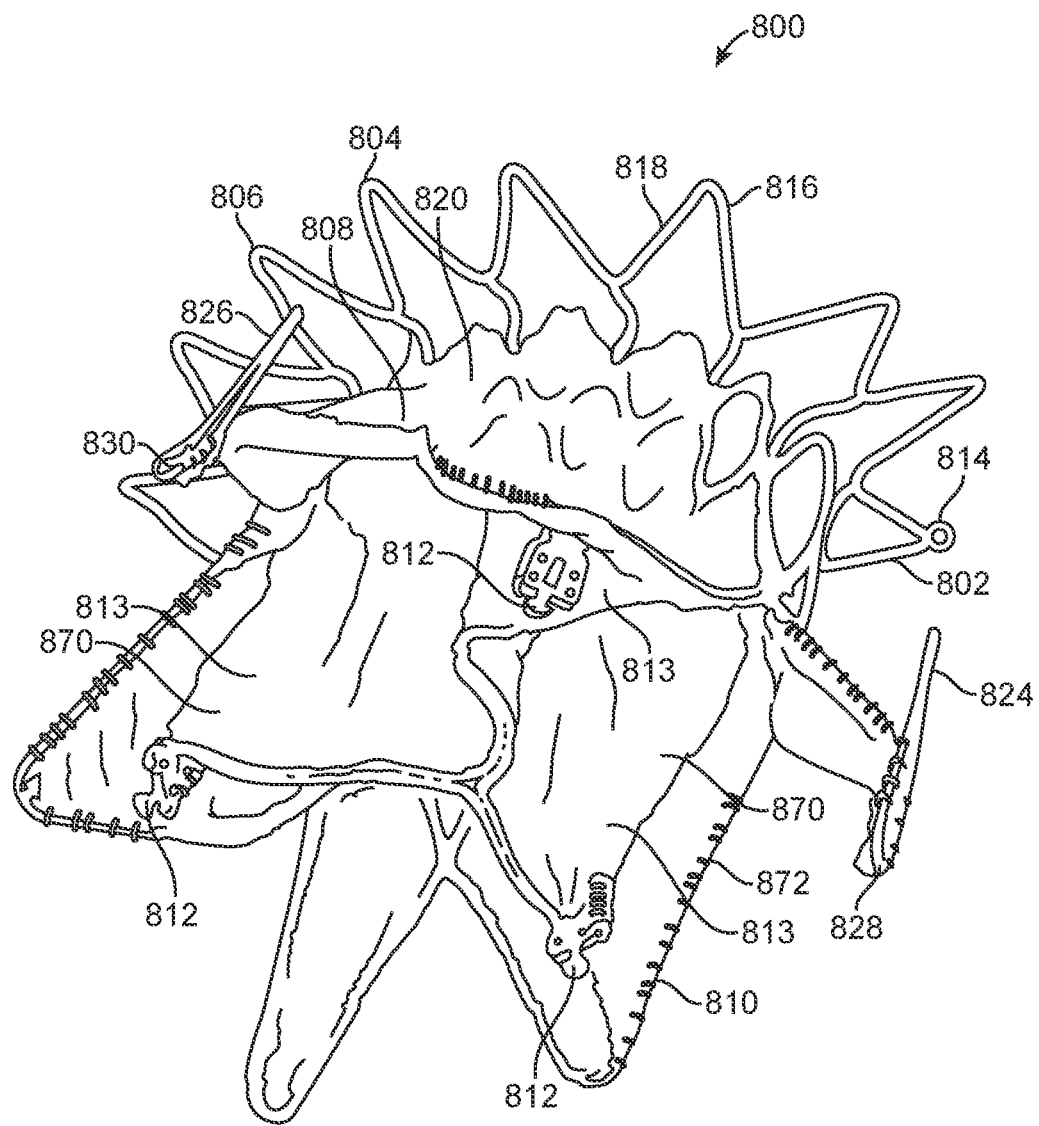
FIG. 9B illustrates a perspective view of the prosthetic valve in FIG. 8A from the ventricle.

FIG. 9B is a perspective view of the prosthetic mitral valve seen in FIG. 9A, as seen from the ventricle. The struts of the valve commissures are covered with the same material or a different material as the annular and ventricular regions as discussed above, thereby forming the tricuspid valve leaflets 813. FIG. 9B shows the valve in the closed configuration where the three leaflets are engaged with one another preventing retrograde blood flow. Commissure tabs 812 remain uncovered and allow the commissures to be coupled with a delivery device as will be explained below. The prosthetic valve in FIGS. 9A-9B may be sterilized so they are suitable for implantation in a patient using methods known in the art.

Figure 10:
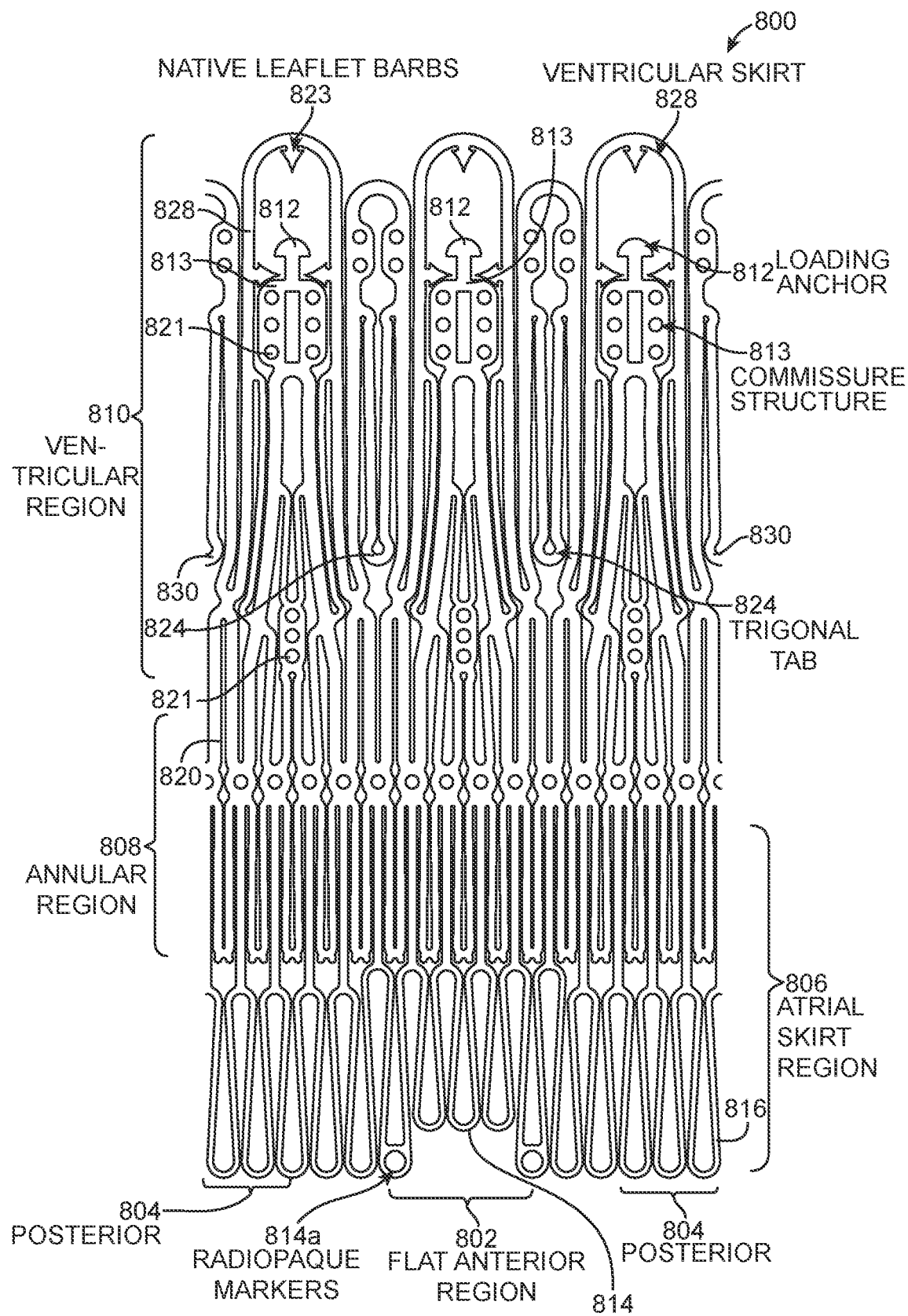
FIG. 10 illustrates the prosthetic valve of FIG. 8A uncovered and unrolled in a flat unexpanded pattern.

FIG. 10 illustrates the prosthetic valve of FIG. 9A with the covering removed, and the remaining anchor unrolled, unexpanded and flattened out. The prosthetic valve 800 is formed from a plurality of interconnected struts. For example, the atrial skirt region 806 includes a plurality of interconnected struts that form a series of peaks and valleys. The flat anterior region 802 of the prosthetic valve has its peaks and valleys axially offset from those of the remaining portion of the atrial skirt, and this region becomes a part of the alignment element 814. Radiopaque markers 814*a* are disposed on either side of the offset peaks and valleys and help with visualization during implantation of the valve. An axially oriented connector joins the struts of the skirt region 806 with the struts of the annular region 808. The annular region is also comprised of a plurality of axially oriented and interconnected struts that form peaks and valleys. Connector struts couple struts of the annular region with the struts of the ventricular region 810. The ventricular region also includes a plurality of interconnected struts that form peaks and valleys. Additionally, the struts form the leaflet commissures 813, the ventricular skirt 828, as well as the trigonal and posterior tabs 824, 830. Suture holes 821 are disposed along the struts of the annular region as well as the ventricular region to allow attachment of a cover such as pericardium or a polymer such as Dacron or ePTFE. Barbs 823 are disposed along the ventricular skirt 828 to help anchor the prosthetic valve to adjacent tissue.

Commissure tabs or tabs 812 are disposed on the tips of the commissures 813 and may be used to releasably couple the prosthetic valve with a delivery system as will be described below. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting.

Once the flat anchor pattern has been formed by EDM, laser cutting, photochemical etching, or other techniques known in the art, the anchor is radially expanded into a desired geometry. The anchor is then heat treated using known processes to set the shape. Thus, the anchor may be loaded onto a delivery catheter in a collapsed configuration and constrained in the collapsed configuration with a constraining sheath. Removal of the constraining sheath will allow the anchor to self-expand into its unbiased pre-set shape. In other example, an expandable member such as a balloon may be used to radially expand the anchor into its preferred expanded configuration.

Delivery Systems

FIGS. 11-15C show a delivery apparatus 1124 fashioned to deliver a prosthetic mitral valve to the heart transapically.

However, one of skill in the art will appreciate that the delivery system may be modified and relative motion of the various components adjusted to allow the device to be used to deliver a prosthetic mitral valve transseptally. The delivery apparatus is generally comprised of a handle 1101 that is the combination of a handle section 1102 and a handle section 1103 (best seen in FIG. 12), as well as a flexible tip 1110 that can smoothly penetrate the apex of the heart, and a sheath catheter 1109 which houses several additional catheters that are designed to translate axially and will be described in detail below.

The handle 1101 includes a female threaded Luer adaptor 1113 which connects to a Tuohy Borst adaptor 1114 in order to provide a hemostatic seal with a 0.035" diameter guide wire (not shown). The female threaded Luer adaptor 1113 is in threaded contact with the proximal section of the handle 1101 through a threaded port 1131 (best seen in FIG. 12).

Figure 11:
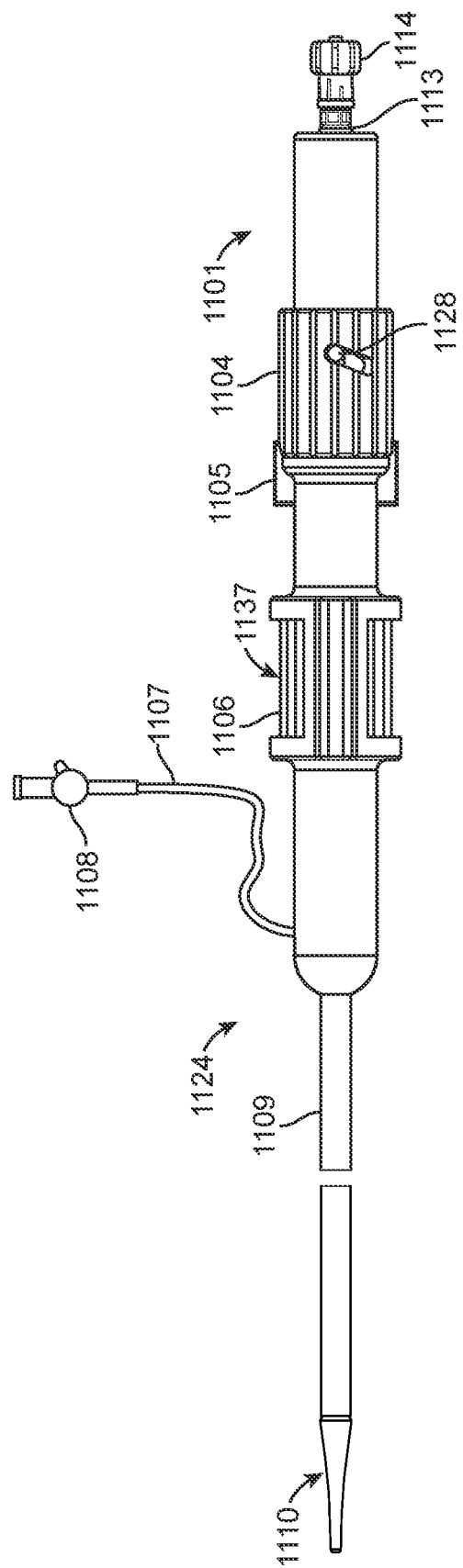
FIG. 11 is a side view of a delivery device for implantation of a prosthetic valve.

As can be seen in FIG. 11, the handle 1101 provides location for the control mechanisms used to position and deploy a prosthetic mitral valve. The handle 1101 provides housing for a thumbwheel 1106 that can be accessed through a window 1137 that appears on both the top and bottom of the handle 1101. The thumbwheel 1106 internally mates with a threaded insert 1115 (best seen in FIG. 12) that actuates the sheath catheter 1109, and the mechanics of this interaction will be explained in detail below.

FIG. 11 also shows a deployment thumbwheel 1104 that provides linear translation to a deployment catheter 1120 (best seen in FIG. 12) when turned, since the turning motion of the deployment thumbwheel 1104 acts as a power screw, pushing the peg 1128 forward and distally from the user. The mechanics behind the peg 1128 will be further detailed below. The thumbwheel lock 1105 provides a security measure against unwanted rotation of the deployment thumbwheel 1104 by acting as a physical barrier to rotation. In order to turn the deployment thumbwheel 1104 the user must push forward the thumbwheel lock 1105, disengaging it from two slots 1147 (seen in FIG. 12) in the deployment thumbwheel 1105.

As can also be seen in FIG. 11, a bleed valve 1108 and fluid line 1107 are connected to an internal mechanism in the distal portion of the handle 1101, which provides a hemostatic seal for the sheath catheter 1109. The details of this connection will be described below.

Figure 12:
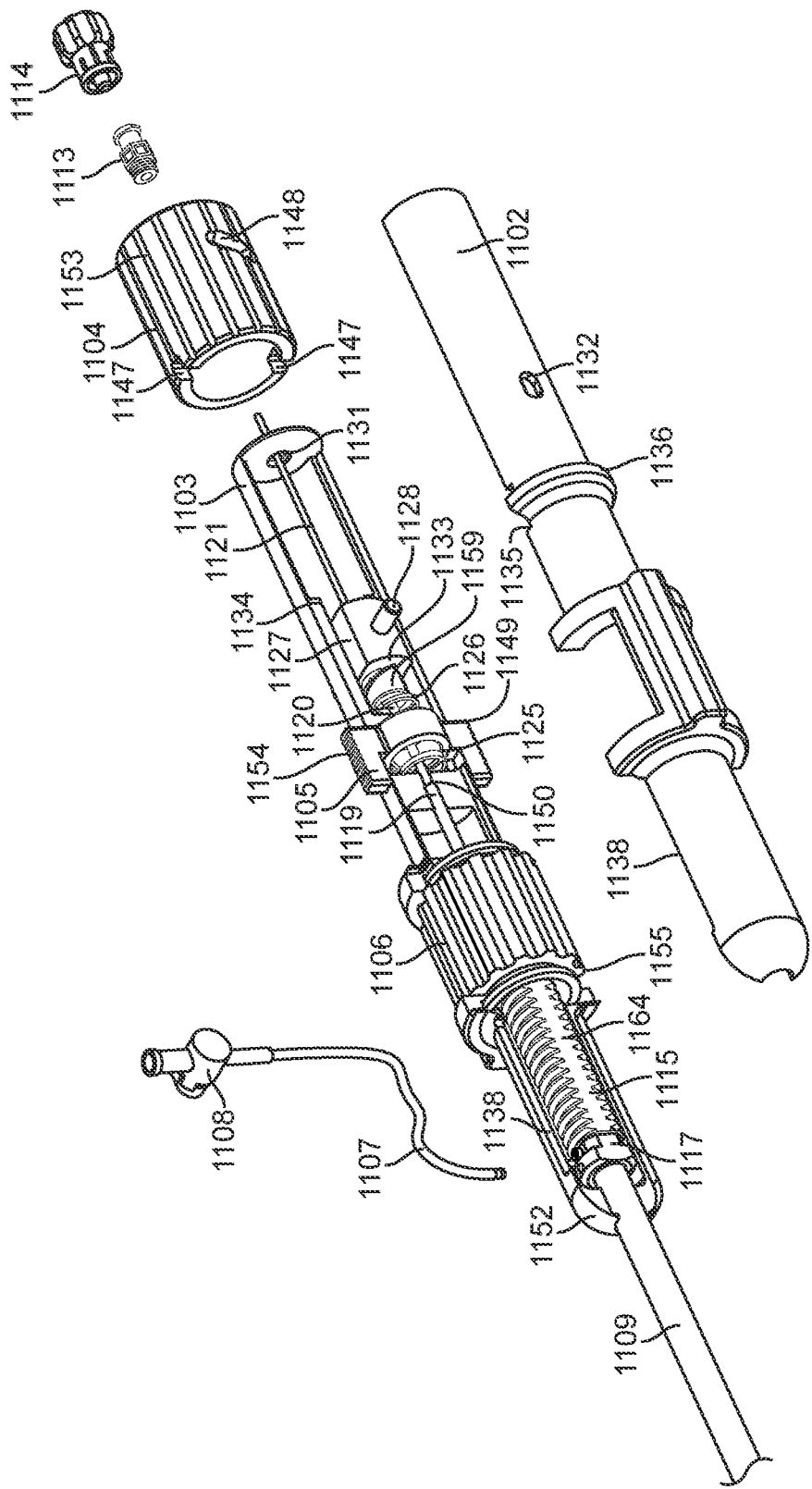
FIG. 12 is a perspective exploded view of a proximal portion of the delivery device in FIG. 11.

Internal mechanics of the delivery apparatus 1124 are illustrated in detail in FIG. 12, and the following descriptions will reveal the interactions between individual components, and the manner in which those components combine in order to achieve a prosthetic heart valve delivery apparatus.

As seen in FIG. 12, a handle section 1103 and handle section 1102 combine to create a handle 1101 that forms the basis of the delivery apparatus 1124. In order to advance the sheath catheter 1109 during valve loading, or retract the sheath catheter 1109 during deployment, a rotatable thumbwheel 1106 is in threaded contact (internal threads 1129 seen in FIG. 14) with a threaded insert 1115 (external threads 1130 of FIG. 13) that translates linearly along the axis of the delivery apparatus, from a proximal position to a distal position. The sheath catheter 1109 is in mating contact with the threaded insert 1115 and is fastened through the use of a collar 1117 that aligns and mates the collar with the insert. The collar 1117 is fastened with screws 1116 (best seen in DETAIL A in FIG. 14) to the threaded insert 1115 and contains a fluid port 1142 (best seen in DETAIL A in FIG. 14) that provides location for the fluid line 1117 so that hemostasis can be maintained between the patient and delivery apparatus. An O-ring 1118 (best seen in DETAIL A in FIG. 14) seals the stationary catheter 1119 (best seen in FIG. 14) against the sheath catheter 1109. The fluid line 1107 also provides a means of visually locating the sheath catheter 1109 with respect to position, as a slot 1138 in the handle 1101 allows the fluid line 1107 to translate with the sheath catheter 1109 (through a hole 1151 (best seen in DETAIL A in FIG. 14) during operation, and this translation is highly visible. In order to prevent rotation of the threaded insert during translation, a flat face 1164 has been machined onto both sides of the threaded insert 1115. The flat faces 1164 remain in contact with bosses 1139 and 1140 that are located on both handle section 1102 and handle section 1103 so that the bosses 1139 and 1140 act to grip the threaded insert 1115 and prevent rotation. A textured pattern 1155 allows the user to easily turn the thumbwheel 1106 in the surgical field. Detents 1141 (best seen in FIG. 14) locate flanges 63 (seen in FIG. 14) on the thumbwheel 1116 in order to allow for rotation.

The manner in which individual catheters (there are four catheters) move with respect to each other is illustrated in FIG. 12. Sheath catheter 1109 provides housing for the stationary catheter 1119, which in turn provides housing for the movable hub catheter 1120. The hub catheter 1120 translates linearly with respect to the nose catheter 1121 which can also be translated with respect to each previous catheter, and the handle 1101. The stationary catheter 1119 is mated to a handle section 1103 in an internal bore 1150 which also forms a seal between the stationary catheter 1119 and the hub catheter 1120. The distal portion of the stationary catheter 1119 is formed in the shape of a bell 1122 (see DETAIL A in FIG. 15A) which acts as a housing to retain the hub capture 1123 (seen in DETAIL A in FIG. 15A).

As previously stated a thumbwheel lock 1105 prevents rotation of the deployment thumbwheel 1104. In order to provide a seating force that keeps the thumbwheel lock 1105 in a locked position until manipulated, a spring 1125 is housed in an internal bore 62 (best seen in FIG. 14) and abuts against a shoulder 1161 (best seen in FIG. 14) that is located inside the thumbwheel lock 1105. This spring 1125 maintains the leading edge 1149 of the thumbwheel lock 1105 in a locked position within the two slots 1147 of the deployment thumbwheel 1104. Gripping texture 1154 is provided on the thumbwheel lock 1105 for ease of use. In order to locate and retain the thumbwheel lock 1105 inside of the handle 1101, a slot 1135 has been provided in both a handle section 1102 and a handle section 1103.

As shown in FIG. 12, a sliding block 1127 is housed inside of flat parallel faces 1134 which appear on the inside of the handle 1101. This sliding block 1127 is in mating contact with hub catheter 1120 and is the physical mechanism that linearly actuates the catheter. A spring 1126 is mounted on an external post 1159 and abuts against a shoulder 1133 that is located on the distal end of the sliding block 1127. This spring 1126 forces a peg 1128 (located inside a thru-hole 1156 of FIG. 14) into contact with the proximal edge of an angled slot 1148 that is cut into the deployment thumbwheel 1104. The deployment thumbwheel 1104 is contained between a shoulder 1136 and a snap ring (not shown), both of which are features of the handle 1101. Gripping texture 1153 on the deployment thumbwheel 1104 allows the user to easily rotate the thumbwheel in a clockwise direction, actuating the peg 1128 to ride distally along the slot 1148 and move the sliding block 1127, which pushes the hub catheter 1120 and hub 1123 (best seen in DETAIL A of FIG. 15A) forward and out of the bell 1122 (seen in DETAIL A of FIG. 15A). A slot 1132 appears in a handle section 1102 and a handle section 1103 and prevents the peg 1128 from translating beyond a desired range.

A nose catheter 1121 extends from a Tuohy Borst adaptor 1114 on the proximal end of the handle 1101, and internally throughout the handle and the respective catheters (sheath catheter 1109, stationary catheter 1119, and hub catheter 1120), terminating inside the rigid insert 1112 (seen in FIG. 15A) of the flexible tip 1110 (seen in FIG. 15A) that abuts with the distal end of the sheath catheter 1109.

Figure 13:
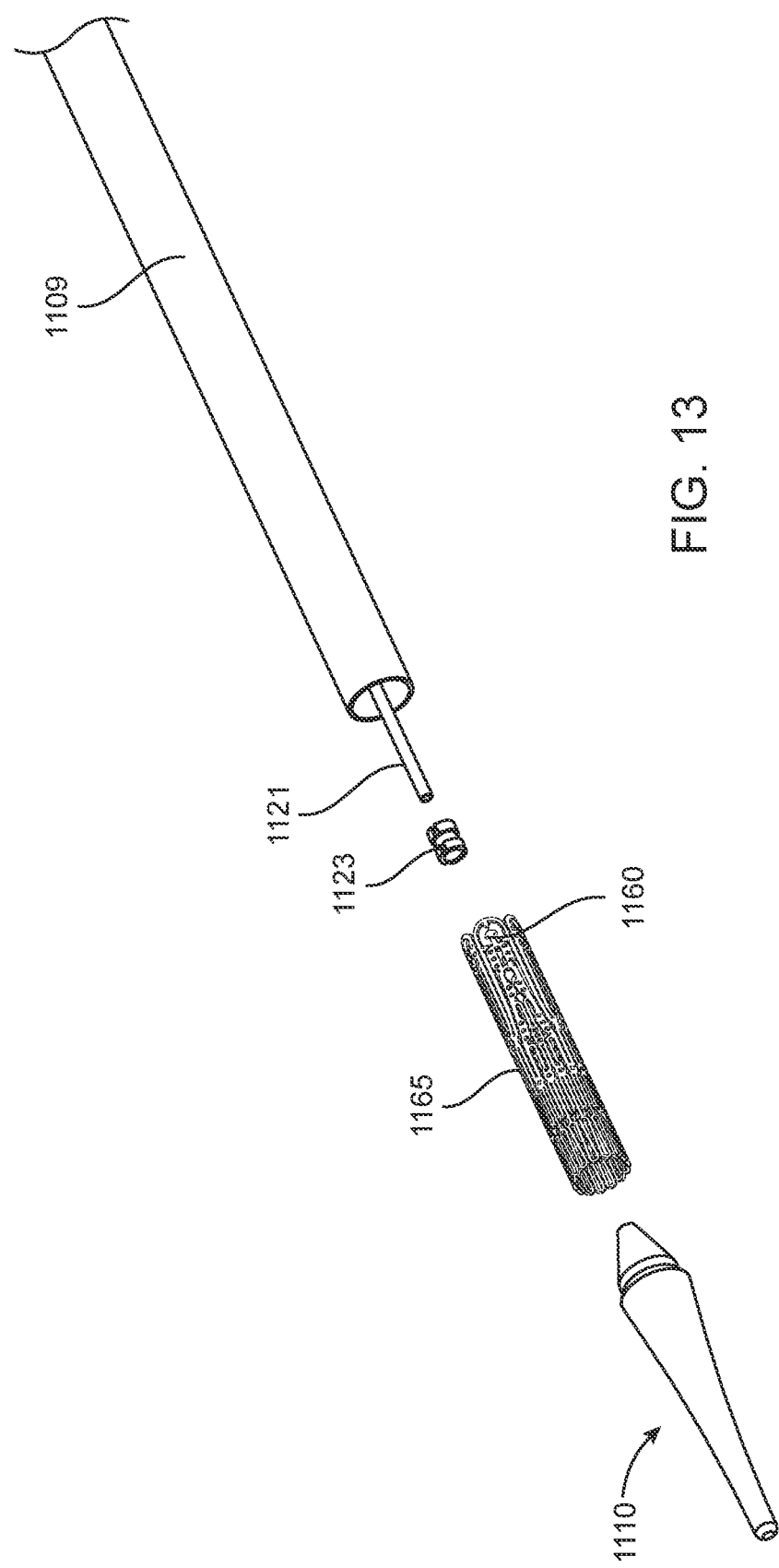
FIG. 13 is a perspective exploded view of a distal portion of the delivery device in FIG. 11.
Figure 14:
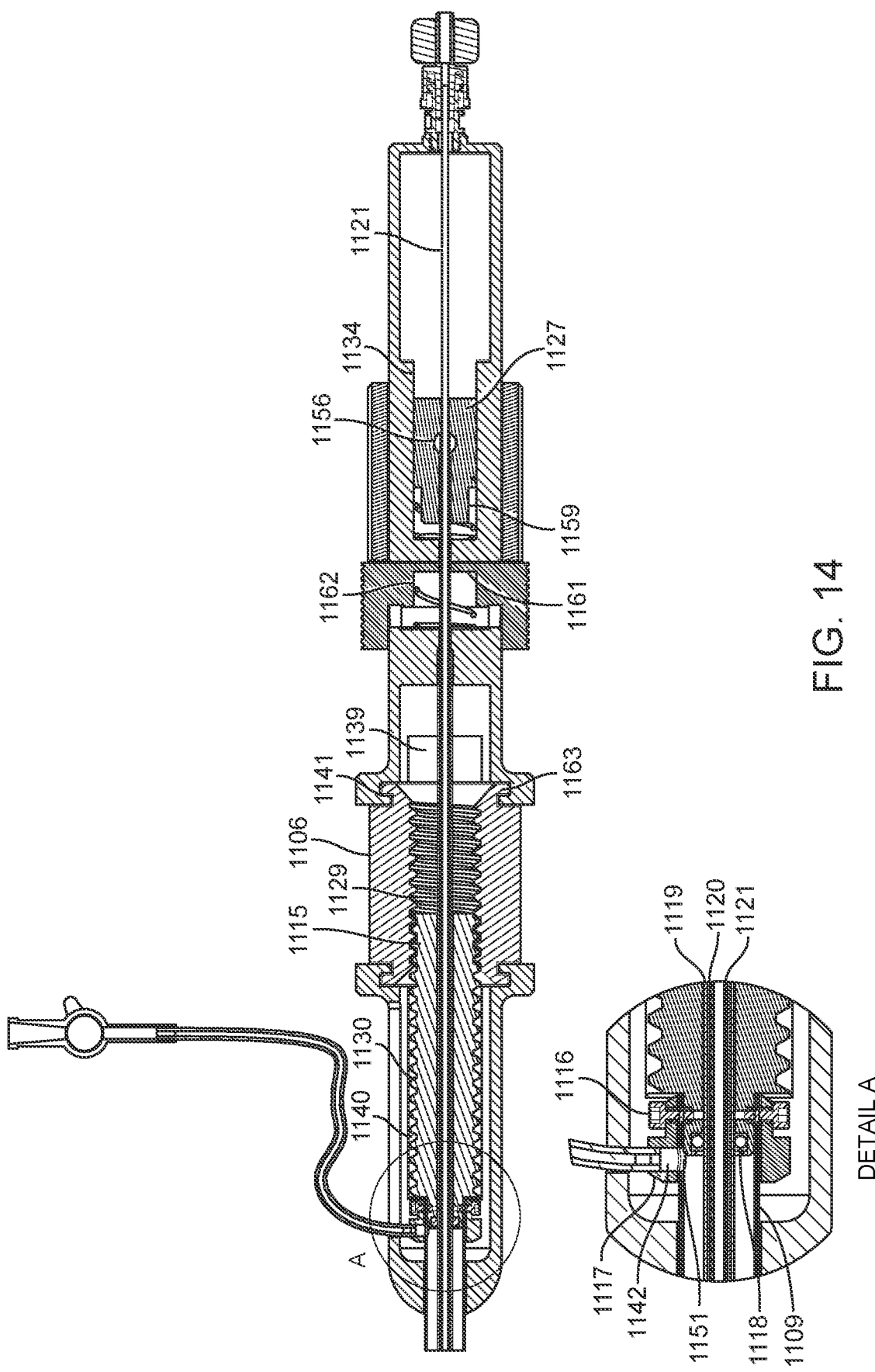
FIG. 14 is a cross-section of a proximal portion of the delivery device in FIG. 11.

FIG. 13 displays an exploded view of the tip section of the delivery apparatus 1124 and shows the relation between prosthetic mitral valve 1165 and the internal and external catheters. When crimped and loaded, the prosthetic mitral valve 1165 is encased between the internal surface of the sheath catheter 1109 and the external surface of the nose catheter 1121. In order to capture and anchor the prosthetic mitral valve 1165 within the delivery apparatus 1124, three commissure tabs 1160 (circumferentially spaced at about 120 degrees apart) appearing on the proximal end of the prosthetic mitral valve 1165 provide points of contact between the valve and three slots 1143 (seen in FIG. 15A) that are machined into the outer surface of the hub 1123 (circumferentially spaced at about 120 degrees apart). After first advancing the hub catheter 1120 (FIG. 15A) by rotating the deployment thumbwheel 1104 (seen in FIG. 12) clockwise, the three commissure tabs 1160 can be captured within the three slots 1143 (seen in FIG. 15A). The hub 1123 can then be retracted into the bell 1122 by releasing the deployment thumbwheel 1104 (seen in FIG. 12). In this position the prosthetic mitral valve 1165 is anchored to the delivery apparatus 1124, and further crimping of the valve will allow the sheath catheter 1109 to be advanced over the valve.

Figure 15A:
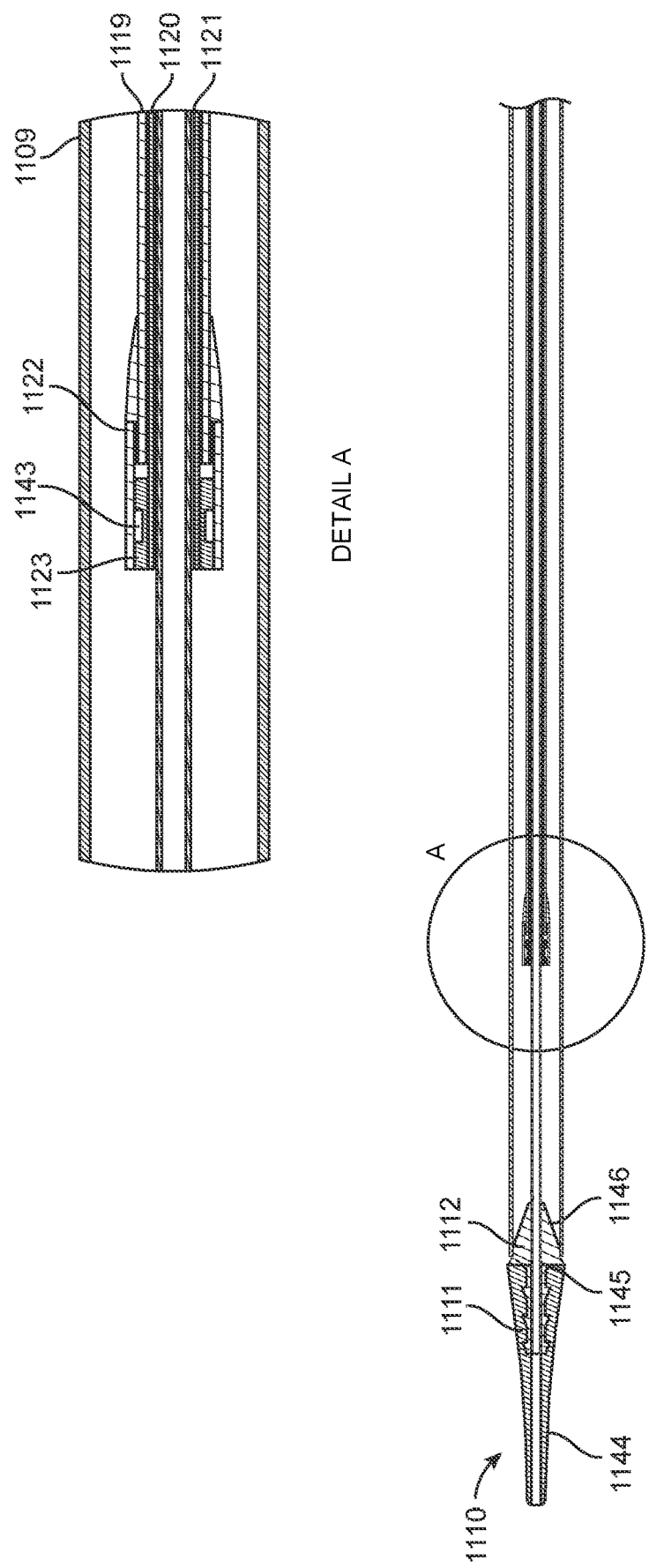
FIGS. 15A-15C are cross-sectional views of a distal portion of the delivery device in FIG. 11.
Figure 15B:
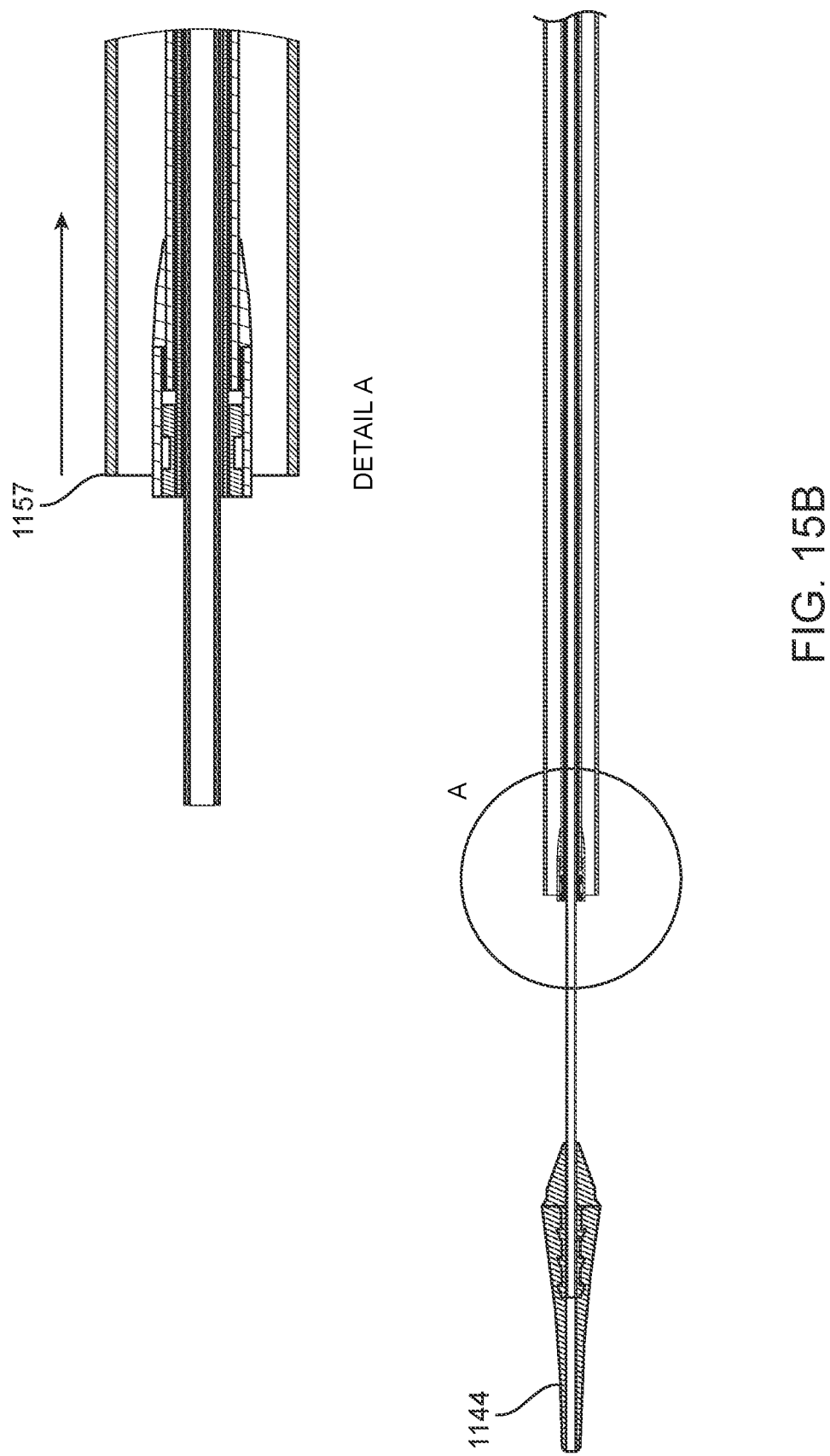
Figure 15C:
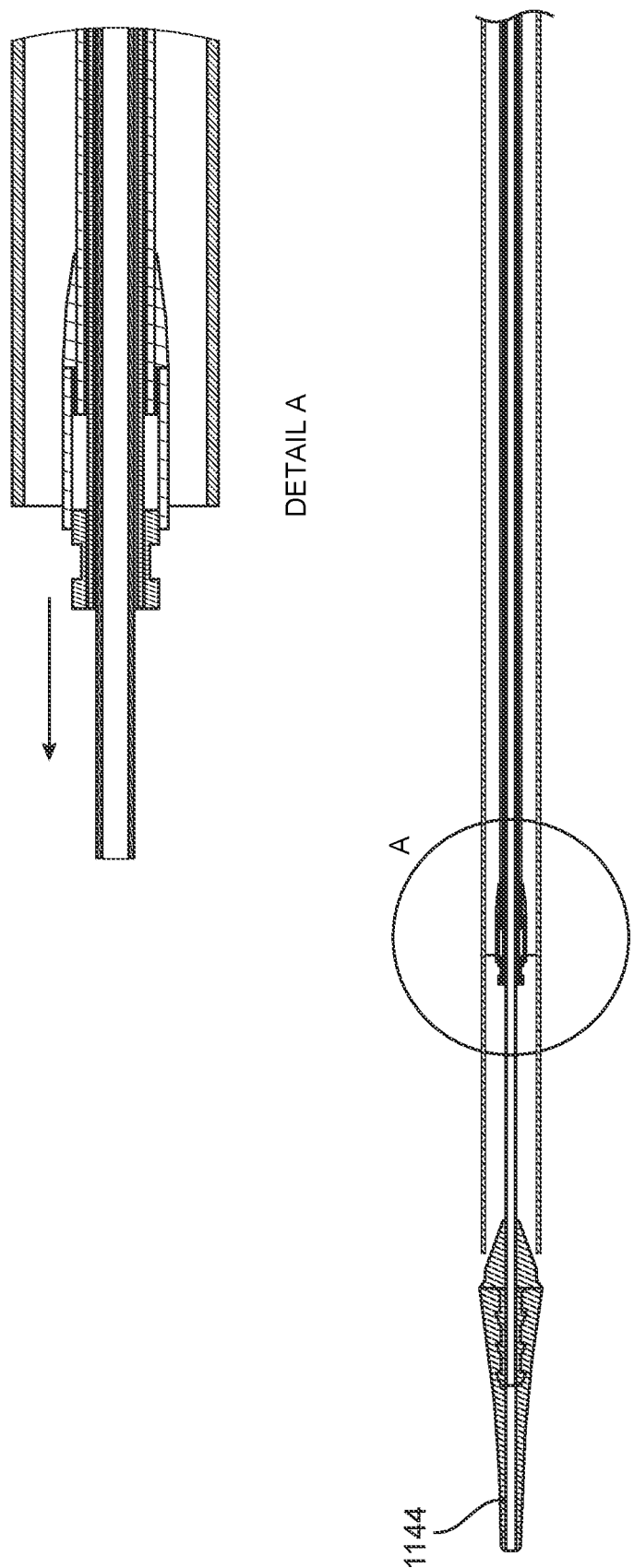

FIGS. 15A-15C further detail the manner in which loading of the prosthetic mitral valve 1165 (seen in FIG. 13) into the delivery apparatus 1124 can be achieved. Initially, the flexible tip 1110 is abutted against the distal edge 1157 of the sheath catheter 1109. The flexible tip 1110 is comprised of a rigid insert 1112, and a soft and flexible tip portion 1111 which is over-molded onto the rigid insert 1112. The shoulder 1145 and tapered face 1146 of the rigid insert 1112 act to guide and locate the distal edge 1157 of the sheath catheter 1109, so that the catheter may rest against and be stiffened by the flexible tip 1110, and be more easily introduced into the apex of the heart.

An initial position from which loading can be achieved is illustrated in FIG. 15A. As a first step in the loading of a prosthetic mitral valve 1165 (seen in FIG. 13) into the delivery apparatus 1124, the sheath catheter 1109 is withdrawn by rotation of the thumbwheel 1106 in a clockwise direction. The distal edge 1157 of the sheath catheter 1109 is retracted until it passes the distal edge of the bell 1122, as illustrated in DETAIL A of FIG. 15B. As a second step in the loading of a prosthetic mitral valve 1165 (seen in FIG. 13) into the delivery apparatus 1124, the hub 1123 is advanced from beneath the bell 1122 by clockwise turning of the deployment thumbwheel 1104 (seen in FIG. 12), as illustrated in DETAIL A of FIG. 15C. The deployment thumbwheel may only be turned once the thumbwheel lock 1105 (see FIG. 12) has been set in the forward position, disengaging it from contact with the thumbwheel. Advancement of the hub 1123 uncovers three slots 1143 into which three commissure tabs 1160 of the prosthetic mitral valve 1165 (seen in FIG. 13) will fit and be anchored. After anchoring of the commissure tabs 1160 into the slots 1143 by retraction of the hub 1123 has been achieved, a third step in the loading of a prosthetic mitral valve 1165 (seen in FIG. 13) into the delivery apparatus 1124 may be performed. The prosthetic mitral valve 1165 (seen in FIG. 13) can be crimped down to a minimum diameter by a loading mechanism (not shown), and then the sheath cannula 1109 can be advanced forward so as to cover the valve, by rotation of the thumbwheel 1106 in a counter-clockwise direction. The delivery apparatus 1124 and prosthetic mitral valve 1165 are then ready for deployment.

FIGS. 16-19B illustrate another example of a delivery device for implanting a prosthetic valve in the heart transapically. However, one of skill in the art will appreciate that the delivery system may be modified, and relative motion of the various components adjusted to allow the device to be used to deliver a prosthetic transseptally. The delivery apparatus is generally comprised of a handle 1601 that is the combination of two halves (1610 and 1635), as well as a tip 1603 that can smoothly penetrate the apex of the heart, and a flexible sheath 1602 which is comprised of concentric catheters that are designed to translate axially and will be described in detail below.

The handle 1601 includes a handle cap 1611 which connects to a female threaded Luer adaptor 1612 in order to provide a sealable exit for a 0.035" diameter guide-wire (not shown). The handle cap 1611 is attached to the handle 1601 with threaded fasteners 1613. The female threaded Luer adaptor 1612 is in threaded contact with the handle cap 1611 through a tapped port, and when fully inserted squeezes against an O-ring (1636 best seen in FIG. 18) which seals against the outer diameter of a guide-wire catheter (1621 best seen in FIG. 18).

Figure 17:
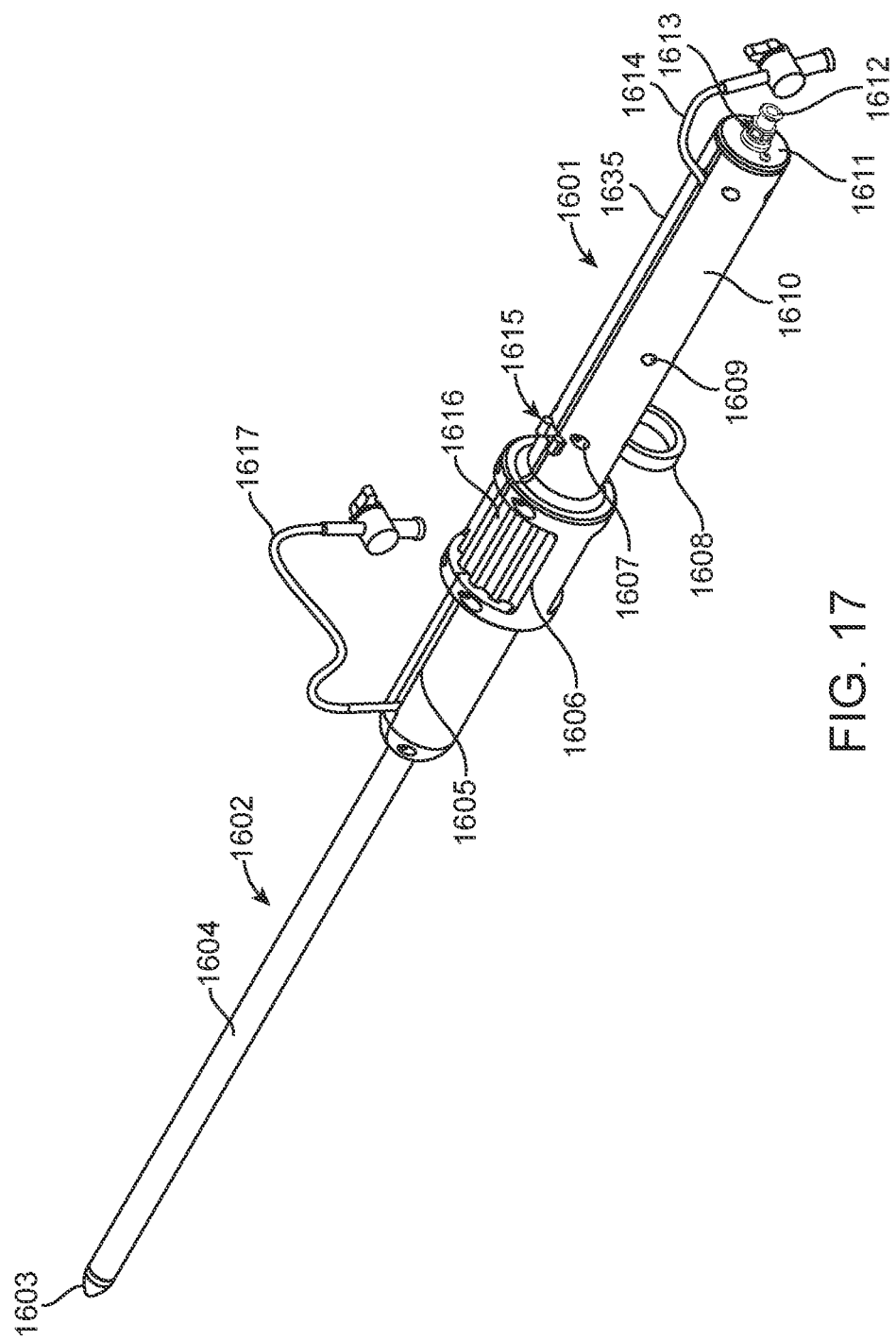
FIG. 17 is a perspective view of the delivery device in FIG. 16.

As can be seen in FIG. 17, the handle 1601 provides location for the control mechanisms used to position and deploy a prosthetic mitral valve. The handle 1601 provides housing for a thumbwheel 1616 that can be accessed through a window 1606 that appears on both the top and bottom of the handle 1601. The thumbwheel 1616 internally mates with a threaded insert (1627 in FIG. 18) that actuates the sheath catheter 1604, and the mechanics of this interaction will be explained in detail below.

Figure 18:
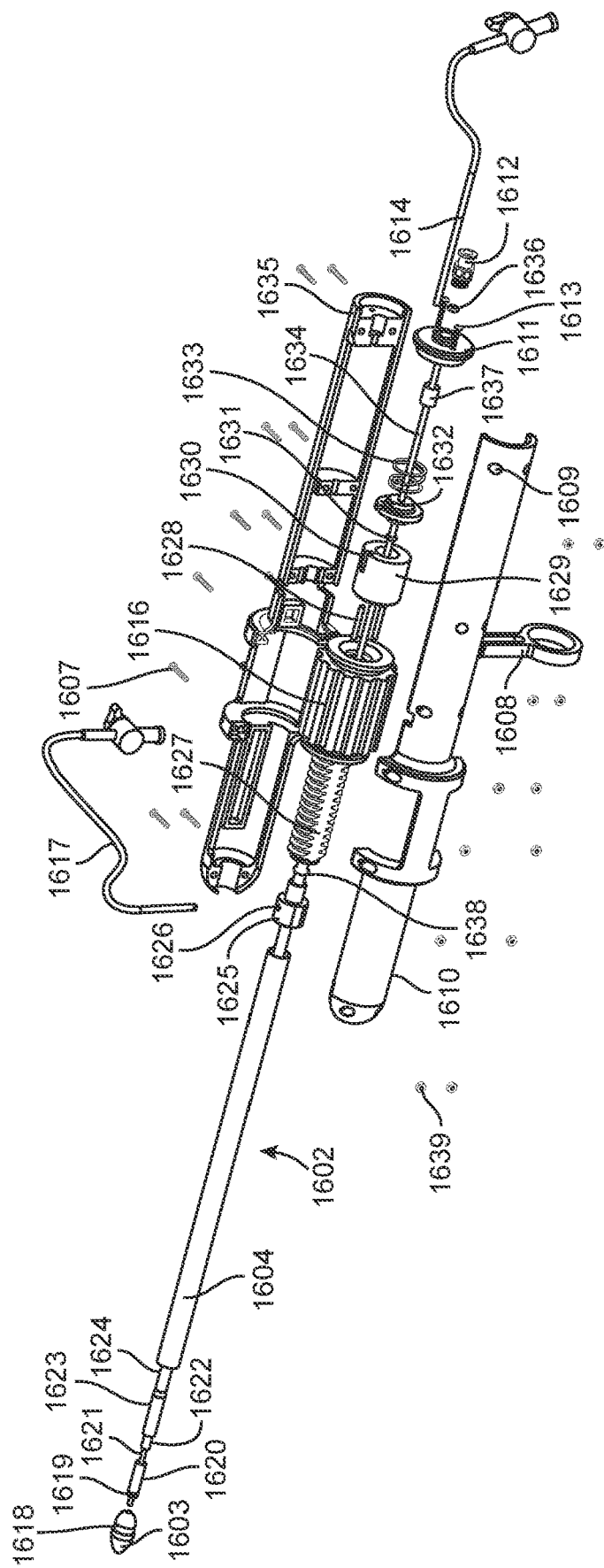
FIG. 18 is an exploded view of the delivery device in FIG. 16.

FIG. 17 also shows a first hemostasis tube 1617 that is inserted internally through a slot 1605, and that mates with a first hemo-port through a hole (1625 and 1626 in FIG. 18 respectively). The first hemostasis tube 1617 allows for fluid purging between internal catheters. The position of the first hemostasis tube 1617 along the slot 1605 provides a visual cue as to the position of the sheath catheter 1604, and relative deployment phase of a prosthetic mitral valve (not shown). The relationship between the connection of the first hemostasis tube 1617 and the sheath catheter 1604 will be described below.

As can also be seen in FIG. 17, a second hemostasis tube 1614 is inserted into the handle 1601 and mated to a second hemo-port (1629 in FIG. 18) in order to allow fluid purging between internal catheters, and details of this insertion will be described below. Finally, a pin lock 1608 provides a security measure against premature release of a prosthetic mitral valve, by acting as a physical barrier to translation between internal mechanisms. Pin lock prongs 1615 rely on spring force to retain the pin lock 1608 in the handle 1601, and a user must first pull out the pin lock 1608 before final deployment of a prosthetic valve.

FIG. 17 also shows how the handle 1601 is fastened together by use of threaded fasteners and nuts (1607 and 1639 of FIG. 18 respectively), and countersunk locator holes 1609 placed throughout the handle length.

Internal mechanisms of the delivery system are illustrated in detail in FIG. 18, and the following descriptions will reveal the interactions between individual components, and the manner in which those components combine in order to create a system that is able to deliver a prosthetic mitral valve preferably transapically.

As seen in FIG. 18, the flexible sheath 1602 is comprised of four concentrically nested catheters. In order from smallest to largest in diameter, the concentrically nested catheters will be described in detail. The innermost catheter is a guide-wire catheter 1621 that runs internally throughout the entire delivery system, beginning at the tip 1603 and terminating in the female threaded Luer adaptor 1612. The guidewire catheter 1621 is composed of a lower durometer, single lumen PEBAX extrusion and is stationary. It provides a channel through which a guide-wire (not shown) can communicate with the delivery system. The next catheter is the hub catheter 1622 which provides support for the hub 1620 and is generally comprised of a higher durometer, single lumen PEEK extrusion. The hub catheter 1622 is in mating connection with both the hub 1622 at the distal end, and a stainless steel support rod 1634 at the proximal end. The stainless steel support rod 1634 is held fixed by virtue of a stopper 1637 that is encased in the handle 1601. The hub catheter 1622 is stationary, and provides support and axial rigidity to the concentrically nested catheters. The next catheter is the bell catheter 1624, which provides housing to the hub 1620 and is generally comprised of a medium durometer, single lumen PEBAX extrusion, including internal steel braiding and lubricious liner, as well as a radiopaque marker band (not shown). The bell catheter 1624 translates axially, and can be advanced and retracted with respect to the hub 1620. The bell catheter 1624 is in mating connection with the second hemo-port 1629 at the proximal end, and hemostasis between the bell catheter 1624 and the stainless steel support rod 1634 can be achieved by purging the second hemostasis tube 1614. The bell catheter 1624 is bumped up to a larger diameter 1623 on the distal end in order to encapsulate the hub 1620. The outermost and final catheter is the sheath catheter 1604 which provides housing for a prosthetic mitral valve (not shown), and which is able to penetrate the apex of the heart (not shown), by supporting and directing a tip 1603 and assisting in the dilation of an incision in the heart wall muscle. The sheath catheter 1604 is generally comprised of a medium durometer, single lumen PEBAX extrusion, including internal steel braiding and lubricious liner, as well as radiopaque marker band (not shown). The sheath catheter 1604 translates axially, and can be advanced and retracted with respect to the hub 1620. The sheath catheter 1604 is in mating connection with the first hemo-port 1625 at the proximal end, and hemostasis between the sheath catheter 1604 and the bell catheter 1624 can be achieved by purging the first hemostasis tube 1617.

As seen in FIG. 18, the proximal end of the sheath catheter 1604 is in mating contact with a first hemo-port 1625. The first hemo-port is in mating contact with a threaded insert 1627, and an O-ring 1638, which is entrapped between the first hemo-port 1625 and the threaded insert 1627 in order to compress against the bell catheter 1624, creating a hemostatic seal. As the thumbwheel 1616 is rotated, the screw insert 1627 will translate, and the sheath catheter 1624 can be retracted or advanced by virtue of attachment. In order to provide adequate stiffness to dilate heart wall tissue, the distal edge of the sheath catheter 1604 will abut against a shoulder 1618 located on the tip 1603. This communication allows the tip 1603 to remain secure and aligned with the sheath catheter 1604 during delivery, and creates piercing stiffness.

FIG. 18 also details the mechanism through which the bell catheter 1624 can be retracted or advanced with respect to the hub 1620. The thumbwheel 1616 can be rotated to such an extent that the screw insert 1627 will be brought into contact with two pins 1628 that are press fit into the second hemo-port 1629. As the bell catheter 1624 is in mating contact with the second hemo-port 1629, further rotation of the thumbwheel 1616 will cause the second hemo-port 1629 to translate and press against a spring 1633 by virtue of connection to a second hemo-port cap 1632. This advancement will cause the bumped larger diameter section 1623 of the bell catheter 1624 to be retracted from the hub 1620. As the thumbwheel 1616 is rotated in the opposite direction, restoring force produced by the spring 1633 will cause the second hemo-port 1629 to be pushed in the opposite direction, drawing the bumped larger diameter section 1623 of the bell catheter 1624 back over the hub 1620, an action that is necessary during the initial loading of a valve prosthesis.

FIG. 18 further details the manner in which hemostasis is achieved between the stainless steel support rod 1634 and the bell catheter 1624. An O-ring 1631 is compressed between the second hemo-port 1629 and the second hemo-port cap 1632, creating a seal against the stainless steel support rod 1634. Hemostasis between the bell catheter 1624 and the stainless steel support rod 1634 can be achieved by purging the second hemostasis tube 1614, which is in communication with the void to be purged through a slot and hole 1630.

Figure 19A:
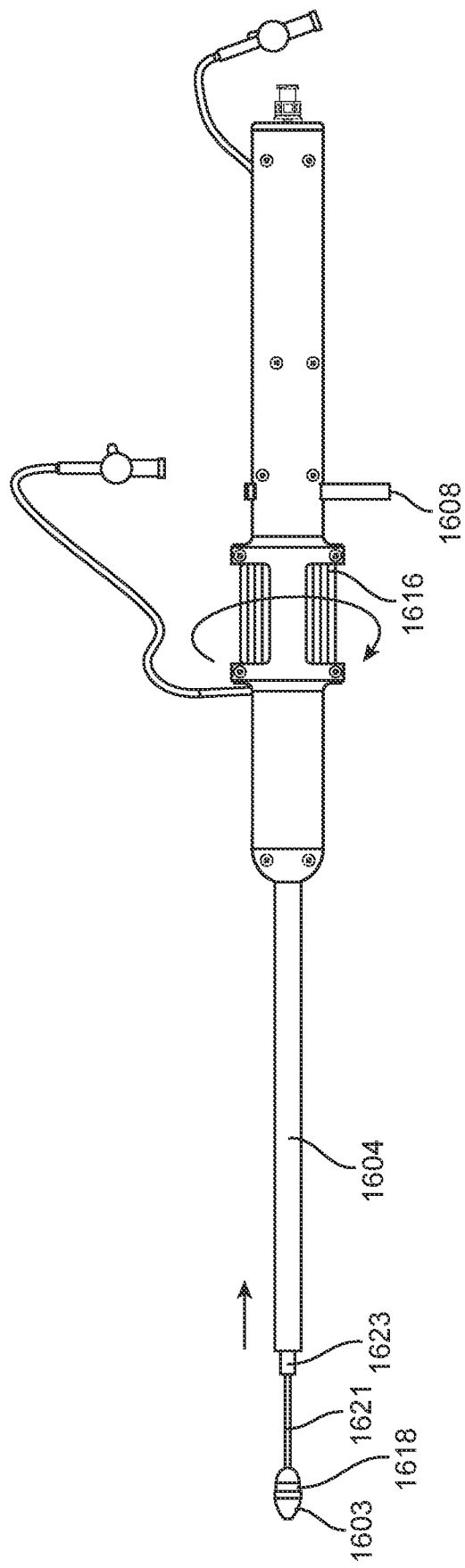
FIGS. 19A-19B are side views of the delivery device in FIG. 16 during various stages of operation.
Figure 19B:
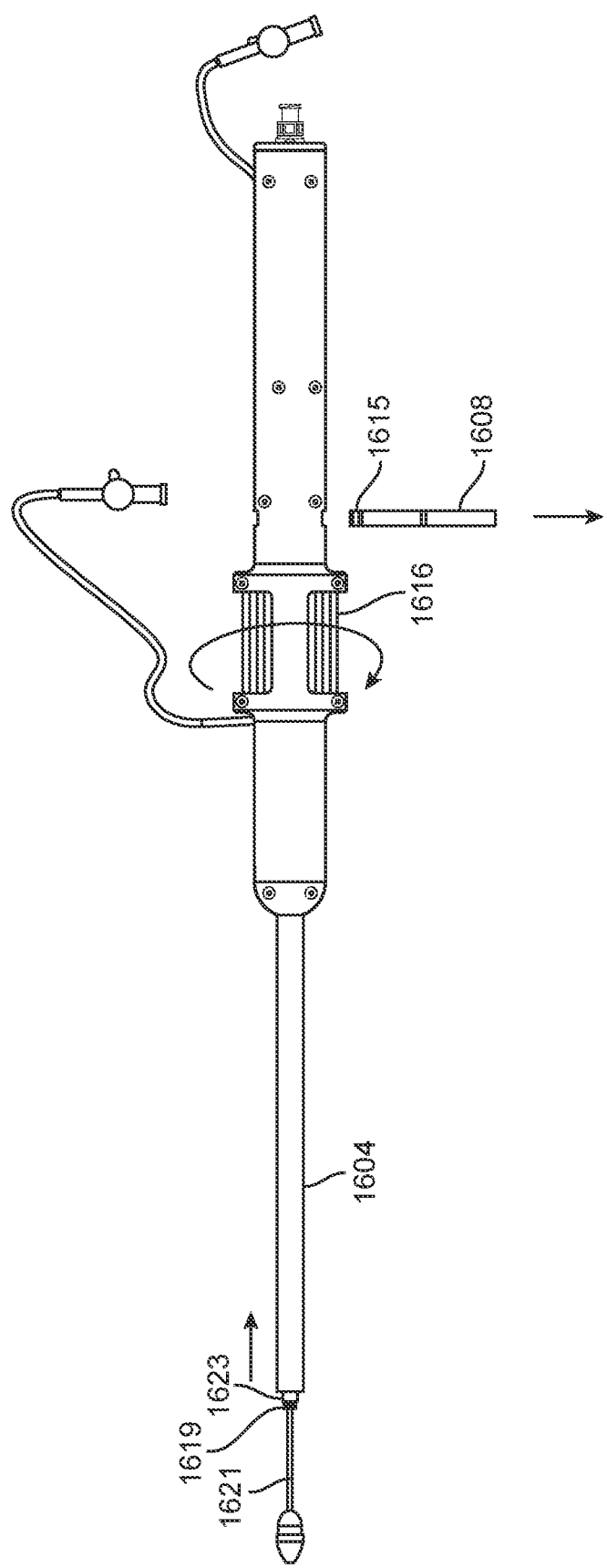

The deployment process and actions necessary to activate the mechanisms responsible for deployment are detailed in FIGS. 19A-19B. When performed in the reverse order, these actions also necessitate the first loading of a valve (not shown) prior to surgery.

As seen in FIG. 19A, manipulation of the thumbwheel 1616 will provide translational control of the sheath catheter 1604. In order to effect the deployment of a heart valve (not shown), the user must withdraw the sheath catheter 1604 from contact with the shoulder 1618 of the tip 1603 until it passes the larger diameter section 1623 of the bell catheter 1624. A heart valve (not shown) will reside concentrically above the guide-wire catheter 1621 in the position indicated by the leader for 1621 in FIG. 19A, similarly as to the example illustrated in FIG. 13. The sheath catheter 1604 can be withdrawn until the screw insert 1627 comes into contact with the pin lock 1608. The pin lock 1608 must then be removed before further travel of the screw insert 1627 can be achieved.

As seen in FIG. 19B, the pin lock 1608 is removed from the handle 1601 in order to allow further translation of the sheath catheter 1604. When the sheath catheter 1604 is fully retracted, the larger diameter section 1623 of the bell catheter 1624 is also fully retracted, which completely frees the heart valve (not shown) from the delivery system. Three hub slots 1619, spaced circumferentially at about 120 degrees from each other provide the anchoring mechanism and physical link between delivery system and heart valve. Once the larger diameter section 1623 of the bell catheter 1624 has been withdrawn, the hub slots 1619 become uncovered which allows the heart valve anchor (not shown) to fully expand.

Figure 16:
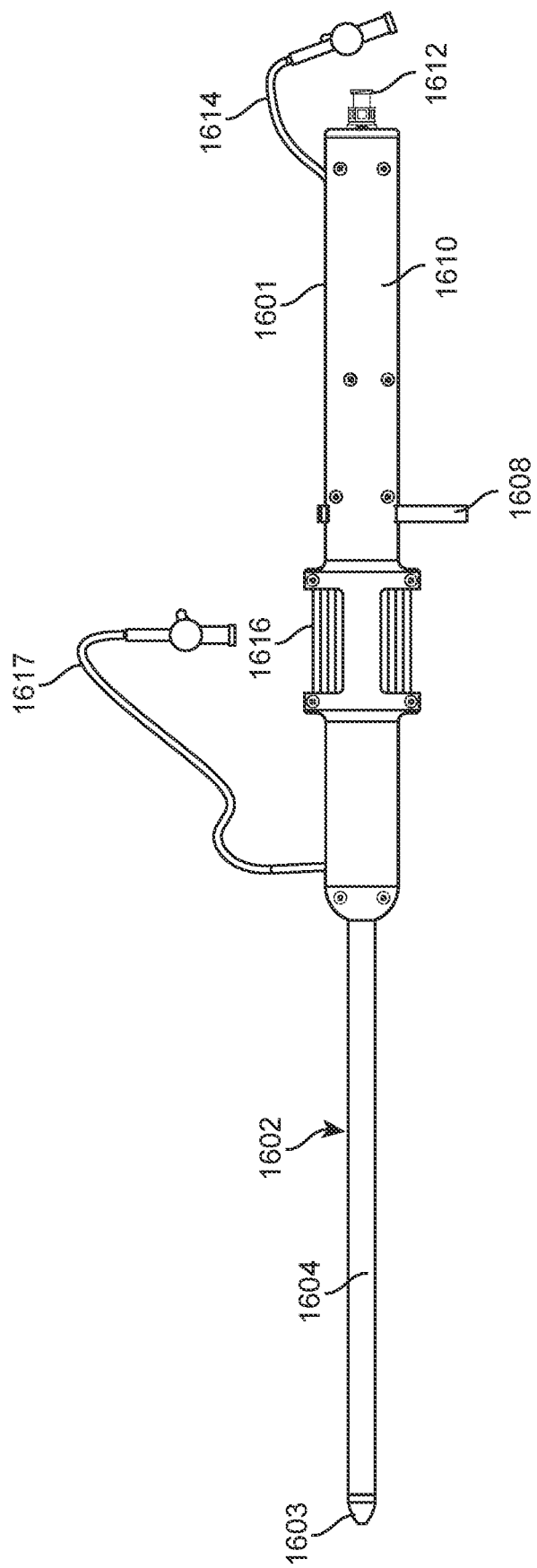
FIG. 16 is a side view of another example of a delivery device for implantation of a prosthetic valve.
Figure 20:
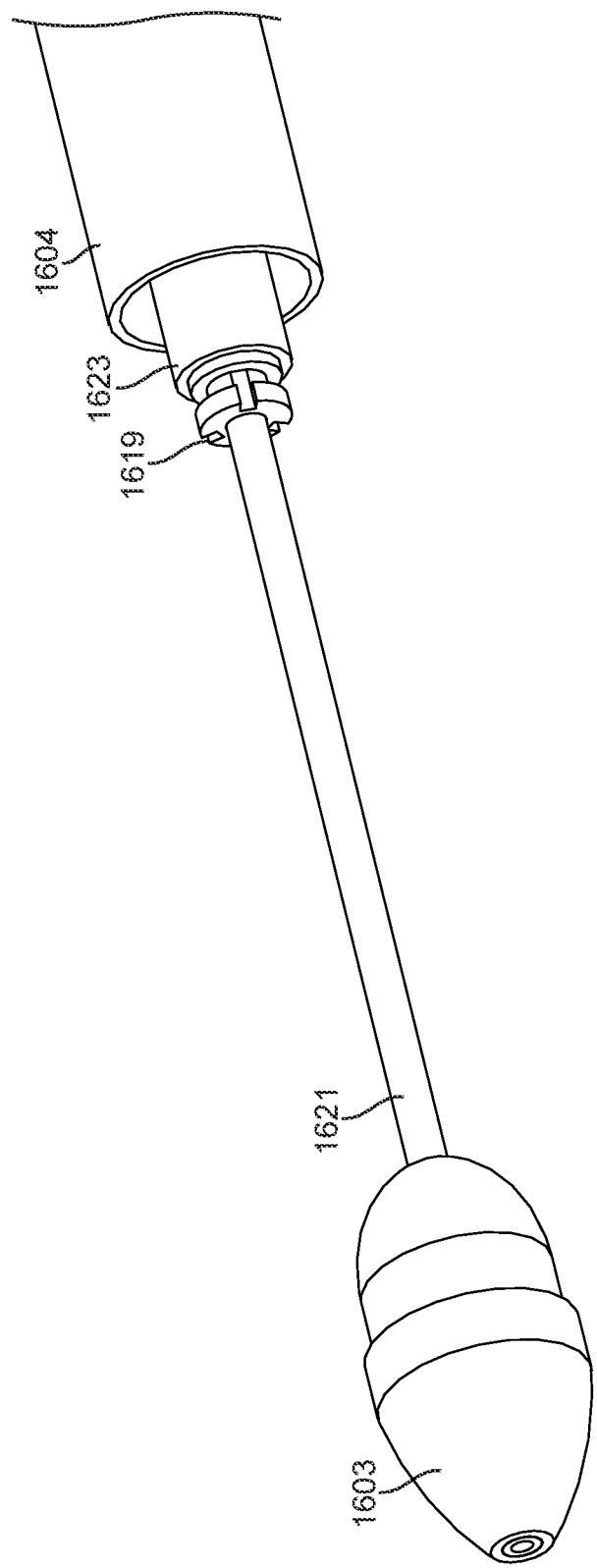
FIG. 20 illustrates a distal portion of the delivery device in FIG. 16 that is adapted to engage a portion of a prosthetic valve.

FIG. 20 illustrates a distal portion of the delivery device in FIG. 16. Three hub slots 1619 are slidably disposed distally relative to the large diameter tip 1623 of bell catheter 1624. These slots allow engagement with a prosthetic valve. The valve may be releasably held by the slots by disposing the commissure tabs or tabs 812 of the prosthetic valve into slots 1619 and then retracting the slots 1619 under tip 1623 of bell catheter 1624. The prosthetic valve may be released from the delivery catheter by advancing the slots distally relative to the bell catheter so that the loading anchors or tabs 812 may self-expand out of and away from slots 1619 when the constraint of tip 1623 on bell catheter 1624 has been removed.

FIG. 21 illustrates a prosthetic mitral valve 800 (as discussed above with reference to FIG. 8A) with the anchor tabs 812 disposed in the hub slots (not visible), and bell catheter 1623 advanced thereover. Thus, even though most of the prosthetic valve 800 has self-expanded into its expanded configuration, the valve commissures remain in a collapsed configuration with the tabs 812 captured in slots 1619. Once the constraint provided by bell catheter 1623 has been removed from the slots 1619, the tabs 812 may self-expand out of slots 1619, the commissures will open up to their unbiased position. The prosthetic valve is then disconnected and free from the delivery device.

Transapical Delivery Methods

Figure 22A:
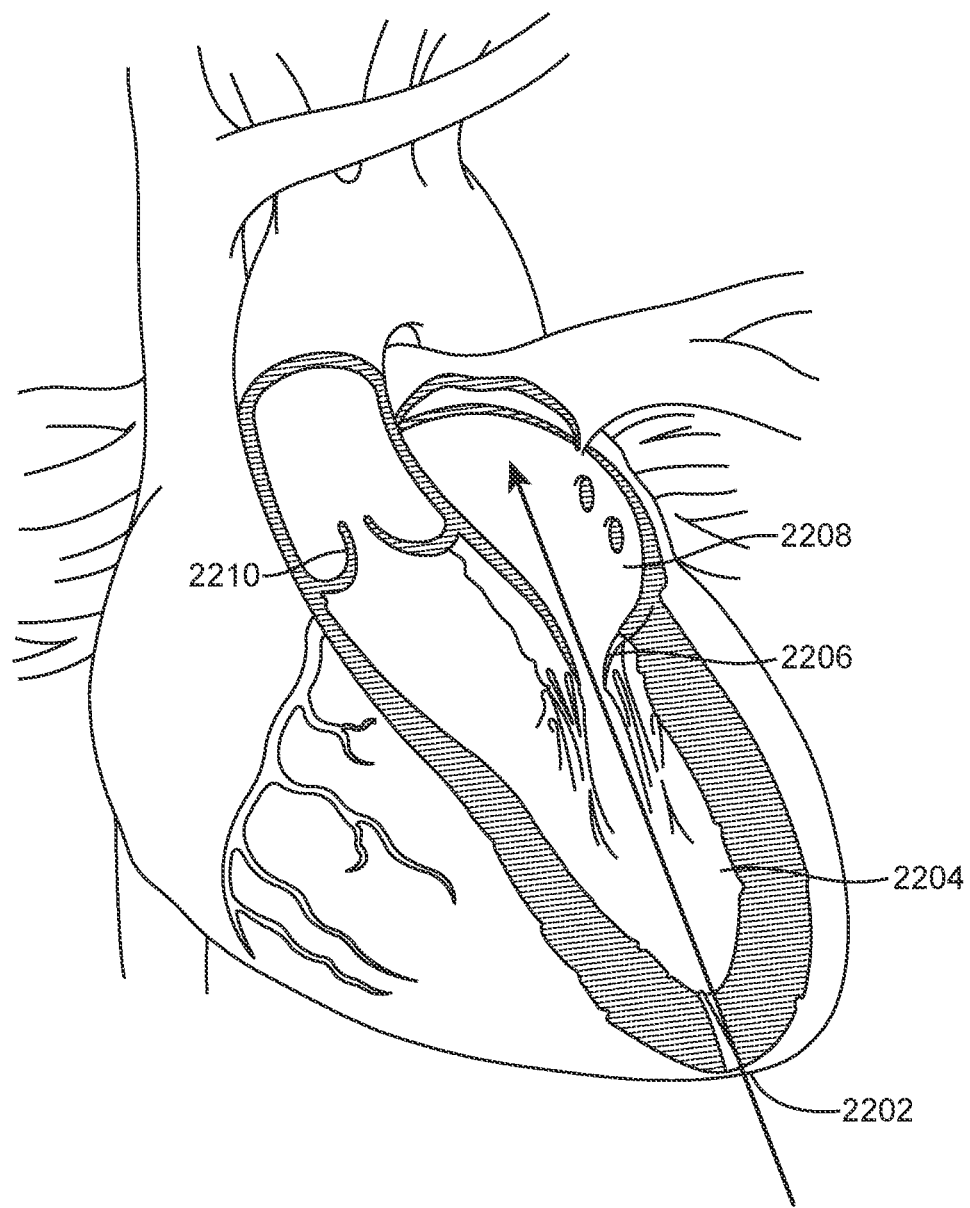
FIGS. 22A-22G illustrate an example of a method of transapically delivering a prosthetic mitral valve.

FIGS. 22A-22G illustrate an example of a method of transapically delivering a prosthetic mitral valve. This example may use any of the prosthetic valves described herein, and may use any of the delivery devices described herein. FIG. 22A illustrates the general transapical pathway that is taken with entry into the heart at the apex 2202, through the left ventricle 2204, across the mitral valve 2206 and into the left atrium 2208. The aortic valve 2210 remains unaffected. Transapical delivery methods have been described in the patent and scientific literature, such as in International PCT Publication No. WO2009/134701, the entire contents of which are incorporated herein by reference.

Figure 22B:
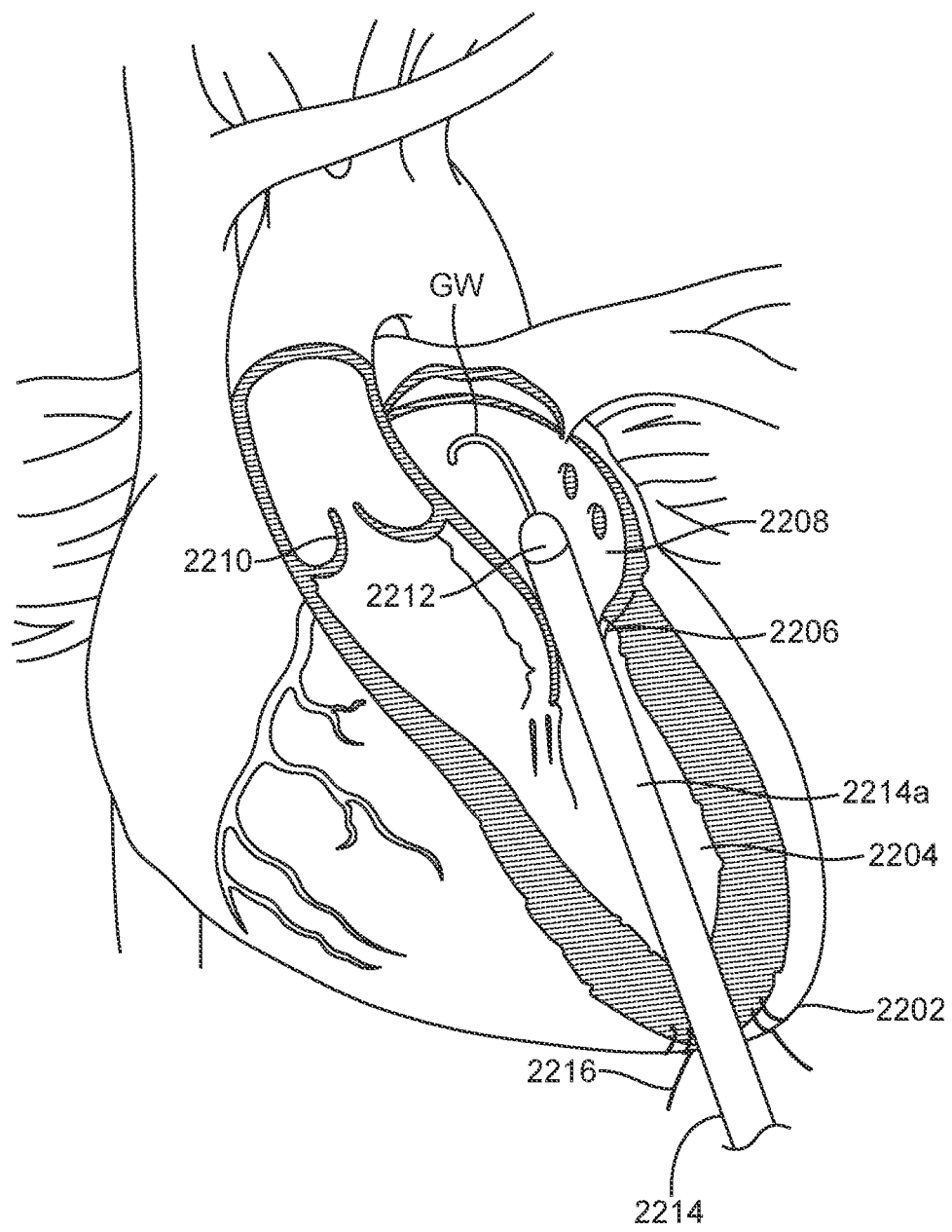

In FIG. 22B a delivery device 2214 is introduced through an incision in the apex 2202 and over a guidewire GW through the ventricle 2204, past the mitral valve 2206 with a distal portion of the delivery device 2214 disposed in the atrium 2208. The delivery device has a rounded tip 2212 that is configured to pass through and dilate the incision, and can be advanced through the heart without causing unwanted trauma to the mitral valve 2206 or adjacent tissue. Suture 2216 may be stitched around the delivery device 2214 at the apex 2202 using a purse string stitch or other patterns known in the art in order to prevent excessive bleeding and to help hold the delivery device in position.

Figure 22C:
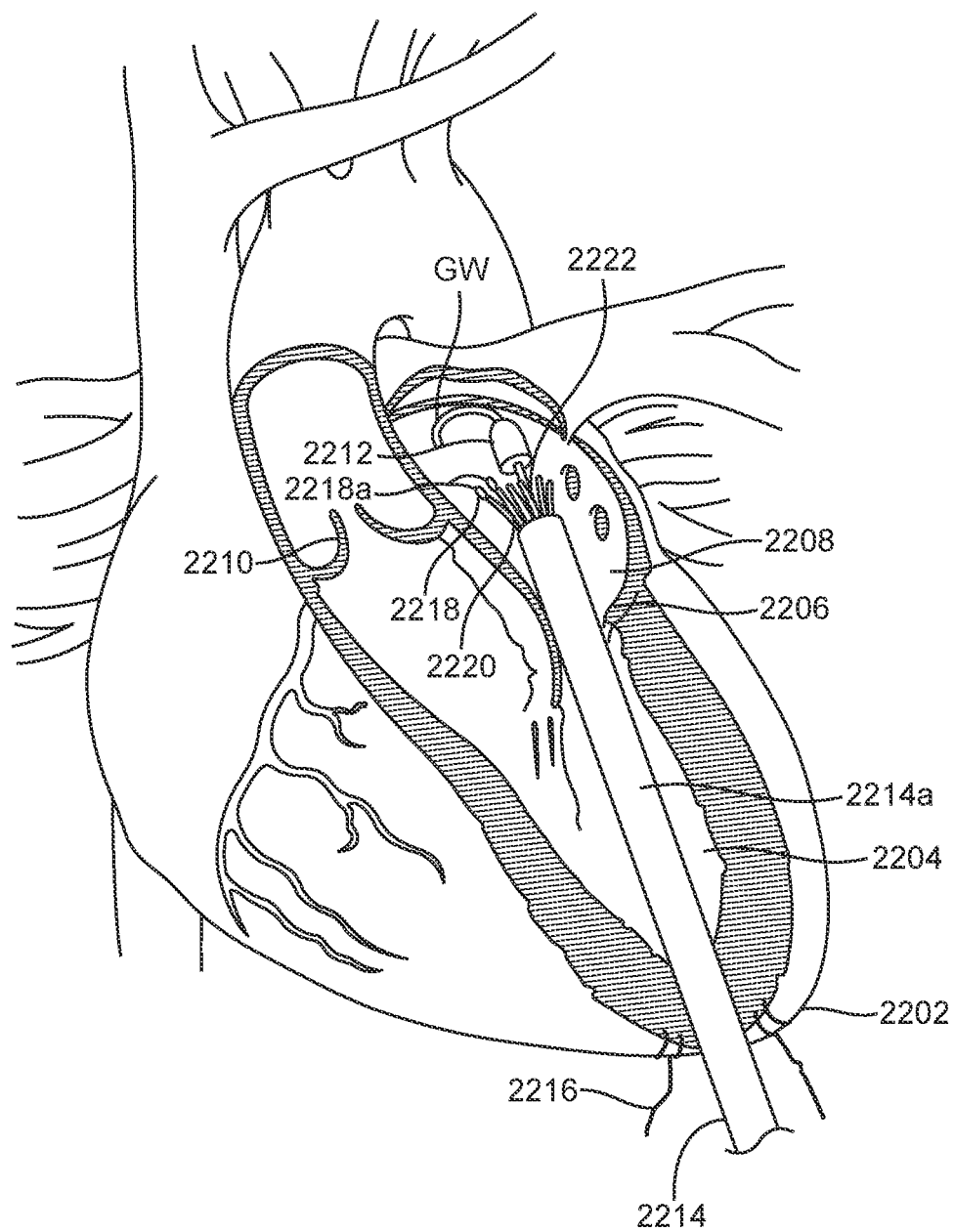

In FIG. 22C, the outer sheath 2214*a* of the delivery device 2214 is retracted proximally relative to the prosthetic mitral valve 2220 (or the prosthetic mitral valve is advanced distally relative to the outer sheath 2214*a*) to expose the alignment element 2218 and a portion of the atrial skirt region 2222 on the prosthetic mitral valve 2220 which allows the atrial skirt region 2222 to begin to partially radially expand outward and flare open. Alignment element 2218 may include a pair of radiopaque markers 2218*a* which facilitate visualization under fluoroscopy. The physician can then align the alignment element so that the radiopaque markers 2218*a* are disposed on either side of the anterior mitral valve leaflet. Delivery device 2214 may be rotated in order to help align the alignment element. The alignment element is preferably situated adjacent the aortic root and between the fibrous trigones of the native anterior leaflet.

Figure 22D:
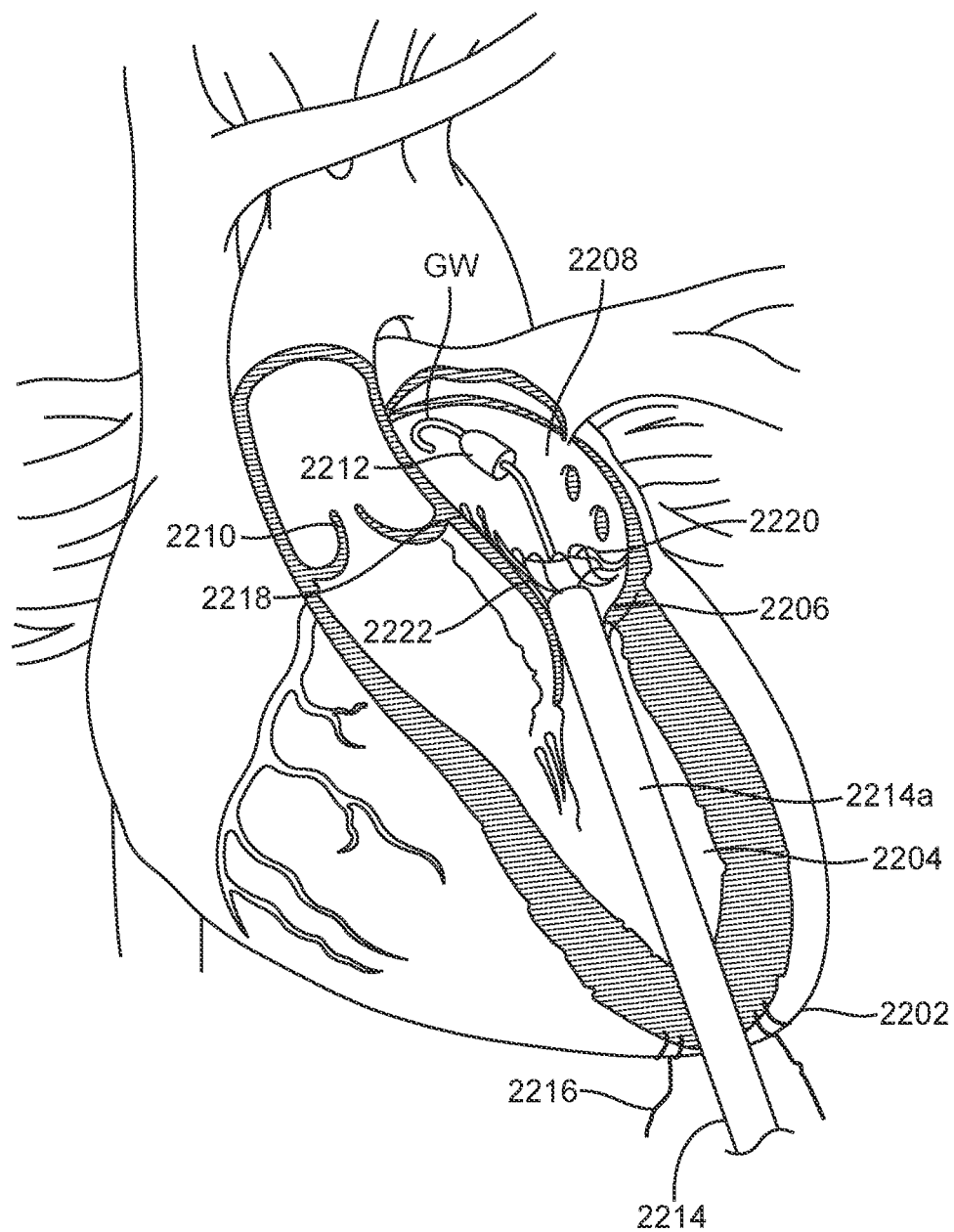

In FIG. 22D once alignment has been obtained, the sheath 2214*a* is further retracted proximally, allowing radial expansion of the atrial skirt 2222 which flares outward to form a flange. Proximal retraction of the delivery device 2214 and prosthetic valve 2220 seat the atrial skirt 2222 against an atrial surface adjacent the mitral valve 2206 thereby anchoring the prosthetic valve in a first position.

Figure 22E:
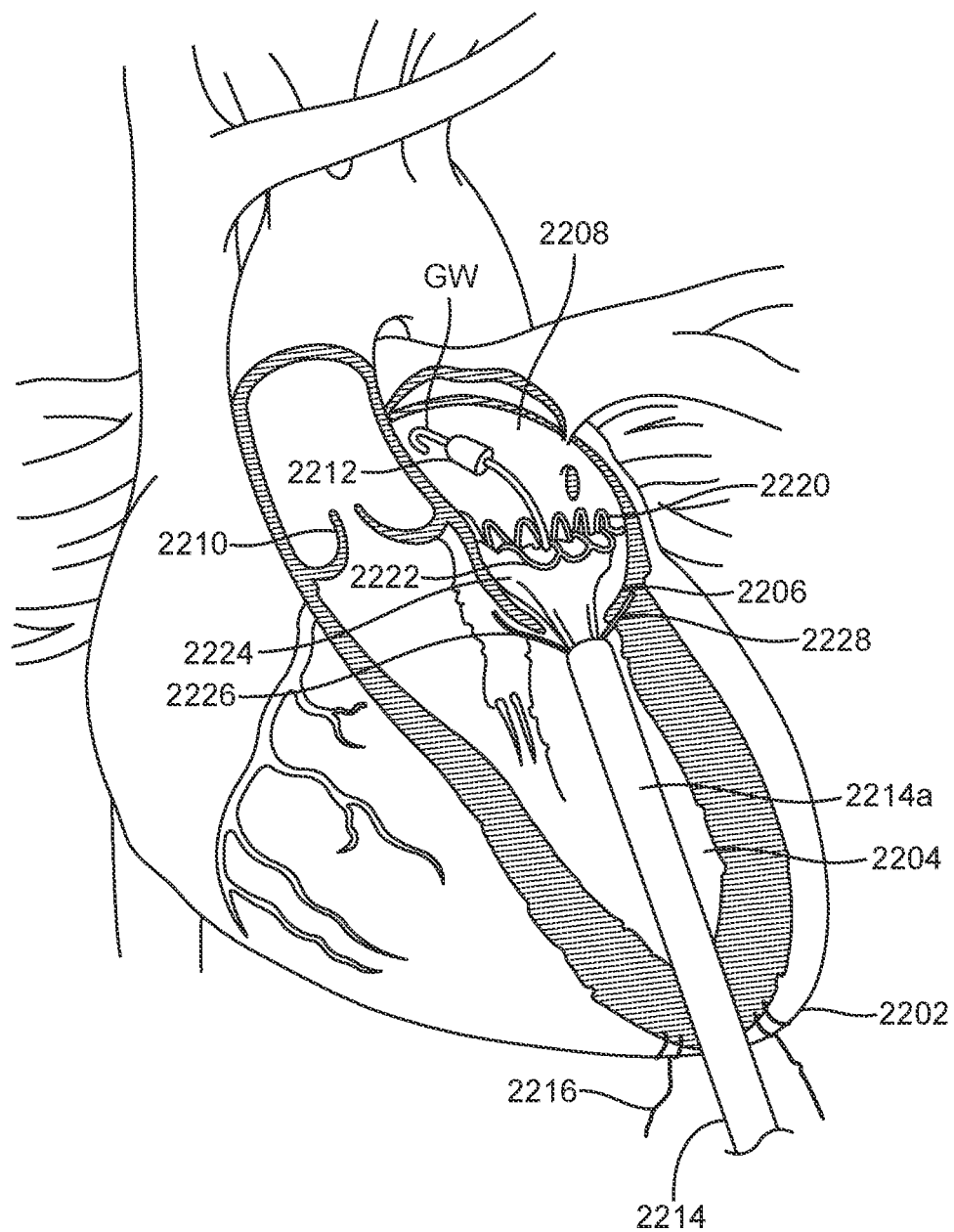

FIG. 22E shows that further proximal retraction of sheath 2214*a* exposes and axially removes additional constraint from the prosthetic valve 2220, thereby allowing more of the valve to self-expand. The annular region 2224 expands into engagement with the mitral valve annulus and the ventricular trigonal tabs 2226 and the posterior tab 2228 radially expand. Portions of the ventricular skirt serve as deployment control regions and prevent the entire ventricular skirt from expanding because they are still constrained. The tabs are captured between the anterior and posterior mitral valve leaflets and the ventricular wall. The posterior ventricular anchoring tab 2228 is preferably aligned in the middle of the posterior mitral valve leaflet where there is an absence of chordae attachments, and is passed over the posterior leaflet to seat between the posterior leaflet and the ventricular wall. The two ventricular trigonal anchoring tabs 2226 are positioned on either side of the anterior leaflet with their heads positioned at the fibrous trigones. Slight rotation and realignment of the prosthesis can occur at this time. As the prosthesis expands, the anterior trigonal tabs anchor against the fibrous trigones, capturing the native anterior leaflet and chordae between the tabs and the anterior surface of the prosthetic valve, and the posterior ventricular tab anchors between the ventricular wall and the posterior leaflet, capturing the posterior leaflet between the posterior anchoring tab and the posterior surface of the prosthetic valve assembly.

Figure 22F:
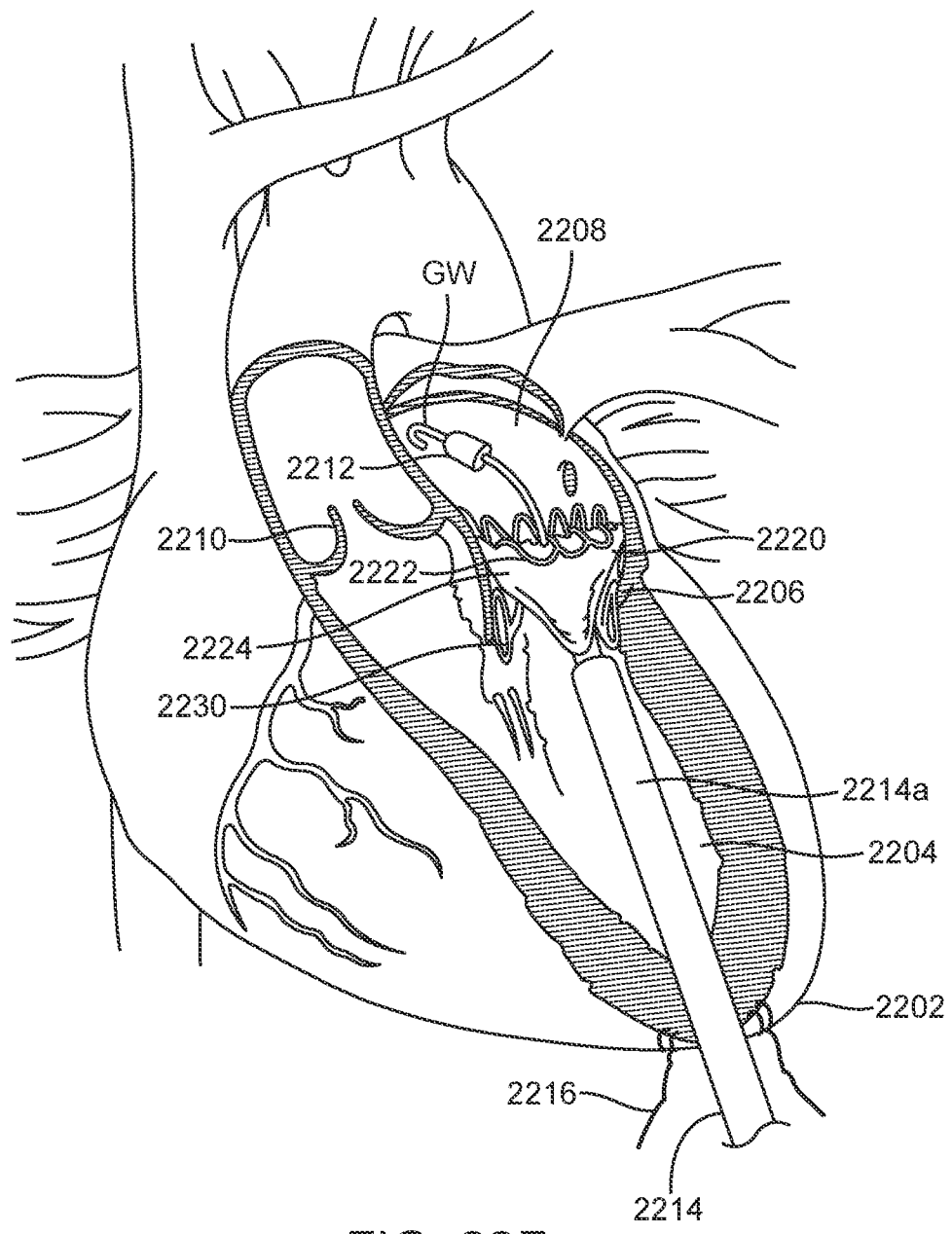
Figure 22G:
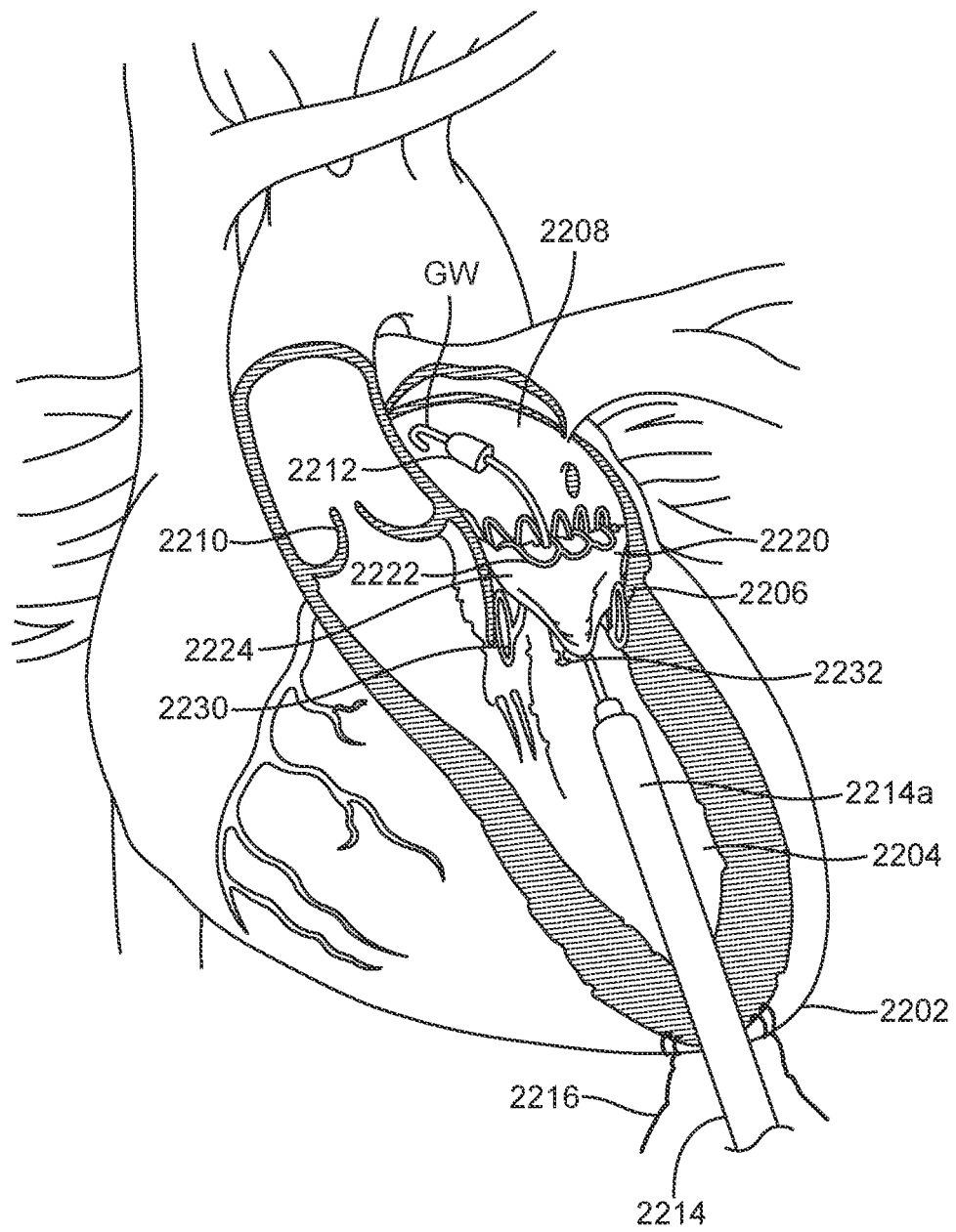

FIG. 22F shows that further retraction of sheath 2214*a* releases the ventricular trigonal tabs and the posterior tab and the deployment control regions of the ventricular skirt 2230 are also released and allowed to radially expand outward against the native mitral valve leaflets. This creates a sealing funnel within the native leaflets and helps direct blood flow through the prosthetic mitral valve. With the commissures of the prosthesis still captured within the delivery system, very minor adjustments may still be made to ensure accurate positioning, anchoring and sealing. The prosthetic valve is now anchored in four positions. The anchor tabs 2232 are then released from the delivery device by retraction of an inner shaft, allowing the tabs to self-expand out of slots on the delivery catheter as previously discussed above and shown in FIG. 22G. The prosthetic valve is now implanted in the patient's heart and takes over the native mitral valve. The delivery device 2214 may then be removed from the heart by proximally retracting it and removing it from the apex incision. The suture 2216 may then be tied off, sealing the puncture site.

Transseptal Delivery Methods

Figure 23A:
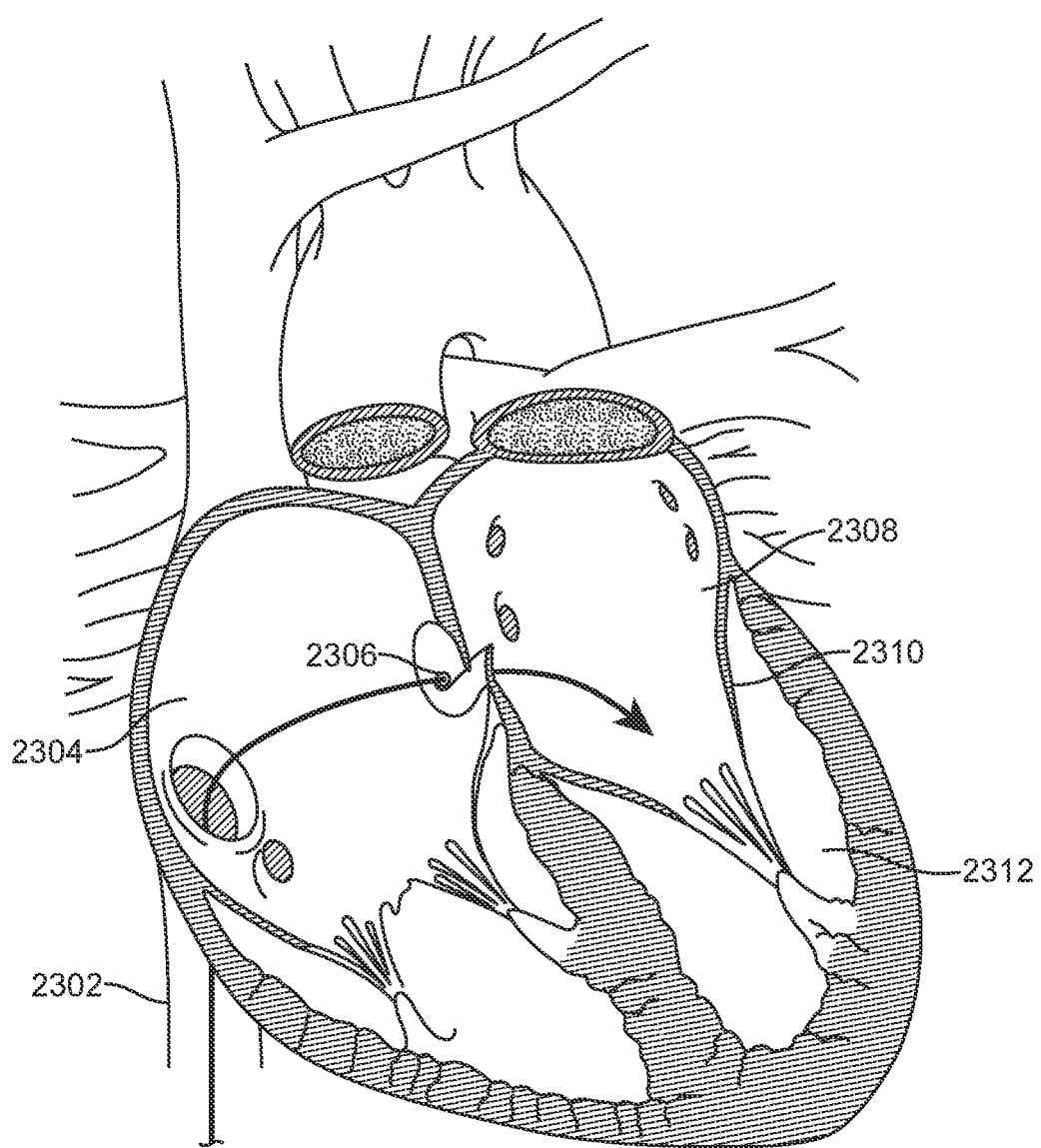
FIGS. 23A-23G illustrate an example of a method of transseptally delivering a prosthetic mitral valve.

FIGS. 23A-23G illustrate an example of a method of transseptally delivering a prosthetic mitral valve. This example may use any of the prosthetic valves described herein, and may use any of the delivery devices described herein if modified appropriately. One of skill in the art will appreciate that relative motion of the various shafts in the delivery system examples disclosed above may need to be reversed in order to accommodate a transseptal approach. FIG. 23A illustrates the general transseptal pathway that is taken with the delivery device passing up the vena cava 2302 into the right atrium 2304. A transseptal puncture 2306 is created through the atrial septum, often through the foramen ovale, so that the device may be passed into the left atrium 2308, above the mitral valve 2310 and adjacent the left ventricle 2312. Transseptal techniques have been published in the patent and scientific literature, such as in U.S. Patent Publication No. 2004/0181238 to Zarbatany et al., the entire contents of which are incorporated herein by reference.

Figure 23B:
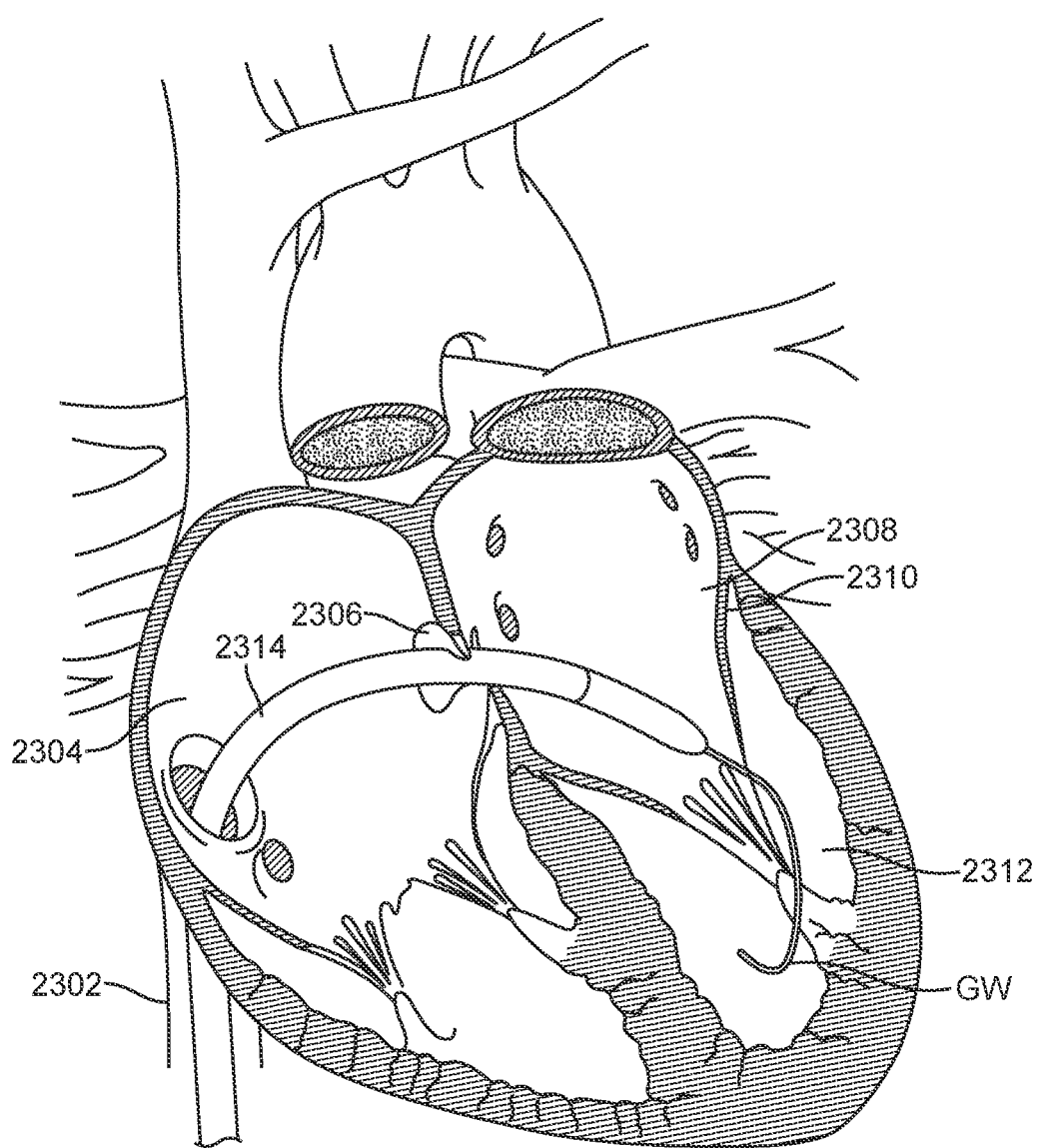

In FIG. 23B a delivery device 2314 is passed over a guidewire GW through the vena cava 2302 into the right atrium 2306. The delivery device 2314 is then transseptally passed through the atrial wall into the left atrium 2308 adjacent the mitral valve 2310. The guide-wire GW may be disposed across the mitral valve 2310 in the left ventricle 2312. The distal tip of the delivery device typically includes a nose cone or other atraumatic tip to prevent damaging the mitral valve or adjacent tissue.

Figure 23C:
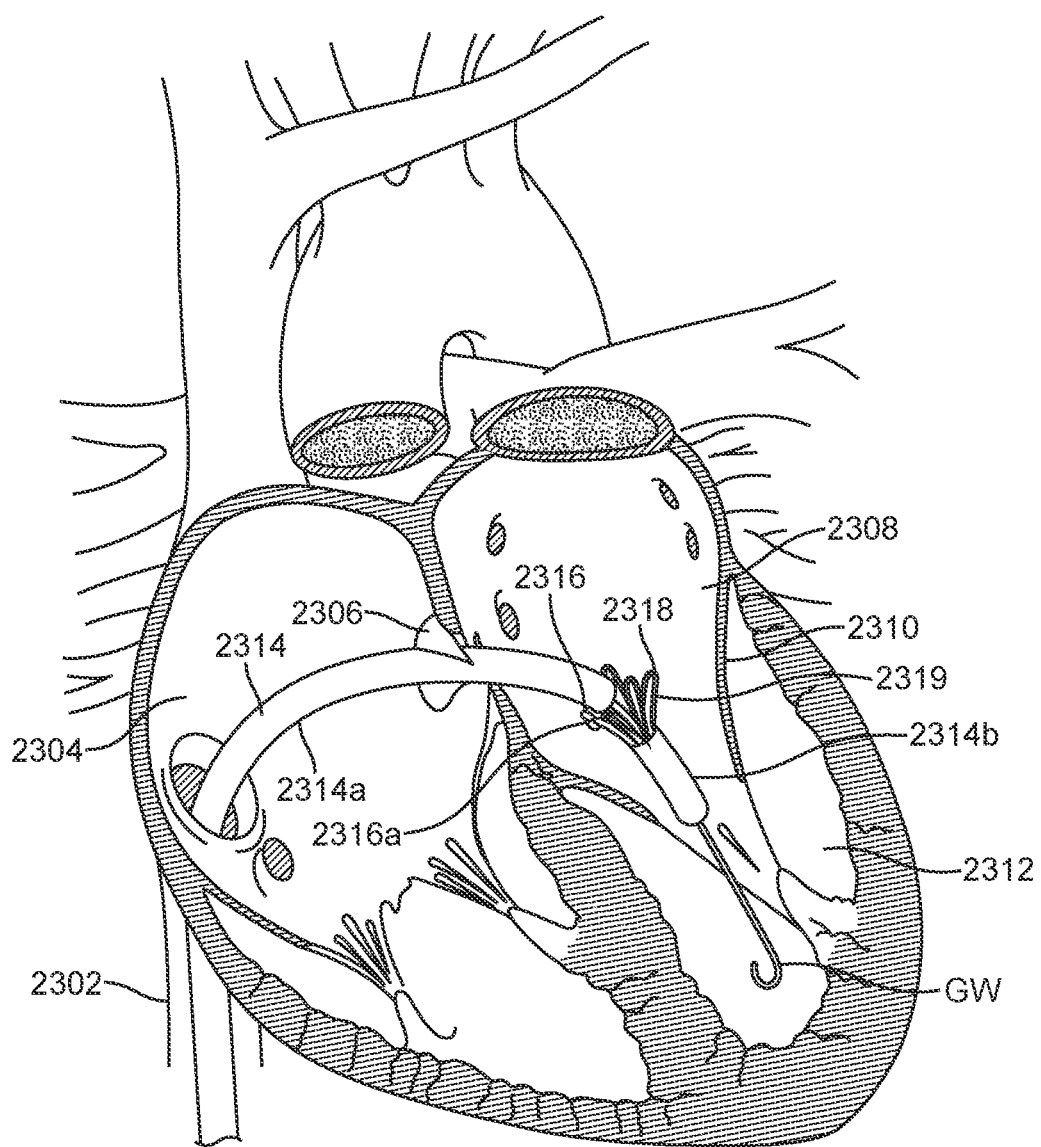

In FIG. 23C, the outer sheath 2214a of the delivery device 2214 is retracted proximally relative to the prosthetic mitral valve 2319. Alternatively, a distal portion 2314b of the delivery device 2214 may be advanced distally relative to the prosthetic valve 2319 to expose the alignment element 2316 and a portion of the atrial skirt region 2318 on the prosthetic mitral valve 2319 which allows the atrial skirt region 2318 to begin to partially radially expand outward and flare open. Alignment element 2316 may include a pair of radiopaque markers 2316a which facilitate visualization under fluoroscopy. The physician can then align the alignment element so that the radiopaque markers 2316a are disposed on either side of the anterior mitral valve leaflet. The alignment element is preferably situated adjacent the aortic root and between the fibrous trigones of the native anterior leaflet. Delivery device 2214 may be rotated in order to help align the alignment element.

Figure 23D:
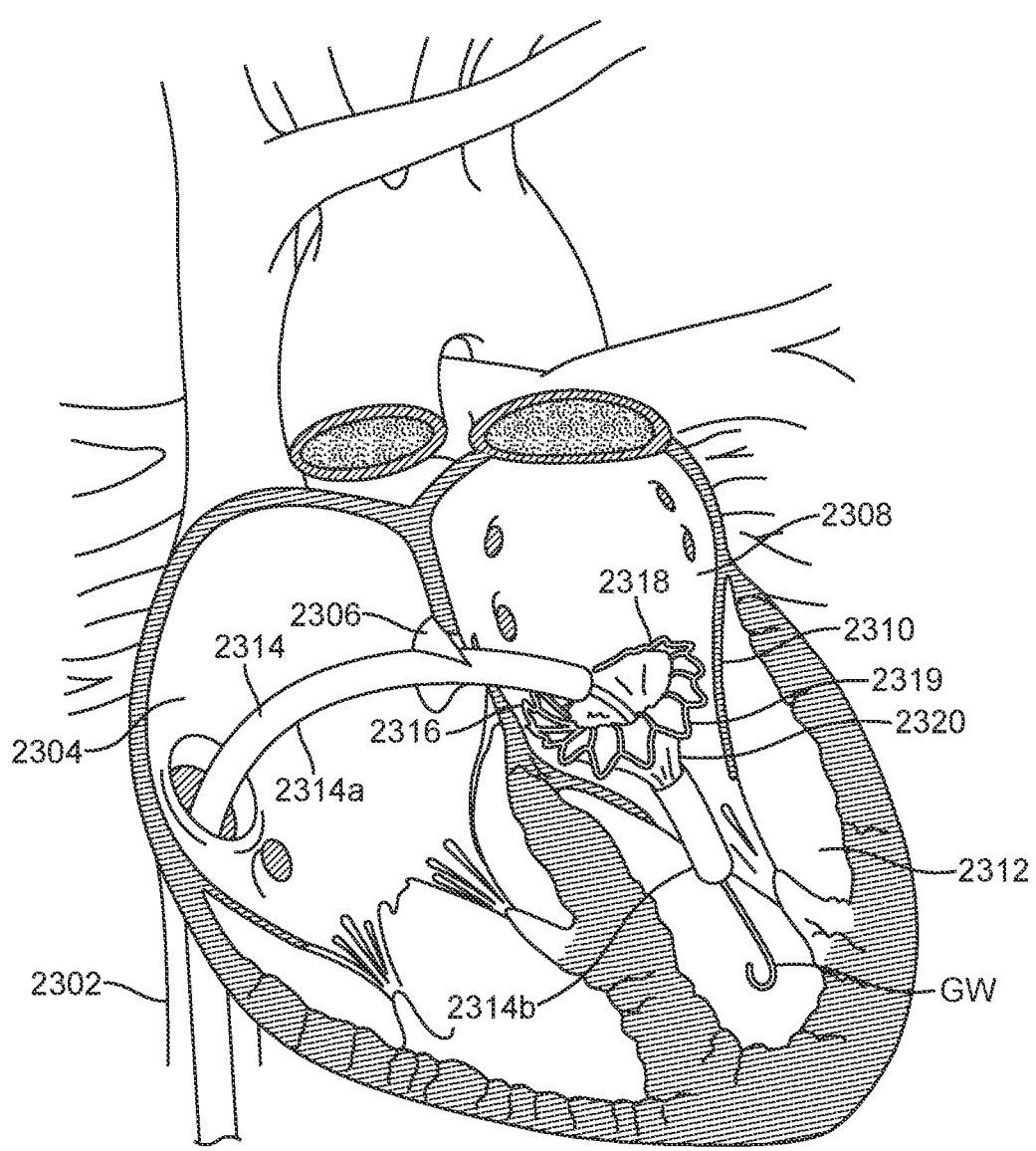

In FIG. 23D once alignment has been obtained, the distal portion 2314b is further advanced distally allowing radial expansion of the atrial skirt 2318 which flares outward to form a flange. Distally advancing the delivery device 2214 and prosthetic valve 2319 seats the atrial skirt 2318 against an atrial surface adjacent the mitral valve 2310 thereby anchoring the prosthetic valve in a first position.

Figure 23E:
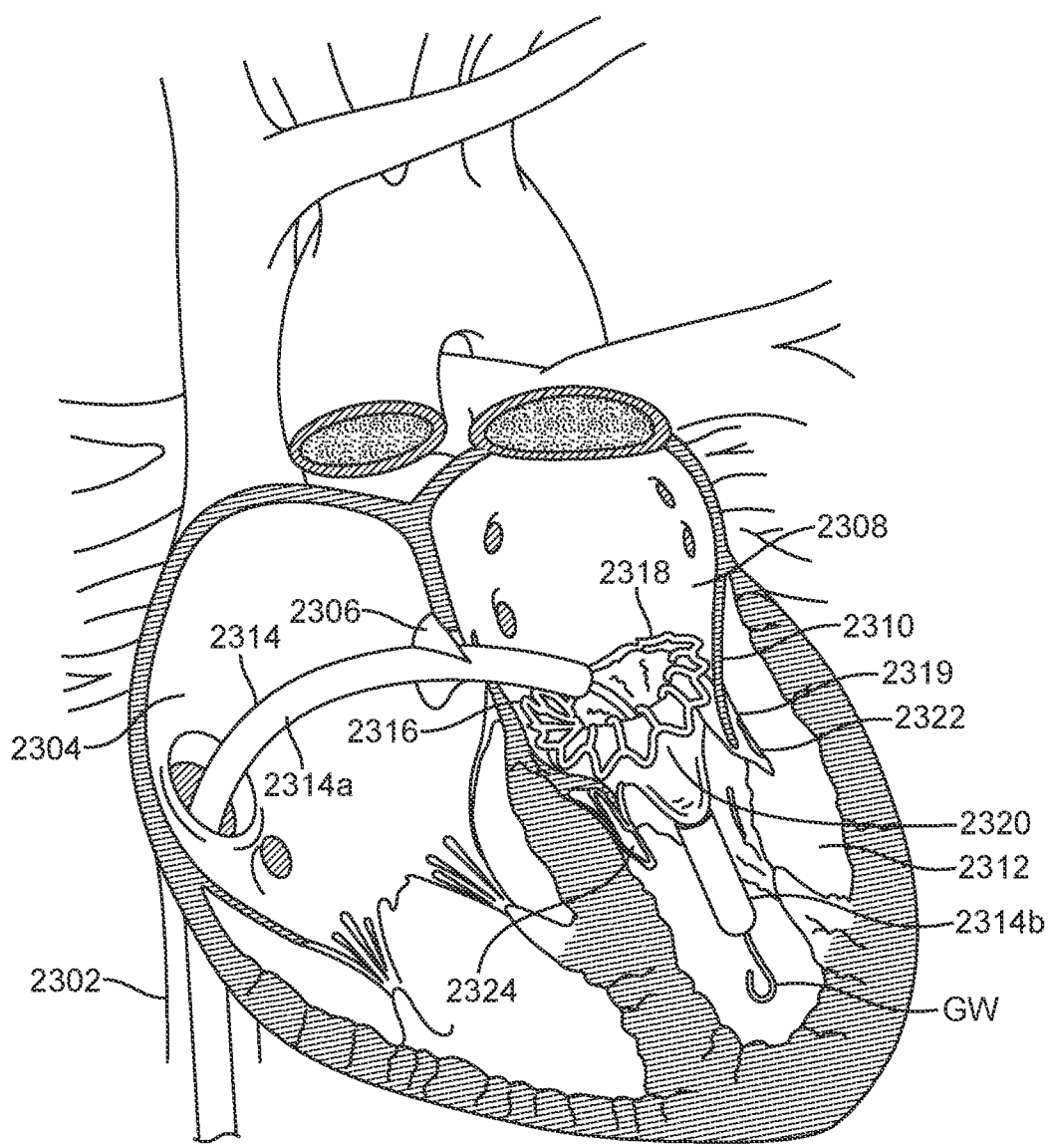

FIG. 23E shows that further distal advancement of distal portion 2314b exposes and axially removes additional constraint from the prosthetic valve 2319, thereby allowing more of the valve to self-expand. The annular region 2320 expands into engagement with the mitral valve annulus and the ventricular trigonal tabs 2324 and the posterior tab 2322 radially expand. Portions of the ventricular skirt serve as deployment control regions since they remain constrained and thus the entire ventricular skirt cannot expand. The tabs are captured between the anterior and posterior mitral valve leaflets and the ventricular wall. The posterior ventricular anchoring tab 2322 is preferably aligned in the middle of the posterior mitral valve leaflet where there is an absence of chordae attachments, and is passed over the posterior leaflet to seat between the posterior leaflet and the ventricular wall. The two ventricular trigonal anchoring tabs 2324 are positioned on either side of the anterior leaflet with their heads positioned at the fibrous trigones. Slight rotation and realignment of the prosthesis can occur at this time. As the prosthesis expands, the anterior trigonal tabs anchor against the fibrous trigones, capturing the native anterior leaflet and chordae between the tabs and the anterior surface of the prosthetic valve, and the posterior ventricular tab anchors between the ventricular wall and the posterior leaflet, capturing the posterior leaflet between the posterior anchoring tab and the posterior surface of the prosthetic valve assembly.

Figure 23F:
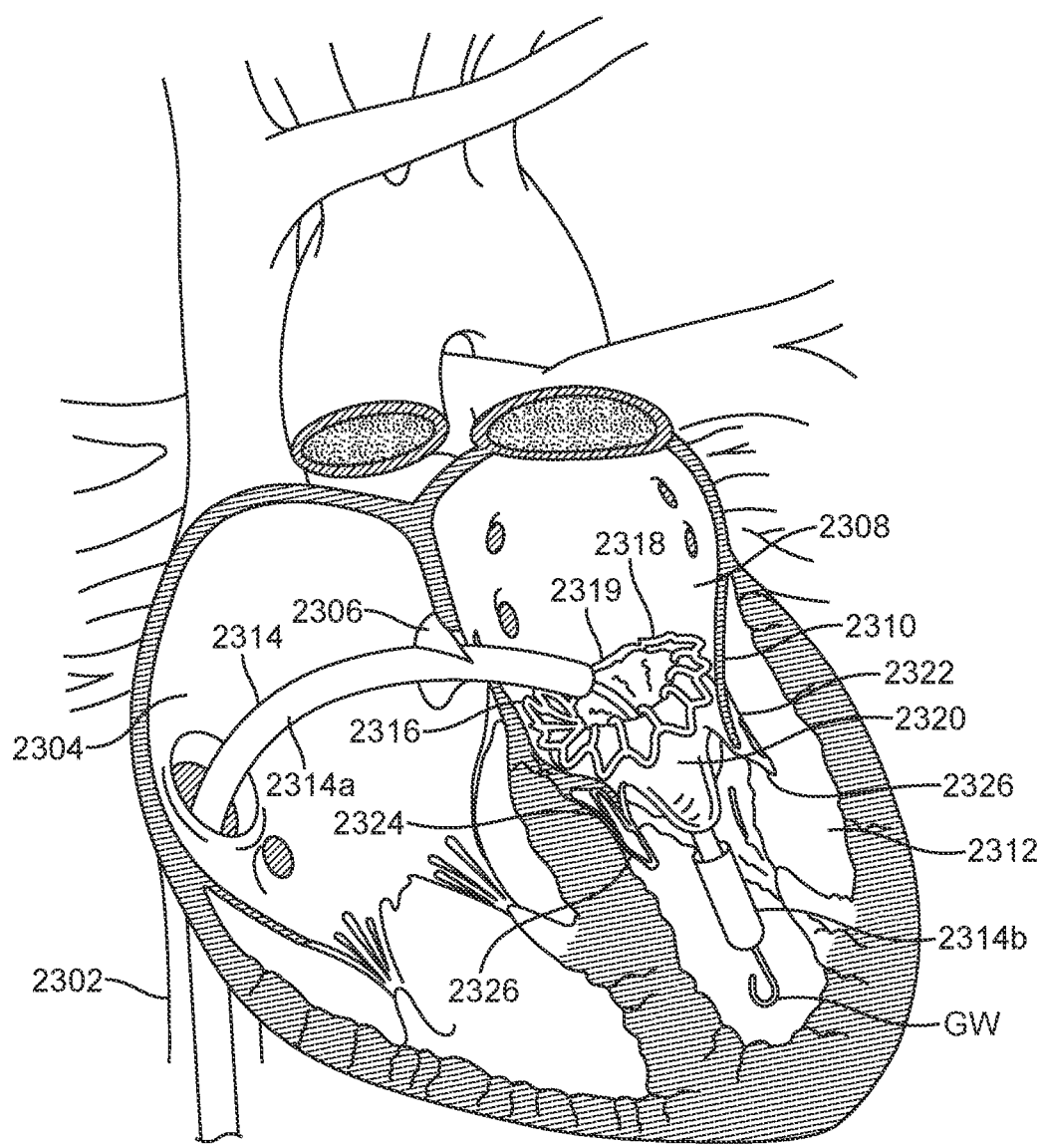
Figure 23G:
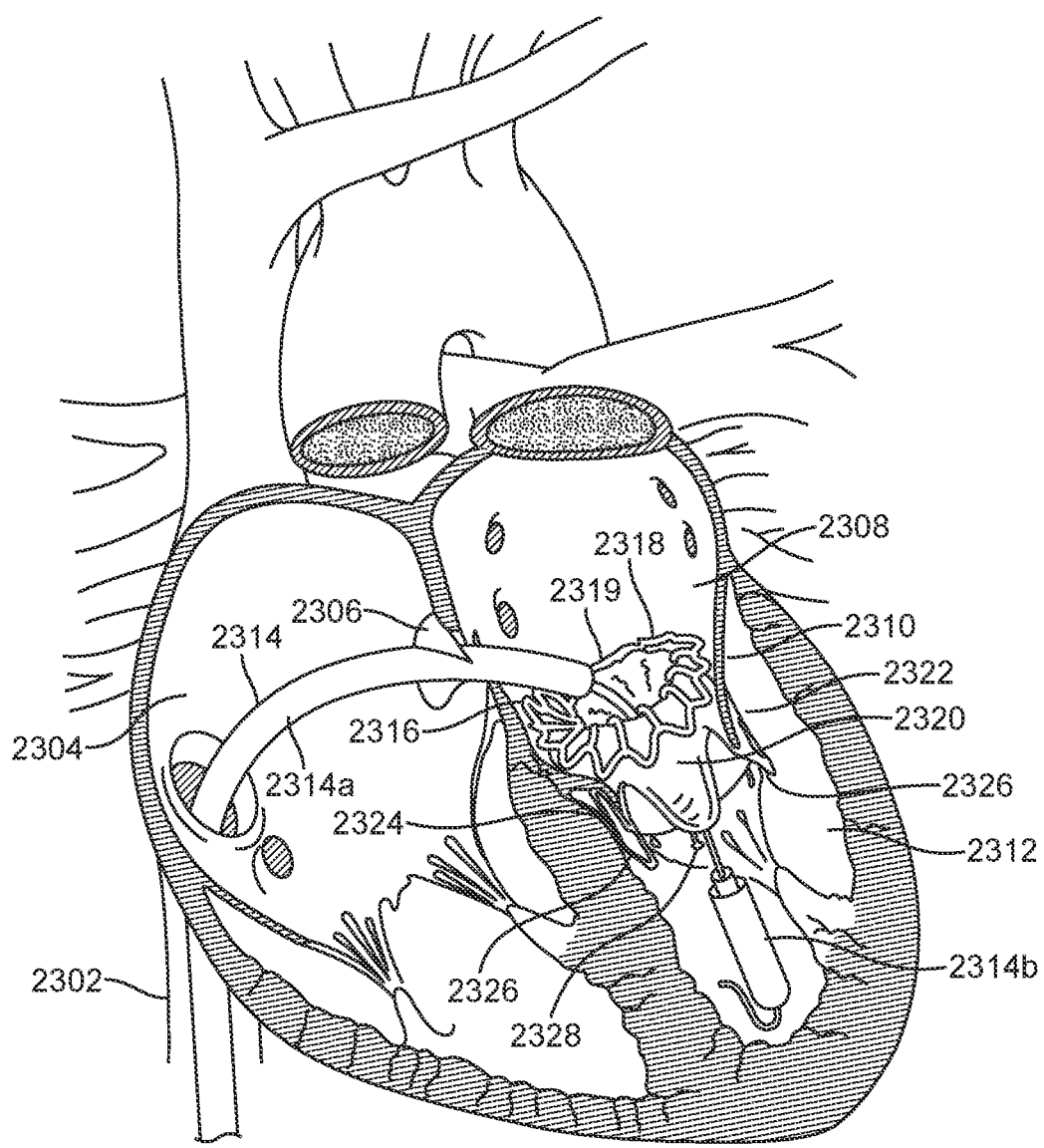

FIG. 23F shows that further distal advancement of distal portion 2314b releases the ventricular trigonal tabs and the posterior tab and the ventricular skirt 2326 is also released and allowed to radially expand outward against the native mitral valve leaflets without engaging the ventricular wall. This creates a sealing funnel within the native leaflets and helps funnel blood flow through the prosthetic valve. With the commissures of the prosthetic valve still captured by the delivery system, very minor adjustments may still be made to ensure accurate positioning, anchoring and sealing. The prosthetic valve is now anchored in four positions. The anchor tabs 2328 are then released from the delivery device by further advancement of an inner shaft, allowing the tabs to self-expand out of slots on the delivery catheter as previously discussed above and shown in FIG. 23G. The prosthetic valve is now implanted in the patient's heart and takes over the native mitral valve. The delivery device 2314 may then be removed from the heart by proximally retracting it back through the atrial septum, and out of the vena cava.

Figure 24:
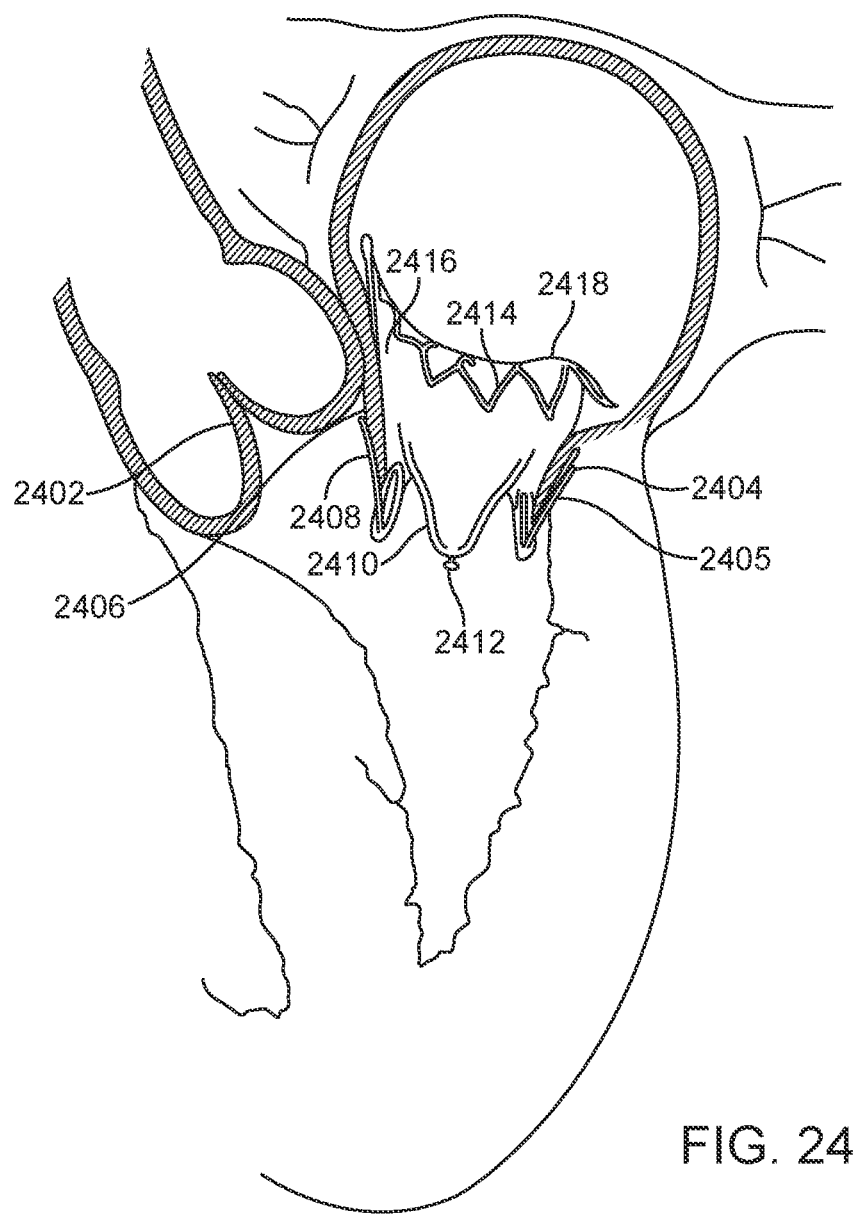
FIG. 24 illustrates a prosthetic mitral valve implanted in the mitral space.

FIG. 24 shows the prosthetic valve 2418 anchored in the mitral space after transapical or transseptal delivery. Prosthetic valve 2418 is preferably the prosthetic mitral valve illustrated in FIG. 8A, and delivered by methods shown in FIGS. 22A-22G or FIGS. 23A-23G. The prosthetic valve 2418 has radially self-expanded into engagement with the mitral valve to anchor it in position without obstructing other portions of the heart including the left ventricular outflow tract such as aortic valve 2402. The anterior trigonal tabs 2408 (only 1 seen in this view) and the posterior ventricular tab 2405 are radially expanded outward from the rest of the ventricular skirt 2410 and the anterior leaflet 2406 and posterior leaflet 2404 are captured between the respective tab and the ventricular skirt 2410 to form an anchor point. The ventricular skirt 2410 is also radially expanded outward to engage and press outwardly at least some of the chordae tendineae and papillary muscles but preferably without pressing against the ventricular wall. The annular region 2416 is expanded radially outward to engage and press against the mitral valve annulus, and the atrial skirt 2414 has also expanded outwardly to form a flange that rests on top of the mitral valve against the atrium. Thus, the prosthetic valve 2418 is anchored in four positions in the mitral space which prevents the prosthetic valve from migrating or dislodging during contraction of the heart. Moreover, using four anchor points lessens the anchoring pressure that is required to be applied in any given anchoring zone as compared to a prosthesis that is anchored in only a single anchoring zone, or in any combination of these four anchoring zones. The consequent reduction in radial force required to be exerted against the native structures in each zone minimizes the risk of obstruction or impingement of the nearby aortic valve or aortic root caused by the displacement of the native mitral valve apparatus. Valve leaflets 2420 form a tricuspid valve which opens with antegrade blood flow and closes with retrograde blood flow. Tab 2412 on a tip of the commissures 2421 (best seen in FIG. 25) remains free after disengagement from the delivery device.

Figure 25:
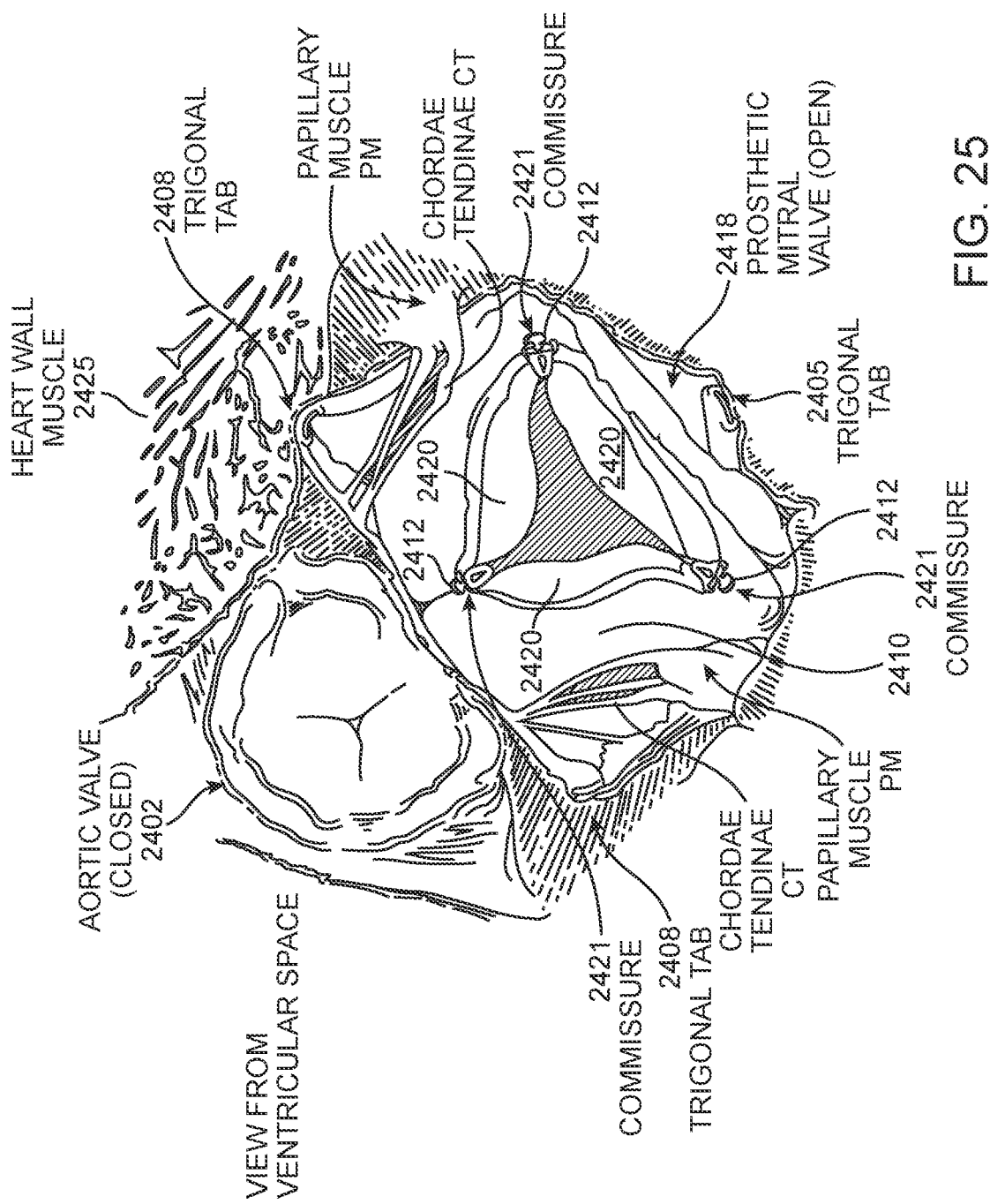
FIG. 25 illustrates a bottom view of a mitral valve implanted in the mitral space looking upward from the left ventricle.

FIG. 25 illustrates the prosthetic valve 2418 of FIG. 24 anchored in the mitral space and viewed from the left ventricle, looking upward toward the atrium. As previously mentioned, the prosthetic valve 2418 may be transapically or transseptally delivered and is preferably the prosthetic mitral valve illustrated in FIG. 8A, delivered by methods shown in FIGS. 22A-22G or FIGS. 23A-23G. This view more clearly illustrates anchoring and engagement of the prosthetic mitral valve 2418 with the adjacent tissue. For example, the three valve leaflets 2420 forming the tricuspid valve are shown in the open position, allowing blood flow therepast. Additionally, the anterior trigonal tabs 2408 and the posterior ventricular tab 2405 are shown radially expanded outward into engagement with the ventricular heart tissue 2425. The anterior portion of the prosthetic valve in between anterior trigonal tabs 2408 is approximately flat to match the corresponding flat anatomy as previously discussed above. The flat shape of the anterior portion of the prosthetic valve prevents the prosthetic valve from impinging on and obstructing adjacent anatomy such as the left ventricular outflow tract including the aortic valve. FIG. 25 also illustrates how the ventricular skirt 2410 expands radially outward against the native mitral valve leaflets.

Drug Delivery

Any of the prosthetic valves may also be used as a drug delivery device for localized drug elution. The therapeutic agent may be a coated on the prosthetic valve, on the tissue covering the anchor, on both, or otherwise carried by the prosthetic valve and controllably eluted therefrom after implantation. Examples of drugs include anti-calcification drugs, antibiotics, anti-platelet aggregation drugs, anti-inflammatory drugs, drugs which inhibit tissue rejection, anti-restenosis drugs, anti-thrombogenic drugs, thrombolytic drugs, etc. Drugs which have these therapeutic effects are well known to those of skill in the art.

Flow Control

Figure 26A:
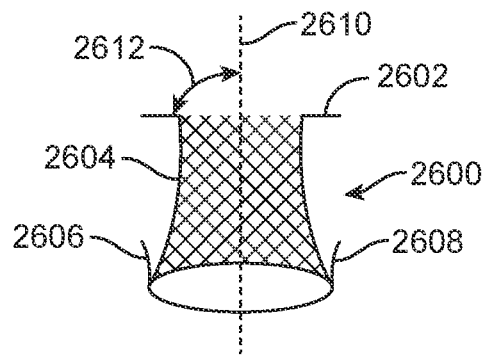
FIGS. 26A-26C illustrate examples of prosthetic valves where the outflow orifice is directed in a desired direction.
Figure 26B:
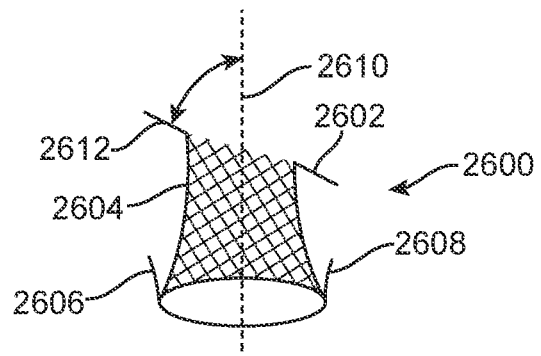
Figure 26C:
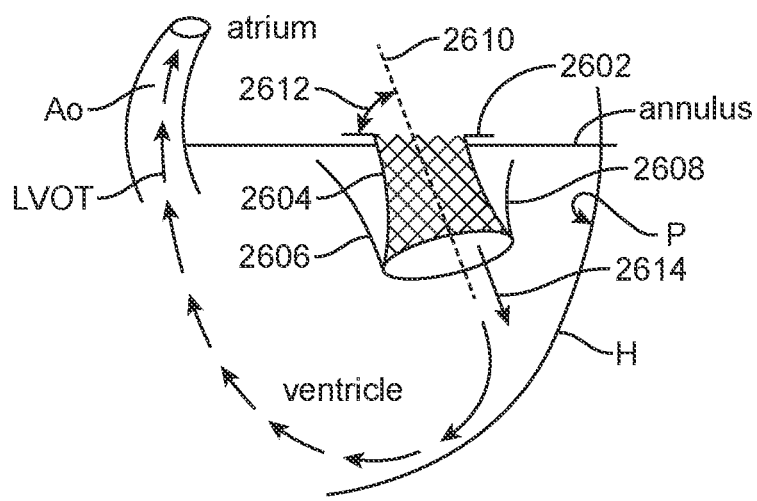

FIGS. 26A-26C illustrate how orientation of the prosthetic valve can be used to control fluid outflow patterns.

In FIG. 26A, a prosthetic valve 2600 which may be any of the prosthetic valves disclosed in this specification and which may be implanted using any of the disclosed methods and delivery systems herein, includes an expandable frame having an atrial flange 2602, a ventricular skirt, an annular region 2604, and anterior (only one visible in this view) and posterior anchor tabs 2606, 2608. The atrial flange forms an angle 2612 that is substantially perpendicular with the longitudinal axis 2610 of the prosthetic valve. The flange angle may be formed by heat treating the struts in the prosthetic valve during manufacturing. The longitudinal axis of the prosthetic valve is also substantially parallel to the fluid flow path though the prosthetic valve and out of outflow orifice of the prosthetic valve. Thus, the atrial flange lies substantially flush and parallel to the plane of the native valve and the flow path is substantially perpendicular thereto, which means the blood flow path is substantially parallel with the longitudinal axis of the prosthetic valve. Blood exiting straight out and downward from the prosthetic valve outflow orifice may be different than the natural anatomic blood flow path which can vary from patient to patient. The natural blood flow path in healthy heart is for blood to flow toward the posterior wall of the heart, down the posterior wall toward the apex of the heart, around the apex of the heart, and then upward toward the LVOT and out the aorta via the aortic valve, and thus the configuration in FIG. 26A may create unnatural blood flow dynamics for some patients.

In FIG. 26B, the atrial flange 2602 has been angled relative to the longitudinal axis of the prosthetic valve such that the anterior portion of the atrial flange is angled radially outward in an upward sloping direction and sloped downward radially inward toward the longitudinal axis while the posterior atrial flange is angled downward in a radially outward direction and away from the longitudinal axis to form a flange that is ramped or sloped upward in the anterior direction and sloped downward in the posterior direction. Angling the atrial flange allows positioning of the prosthetic valve to direct the outflow of the prosthetic valve in a desired direction. The angle of the posterior portion of the flange relative to the longitudinal axis of the prosthetic valve may be the same as the angle of the anterior portion of the flange relative to the longitudinal axis. The angle of the atrial flange may be formed by heat treating the struts in the prosthetic valve during manufacturing prior to implantation, and the prosthetic valve may be any of the prosthetic valves disclosed herein. In addition to the angle of the atrial flange 2602 shown in FIG. 26A, other aspects of the atrial flange may generally take the same form as any other atrial flange described herein. For example, the atrial flange may have a D-shape to conform to the native anatomy. In other examples, the atrial flange may be angled differently, for example instead of the flange sloping upward in the posterior to anterior direction, the flange may slope downward in the posterior to anterior direction. Or the posterior portion of the flange may be disposed at a different angle than the anterior angle. In any example, the struts that form the atrial flange will lie in flat linear configuration that is substantially parallel with the longitudinal axis of the prosthetic valve when the atrial flange is in the collapsed configuration such as when the atrial flange is constrained by being disposed in a lumen in an outer shaft during delivery. When the constraint is removed from the atrial flange by retraction of the outer shaft, the atrial flange may self-expand.

FIG. 26C shows the prosthetic valve 2600 of FIG. 26B implanted in a patient's mitral valve. When the atrial flange 2602 is anchored, it sits flush against the atrial floor to form a non-perpendicular angle 2612 between the plane of the native valve and the longitudinal axis of the prosthetic valve. This results in the outflow orifice pointing posteriorly such that blood flow 2614 is directed toward the posterior P wall of the heart H. The inflow and outflow axes are transverse to the longitudinal axis of the native valve. Flow is still substantially parallel with the longitudinal axis of the prosthetic valve. The blood then flows downward along the posterior wall towards the apex of the heart, curves around the apex of the heart and upward into the left ventricular outflow tract LVOT into the aorta, Ao. This is believed to be a more physiologically normal blood flow pattern in a healthy heart for some patients and thus less disruptive to blood circulation. It helps preserve flow momentum and conserves flow energy allowing the heart to function more efficiently. The anchor tabs 2606 and 2608 can anchor on the fibrous trigones/posterior annulus as previously described in this specification. Other aspects of the prosthetic valve may take the form of any of the other prosthetic valves disclosed herein, such as having a D-shape, anterior and posterior anchors, ventricular skirt, etc.

Figure 27:
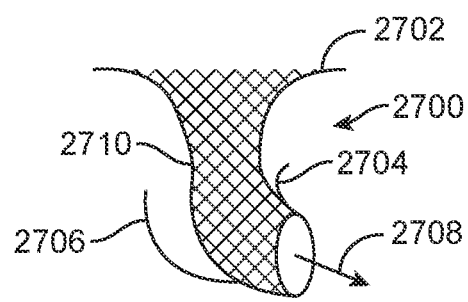
FIG. 27 shows another example of a prosthetic valve where the outflow orifice is directed in a desired direction.

FIG. 27 illustrates another example of a prosthetic valve which can be used to direct fluid flow in a desired direction. Prosthetic valve 2700 may be any of the prosthetic valves disclosed herein, and may have an atrial flange 2702, anterior and posterior anchor tabs 2706, 2704 but the expandable frame 2710 may be shaped so that the outflow 2708 is directed in a desired direction such as the posterior wall of the patient's heart to provide more natural blood flow. Thus, the exit orifice of the prosthetic valve may be tilted relative to the longitudinal axis of the prosthetic valve. The prosthetic valve 2700 may be shaped to direct the flow to any desired location, here the outflow end is angled relative to the longitudinal axis of the prosthetic valve so that flow is directed toward the posterior wall of the ventricle to facilitate flow down the posterior wall of the ventricle toward the apex of the heart, around the apex of the heart and then upward toward the LVOT and out the aorta via the aortic valve. The atrial flange may be any of the atrial flanges disclosed herein but here, the atrial flange may be D-shaped and lie in a flat plane that is substantially orthogonal to the longitudinal axis of the prosthetic valve, and the atrial flange also will lie in a plane that is parallel to the plane of the native valve annulus. The valve may also include anterior anchor tabs, posterior anchor tabs, an annular region and a ventricular skirt such as those disclosed herein. The inflow axis of the prosthetic valve is substantially parallel with the longitudinal axis of the prosthetic valve.

Figure 28:
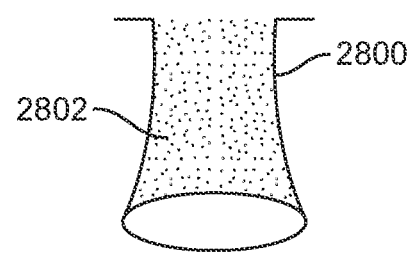
FIG. 28 shows a covered prosthesis.

FIG. 28 shows a prosthetic valve 2800 which may be any of the prosthetic valves disclosed herein including a prosthetic mitral valve, and any of the features of the prosthetic valves disclosed herein may be included in the example of FIG. 28 such as the atrial flange, annular region, ventricular region, anterior and posterior anchor tabs, etc. The expandable frame of the prosthetic valve may be covered with a fabric, tissue or any other material 2802 as previously discussed. However, instead of coupling the cover with sutures to the frame, the cover may be welded to the expandable frame. Thus, by eliminating the sutures, the prosthetic valve will have a smaller profile in the collapsed configuration thereby facilitating delivery to the target treatment valve. Similarly, the prosthetic valve leaflets may be coupled to the expandable frame and commissure posts without sutures (not illustrated) to further help reduce profile of the collapsed device during delivery. All of the expandable frame or only selection portions may be coupled to the cover. For example, some or all of the atrial flange, annular region, ventricular skirt, anchor tabs, etc. may be covered or uncovered with the covering material. Additionally, combinations of suture or sutureless connections between the cover and the prosthetic valve frame may be used to join the materials together.

Figure 29A:
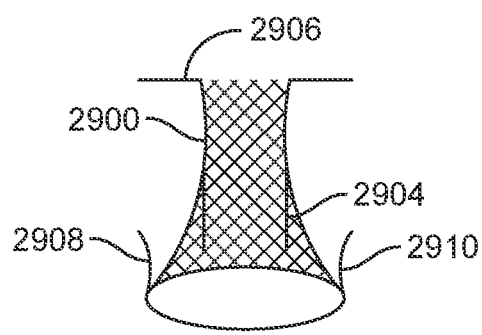
FIGS. 29A-29B show open and closed commissure posts on a prosthetic valve.
Figure 29B:
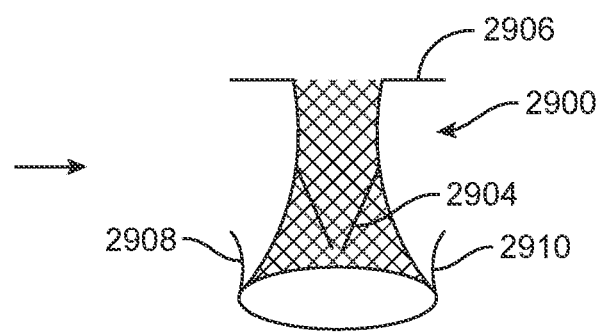

FIGS. 29A-29B illustrate optional positioning of the commissure posts in any of the prosthetic valve examples disclosed herein. In FIG. 29A the prosthetic valve 2900 may be a prosthetic mitral valve including the same structure as other examples disclosed herein such as an atrial flange 2906, anterior anchor tabs 2908, and a posterior anchor 2910. The commissure posts (only two shown in this view but may include more or less) 2904 are coupled at one end to the expandable frame and extend downstream and substantially parallel with the longitudinal axis of the prosthetic valve when the prosthetic valve mechanism is in the open position. Tissue, fabric or other material is typically coupled to the expandable frame and the commissure posts to form a bicuspid, tricuspid or other number of prosthetic valve leaflets in the prosthetic valve mechanism. The prosthetic leaflets are not illustrated for ease in viewing the commissure posts.

In FIG. 29B, the commissure posts 2904 are disposed closer to one another and engage or nearly engage one another when the valve is in the closed position to prevent regurgitation through the valve mechanism. In this example, different size prosthetic valves may have different size valve orifices. It may be desirable to provide prosthetic valves with a uniform outflow orifice size as seen in FIGS. 30A-30B.

Figure 30A:
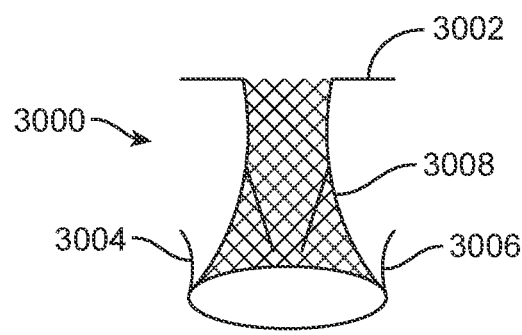
FIGS. 30A-30B show open and closed commissure posts on a prosthetic valve.
Figure 30B:
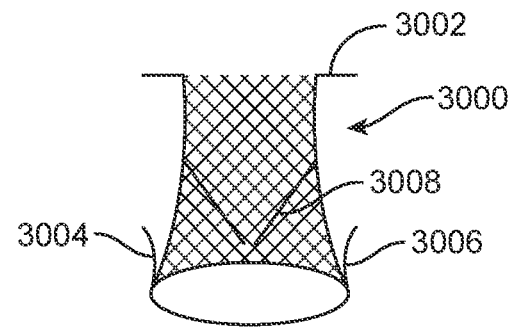

FIGS. 30A-30B show an example of a prosthetic valve 3000 which may have a consistent outflow orifice size even for different valve sizes. Also the orifice size is smaller than if the commissure posts were straight as seen in FIG. 29A. In FIG. 30A, the prosthetic valve 3000 may be similar to any of the prosthetic valves disclosed in this specification such as including an expandable frame having an atrial flange 3002, anterior anchors 3004 and a posterior anchor 3006. The commissure posts (only two shown but may be more or less) 3008 are angled radially inward toward the center of the prosthetic valve to form a consistent outflow orifice size (e.g. diameter). FIG. 30A shows the commissure posts in the open configuration where the commissure posts and hence prosthetic valve leaflets connected thereto (not shown for convenience) are angled toward one another but do not touch and the orifice is open. A consistent size opening may be used in different prosthetic valve sizes designed to be implanted into different native valve sizes. In FIG. 30B the prosthetic valve mechanism is closed with the commissure posts 3008 disposed against one another to close the orifice. Commissure post angle may be established by heat treating during manufacturing.

Figure 31B:
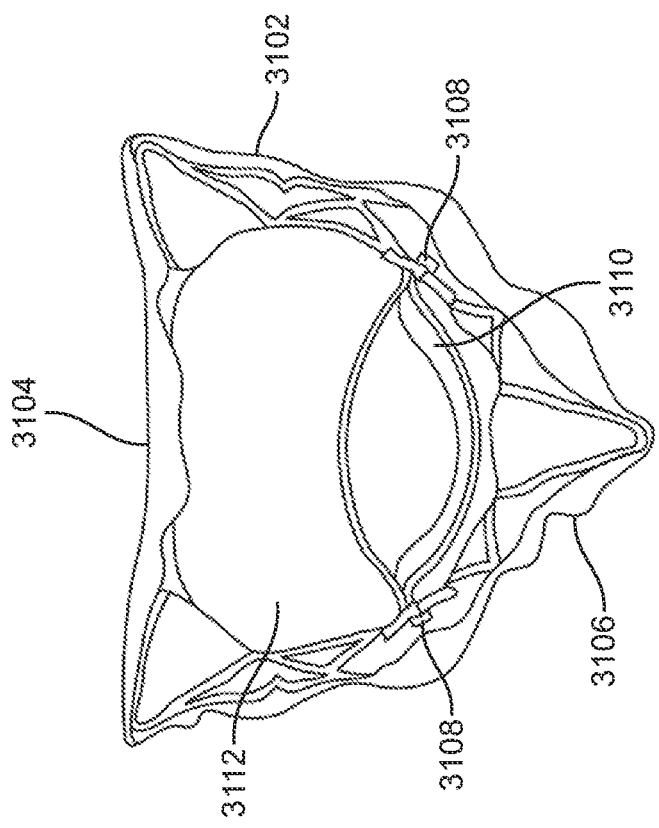
FIGS. 31A-31B illustrate an example of a prosthetic valve with leaflets that direct blood flow in a posterior direction.
Figure 31A:
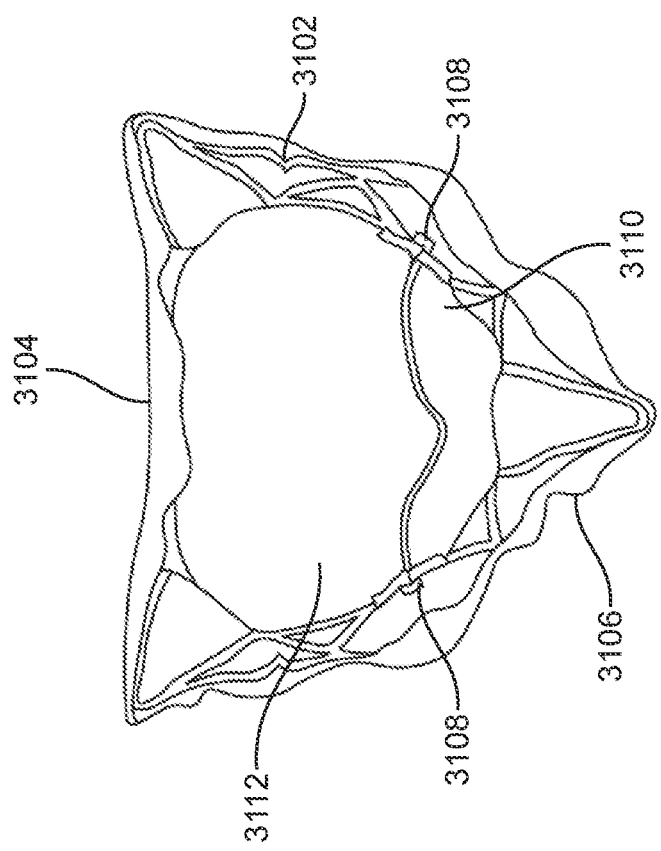

FIGS. 31A-31B show another example of a prosthetic valve 3102 which may have the radially expandable frame of any of the prosthetic valve frames described herein. The frame generally takes the same form as any of the frames disclosed herein including optionally having an atrial flange, annular region, ventricular skirt, anterior, and posterior anchor tabs as well as a covering. The frame may be D-shaped with a flat anterior side 3104 and a partially cylindrically shaped posterior side 3106. In this example the prosthetic leaflets are used to direct flow to a desired location in the heart rather than the overall shape of the expandable frame controlling flow direction, such as seen in FIG. 27 above. Here, the prosthetic valve mechanism includes two prosthetic valve leaflets, a wide anterior leaflet 3112 and a smaller posterior leaflet 3110. The leaflets are coupled to two commissure posts 3108 that generally take the same form as previously described commissure posts. The wide anterior prosthetic leaflet 3112 may be wide enough to span the width of the native fibrous trigones in a native mitral valve and long enough so that the prosthetic leaflet may be coupled to the commissure tabs such that the inflow edge of the prosthetic leaflet is more anteriorly disposed than the outflow edge of the prosthetic leaflet. The outflow edge of the anterior prosthetic leaflet is disposed more posteriorly. This creates an angled prosthetic valve leaflet that is angled relative to the longitudinal axis of the prosthetic valve anchoring frame and thus as blood passes through the prosthetic valve, the blood is directed toward the posterior wall of the patient's heart to create the more natural blood flow discussed above. The posterior leaflet is smaller in length and width relative to the anterior leaflet and is designed to appose with the anterior leaflet to open and close to create a one-way valve that prevents regurgitation. FIG. 31A shows the two prosthetic leaflets 3110, 3112 apposed in a closed position. Also in this example as well as any other example, some of the prosthetic valve leaflets may be mobile, meaning they move while other prosthetic valve leaflets may be immobile, meaning they remain stationary. For example, one prosthetic leaflet may be mobile while a second prosthetic leaflet may be immobile.

FIG. 31B shows the prosthetic valve 3102 of FIG. 31A in the open position with the edges of the prosthetic valve leaflets unapposed. The outflow edge of the posterior leaflet extends downward away from the expandable frame while the anterior leaflet sweeps downward from the anterior to posterior part of the expandable frame to form the angled prosthetic leaflet for directing flow posteriorly. Additionally, the anterior leaflet may also form an arcuate shape with a concave portion facing radially inward.

FIGS. 26B-26C, 27, and 31A-31B show that a prosthetic valve may have means for anchoring the prosthetic valve to the native anatomy such as a radially expandable frame, as well as means for forming a one way valve that directs blood flow to a desired direction such as toward the posterior wall of the patient's native mitral valve in order to provide a more natural blood flow that maintains momentum of the blood flow and the energy of the blood as it flows through the prosthetic valve, though the left ventricle and out the left ventricular outflow tract of the patient's aorta allowing the heart to function more efficiently. The means for directing flow may be accomplished by features designed into the expandable frame or other means for anchoring, or the flow directing means may be accomplished with a prosthetic valve mechanism.

Figure 32A:
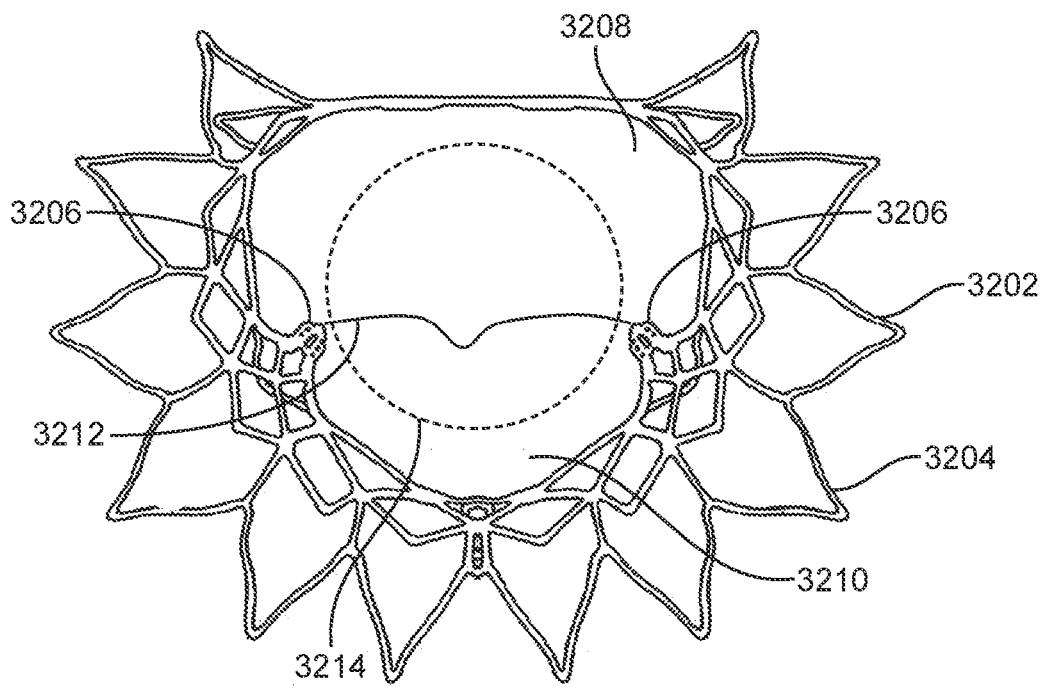
FIG. 32A shows an example of effective orifice area in a prosthetic valve.

FIG. 32A shows a prosthetic valve 3202 with an effective orifice area (EOA) 3214. The prosthetic valve 3202 may be any of the prosthetic valves disclosed herein and includes, for example an atrial flange 3204, and two commissure posts 3206. The prosthetic valve mechanism has two prosthetic leaflets including an anterior leaflet 3208 and a posterior leaflet 3210 coupled to commissure posts 3206. The outflow edges of the prosthetic leaflets appose one another to close the valve along line 3212. In this example, the prosthetic leaflets are sized, shaped and coupled to the expandable frame such that the effective orifice area 3214 is substantially circular and centered in the D-shaped prosthetic valve frame. Therefore, the effective orifice area may be centered and may be substantially concentric with the longitudinal axis of the prosthetic valve.

Figure 32B:
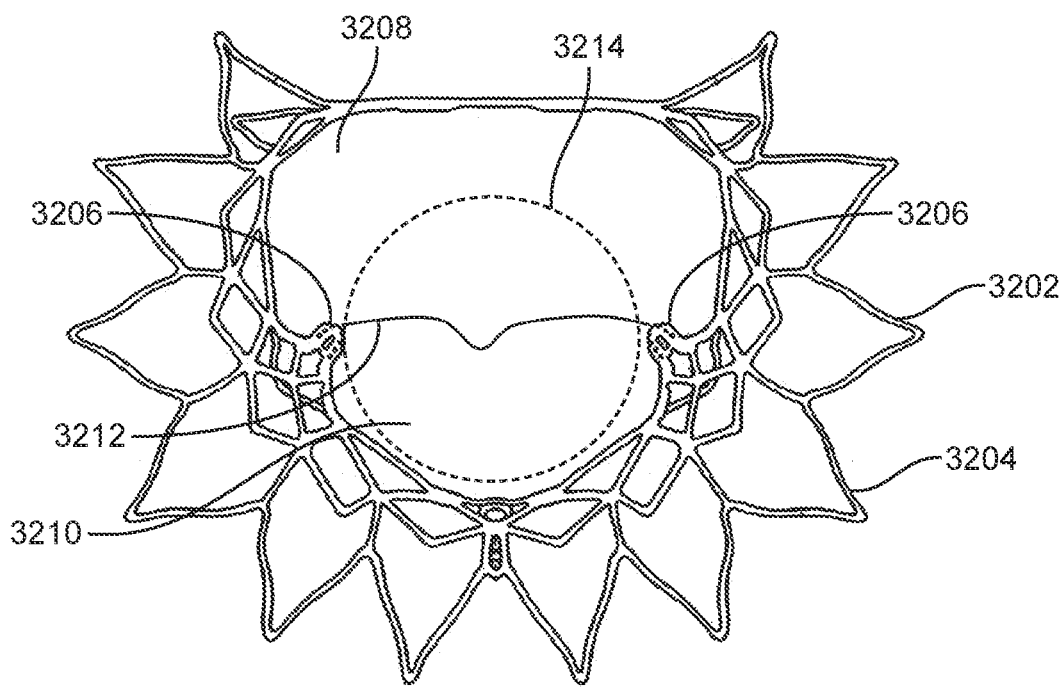
FIG. 32B shows another example of effective orifice area that has been offset in a prosthetic valve.

FIG. 32B shows another example of a prosthetic valve 3202 that is similar to the valve in FIG. 32A with the major difference being that the effective orifice area 3214 has been offset toward the lower six o'clock posterior portion of the prosthetic valve. This is accomplished by attaching the prosthetic valve leaflets to the commissure posts and expandable frame to create the anterior leaflet described in FIGS. 31A-31B in order to direct blood flow in a posterior direction. Other aspects of valve 3202 are generally the same as in FIG. 32A including the D-shaped expandable frame.

In another example, the effective orifice area may be offset posteriorly while still maintaining flow substantially parallel to the longitudinal axis as described in greater detail below.

Figure 33A:
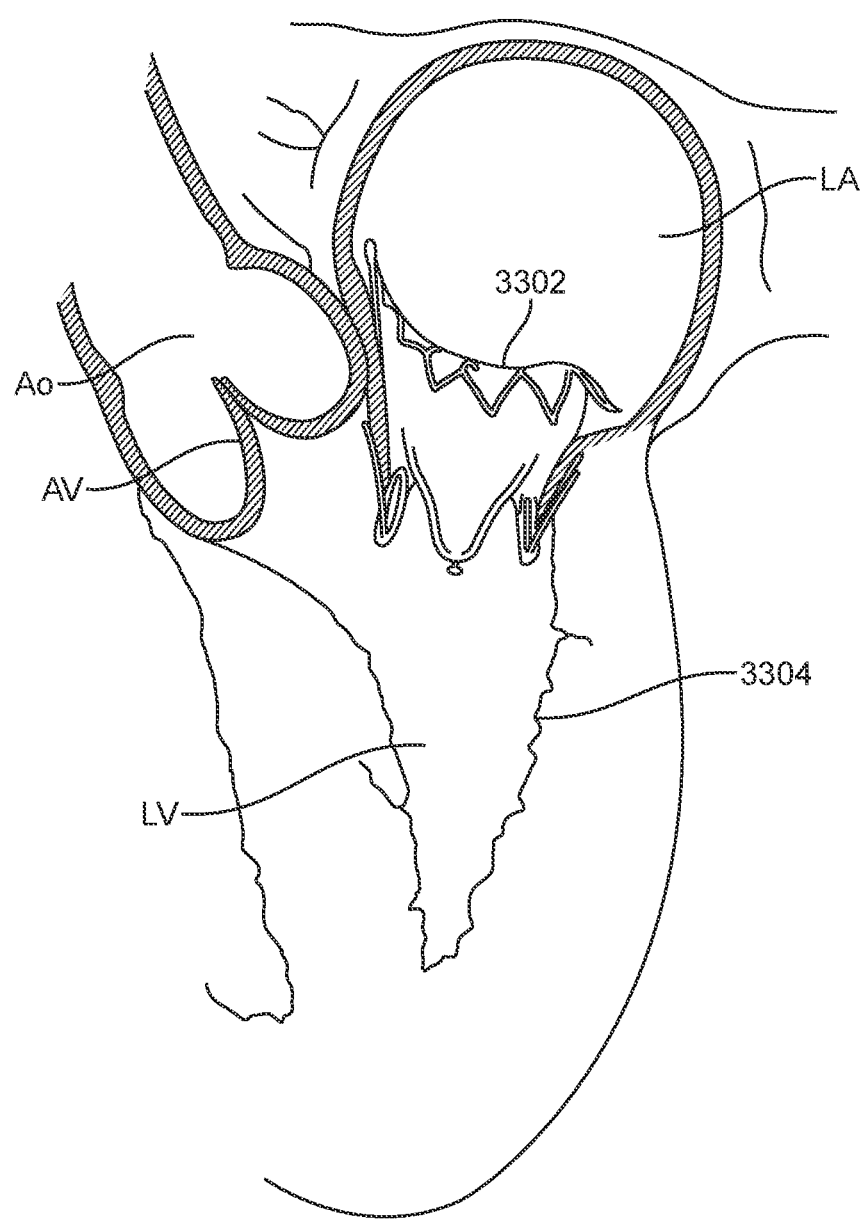
FIG. 33A shows a prosthetic valve implanted in a native mitral valve.

FIG. 33A shows a prosthetic mitral valve 3302 implanted in a native mitral valve to control blood flow from the left atrium to the left ventricle LV. The posterior wall 3304 of the left ventricle is also illustrated along with other basic anatomy such as the aortic valve AV and the aorta Ao. The prosthetic valve 3302 may be any of the prosthetic valves disclosed herein.

Figure 33B:
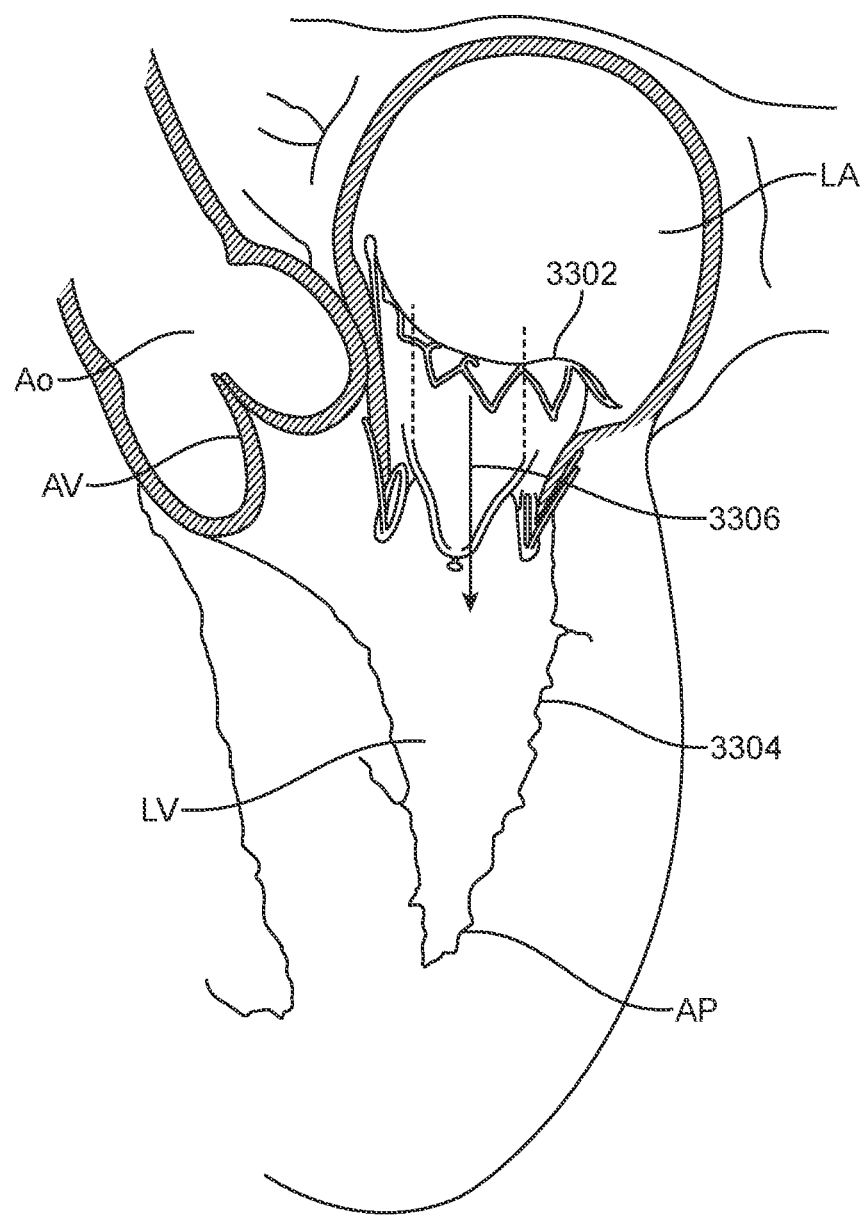
FIGS. 33B-33D show possible flow patterns through the valve of FIG. 33A.

FIG. 33B illustrates a standard prosthetic valve such as seen in FIG. 26A or any other example disclosed herein that does not have means for directing the flow to a desired region of the heart to maintain a more natural blood flow. Without directing the blood flow, the blood flow will generally follow a path 3306 that is parallel to the longitudinal axis of the prosthetic valve and this results in blood flow being directed toward the apex AP of the heart which may not be an optimal flow pattern causing flow to lose momentum and lose energy.

Figure 33C:
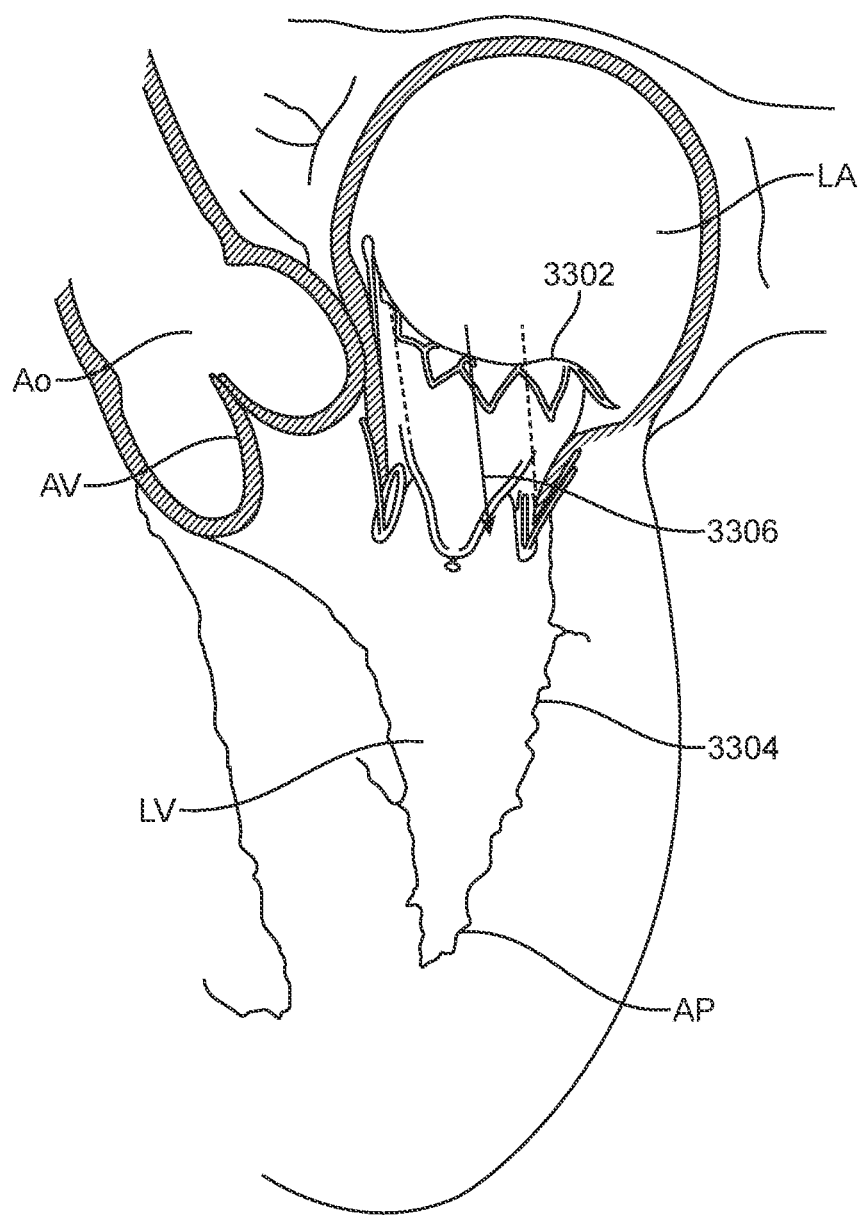

FIG. 33C illustrates using means for directing blood flow in the prosthetic valve to obtain a more natural flow. Here, the prosthetic valve 3302 may be any of the prosthetic valves having means for directing blood flow to a desired location, such as the examples in FIGS. 26B-26C, 27, and 31A-31B. Therefore, as flow passes through the prosthetic valve 3302, flow 3306 is directed to a posterior wall 3304 of the patient's heart and then the blood flows downward along the posterior wall toward the apex AP of the heart, around the apex and upwards into the left ventricular outflow tract of the aorta via the aortic valve AV. Without being bound by any theory this flow pattern is believed to match the natural blood flow more closely and therefore provide more physiologically accurate flow including preserving blood flow momentum and maintaining energy which allow the heart to function more efficiently. Thus, the blood flow is generally transverse to the longitudinal axis of the prosthetic valve.

Figure 33D:
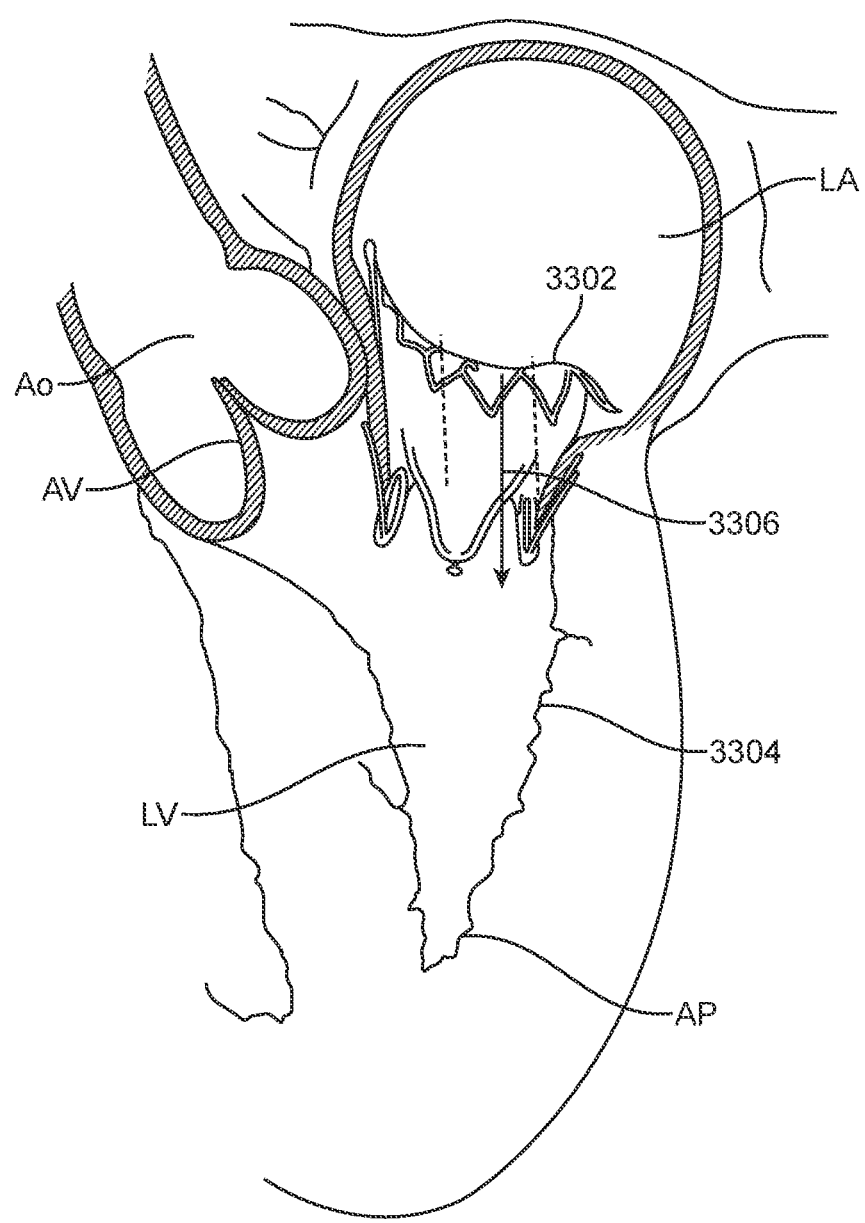

FIG. 33D shows another example of a prosthetic valve which may be any of those disclosed herein and where the effective orifice area may be offset posteriorly away from the prosthetic valve center (either centralized or distributed radially along the entire posterior wall based on prosthetic leaflet design, coaptation, number of leaflets, etc.) while still maintaining flow substantially parallel to the longitudinal axis of the prosthetic valve. Here the effective orifice area is simply moved so that it is offset from the center of the prosthetic valve and moved posteriorly by adjusting the size, shape and attachment of the prosthetic leaflets to the anchor frame. Thus, blood flow 3306 will still be substantially parallel to the longitudinal axis of the prosthetic valve but blood flow 3306 will also simultaneously be directed toward the posterior wall of the ventricle but the center of the flow is offset and non-concentric with the longitudinal axis of the prosthetic valve. Other aspects of FIG. 33D are generally the same as in FIGS. 33A-33C.

NOTES AND EXAMPLES

The following, non-limiting examples, detail certain aspects of the present subject matter to solve the challenges and provide the benefits discussed herein, among others.

While the present disclosure focuses on the use of a prosthetic valve for treating mitral regurgitation, this is not intended to be limiting. The prosthetic valves disclosed herein may also be used to treat other body valves including other heart valves or venous valves. Examples of heart valves include the aortic valve, the tricuspid valve, or the pulmonary valve.

Example 1 is a prosthetic valve configured to be disposed in a native valve of a patient, the valve lying in an anatomic plane, said valve comprising: a radially expandable frame having an expanded configuration and a collapsed configuration, the expanded configuration configured to engage tissue in the native valve, the collapsed configuration configured for delivery to the native valve, and the frame further comprising a first end, a second end opposite the first end, an atrial flange adjacent the first end, a ventricular skirt adjacent the second end, a longitudinal axis extending between the first and second ends, an annular region disposed between the atrial flange and the ventricular skirt, and a prosthetic valve mechanism having an outflow orifice adjacent the second end, wherein the outflow orifice has fluid flow axis extending therethrough that is disposed at an angle relative to the longitudinal axis, or wherein the atrial skirt lies in a plane that is transverse to the longitudinal axis.

Example 2 is the prosthetic valve of Example 1, wherein the fluid flow axis is non-parallel with the longitudinal axis.

Example 3 is the prosthetic valve of any of Examples 1-2, wherein the fluid flow axis is transverse to the longitudinal axis.

Example 4 is the prosthetic valve of any of Examples 1-3, wherein the atrial flange plane is non-parallel with the anatomic plane.

Example 5 is the prosthetic valve of any of Examples 1-4, wherein the atrial flange plane is transverse to the anatomic plane.

Example 6 is the prosthetic valve of any of Examples 1-5, wherein the atrial flange plane is transverse to the longitudinal axis.

Example 7 is the prosthetic valve of any of Examples 1-6, wherein the outflow orifice is angled to direct fluid flow passing therethrough toward a posterior portion of the patient's heart.

Example 8 is the prosthetic valve of any of Examples 1-7, wherein the outflow orifice directs fluid exiting the outflow orifice downstream along a posterior wall of the patient's heart, around an apex of the patient's heart and out a left ventricular outflow tract of the patient's heart.

Example 9 is the prosthetic valve of any of Examples 1-8, wherein the fluid flow axis is tilted toward a posterior portion of the patient's heart.

Example 10 is the prosthetic valve of any of Examples 1-9, wherein the outflow orifice faces a posterior portion of the patient's heart.

Example 11 is the prosthetic valve of any of Examples 1-10, wherein the prosthetic valve mechanism comprises a plurality of prosthetic valve leaflets coupled to the radially expandable frame, wherein at least one of the plurality of prosthetic valve leaflets has an upstream edge and a downstream edge, wherein the upstream edge is disposed more anteriorly relative to the downstream edge, the downstream edge disposed more posteriorly relative to the upstream edge thereby disposing the at least one of the plurality of prosthetic valve leaflets at an angle transverse to the longitudinal axis of the radially expandable frame that directs blood flow towards a posterior portion of the patient's heart.

Example 12 is the valve of any of Examples 1-11, wherein the plurality of prosthetic leaflets consist of two prosthetic valve leaflets.

Example 13 is a method for deploying a prosthetic valve in a heart of a patient, said method comprising: providing a prosthetic valve having a radially expandable frame with an atrial flange adjacent one end and a prosthetic valve mechanism having an outflow orifice adjacent a second end opposite the first end; radially expanding the frame into engagement with a native valve in the heart of the patient; and directing fluid flow through the prosthetic valve mechanism and out the outflow orifice toward a posterior portion of the patient's heart.

Example 14 is the method of Example 13, wherein directing the fluid flow comprises directing the fluid flow along a path transverse to a longitudinal axis of the prosthetic valve.

Example 15 is the method of any of Examples 13-14, wherein directing the fluid flow comprises directing the fluid flow along a path that is non-parallel to a longitudinal axis of the prosthetic valve.

Example 16 is a prosthetic valve configured to be disposed in a native valve of a patient, said valve comprising: a radially expandable frame having an expanded configuration to engage tissue in the native valve and a collapsed configuration for delivery to the native valve, the frame comprising a first end, a second end opposite the first end, an atrial flange adjacent the first end, a ventricular skirt adjacent the second end, an annular region disposed between the atrial flange and the ventricular skirt, and a prosthetic valve mechanism for controlling fluid flow therethrough.

Example 17 is the prosthetic valve of Example 16, further comprising a cover disposed over at least a portion of the frame, the cover welded thereto.

Example 18 is the prosthetic valve of any of Examples 16-17, wherein the cover is attached to the frame without sutures.

Example 19 is the prosthetic valve of any of Examples 16-18, wherein the cover comprises a fabric, tissue, a polymer, or combinations thereof.

Example 20, is the prosthetic valve of any of Examples 16-19, wherein the prosthetic valve mechanism comprises a plurality of prosthetic valve leaflets and a plurality of commissure posts having a free end and an opposite end coupled to the expandable frame, wherein the plurality of prosthetic valve leaflets are coupled to the plurality of commissure posts, and wherein the free ends of the plurality of commissure posts are angled radially inward to form an outflow orifice having a diameter less than a diameter of the ventricular skirt.

Example 21 is a method for treating a native valve in a patient's heart, said method comprising: providing a prosthetic valve having a radially expandable frame comprising a first end, a second end opposite the first end, an atrial flange adjacent the first end, a ventricular skirt adjacent the second end, an annular region disposed between the atrial flange and the ventricular skirt, and a prosthetic valve mechanism for controlling fluid flow therethrough; radially expanding the atrial flange into engagement with an atrial surface of the native valve; radially expanding the annular region and the ventricular skirt; and controlling fluid flow through the prosthetic valve mechanism with a plurality of prosthetic valve leaflets coupled to a plurality commissure posts coupled to the radially expandable frame.

Example 22 is the method of Example 21, further comprising crimping the prosthetic valve onto a delivery catheter, wherein the cover is coupled to the expandable frame with a sutureless method.

Example 23 is the method of any of Examples 21-22, wherein controlling the fluid flow comprises passing fluid through an outflow orifice in the prosthetic valve mechanism having a diameter less than a diameter of the ventricular skirt.

Example 24 is the method of any of Examples 21-23, wherein the plurality of commissure posts have a free end and an opposite end coupled to the expandable frame, and wherein the free ends of the plurality of commissure posts are angled radially inward to form the outflow orifice.

Example 25 is a prosthetic valve configured to be disposed in a native valve of a patient, the valve lying in an anatomic plane, said valve comprising: means for anchoring the prosthetic valve in the native valve of the patient; and means for controlling blood flow through the prosthetic valve, wherein the means for controlling the blood flow direct the blood flow toward a posterior wall of the patient's heart, down the posterior wall toward an apex of the patient's heart, and upward from the apex toward the aorta.

Example 26 is a prosthetic valve configured to be disposed in a native valve of a patient, the valve lying in an anatomic plane, said valve comprising: a radially expandable frame having an expanded configuration and a collapsed configuration, the expanded configuration configured to engage tissue in the native valve, the collapsed configuration configured for delivery to the native valve, and the frame further comprising a first end, a second end opposite the first end, an atrial flange adjacent the first end, a ventricular skirt adjacent the second end, a longitudinal axis extending between the first and second ends, an annular region disposed between the atrial flange and the ventricular skirt, and a prosthetic valve mechanism having an outflow orifice adjacent the second end, wherein the outflow orifice has an effective orifice area center that is radially offset from the longitudinal axis such that blood flowing through the prosthetic valve flows substantially parallel to the longitudinal axis and is directed toward a posterior wall of a ventricle of the patient's heart.

In Example 27, the apparatuses or methods of any one or any combination of Examples 1-26 can optionally be configured such that all elements or options recited are available to use or select from.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A prosthetic valve comprising:
   a radially expandable frame comprising:
     an annular region defining a longitudinal axis;
     an atrial flange extending from a first end of the annular region;
     a ventricular skirt extending from a second end of the annular region; and
     at least one anchor tab;
   a covering disposed along at least a portion of the annular region; and
   at least one leaflet disposed within the radially expandable frame, the at least one leaflet being angled relative to the longitudinal axis;
   wherein:
   the at least one leaflet comprises an anterior leaflet configured to direct blood flow therethrough toward a posterior wall of a heart of a patient;
   the at least one leaflet comprises a posterior leaflet that is shorter in length than the anterior leaflet;
   one of the posterior leaflet and anterior leaflet is immobile; and another of the posterior leaflet and anterior leaflet is mobile.

2. The prosthetic valve of claim 1, wherein the covering is disposed on the ventricular skirt.

3. The prosthetic valve of claim 1, wherein the covering is disposed on an exterior of the radially expandable frame.

4. The prosthetic valve of claim 1, wherein the at least one leaflet is made of a flexible material.

5. The prosthetic valve of claim 1, wherein:
   an inflow edge of the anterior leaflet is disposed more anteriorly than an outflow edge; and
   the outflow edge of the anterior leaflet is disposed more posteriorly than the inflow edge.

6. The prosthetic valve of claim 1, wherein the anterior leaflet is arcuate so as to form a concave portion facing radially inward relative to the longitudinal axis.

7. The prosthetic valve of claim 1, wherein the annular region is D-shaped.

8. The prosthetic valve of claim 1, wherein the posterior leaflet is smaller in width than the anterior leaflet.

9. The prosthetic valve of claim 1, wherein:
   an outflow edge of the posterior leaflet extends axially away from the radially expandable frame; and
   an outflow edge of the anterior leaflet extends at an angle from an anterior side of the radially expandable frame to a posterior side of the radially expandable frame.

10. The prosthetic valve of claim 1, wherein the at least one leaflet is coupled to a commissure post.

11. The prosthetic valve of claim 1, wherein the at least one leaflet is angled so as to be configured to direct blood flow toward a posterior wall of a heart into which the prosthetic valve is to be implanted.

12. The prosthetic valve of claim 1, wherein the at least one leaflet is offset toward a posterior side of device relative to the longitudinal axis.

13. A method for deploying a prosthetic valve in a heart of a patient, said method comprising:
   providing a prosthetic valve having a radially expandable frame with an annular region defining a longitudinal axis, an atrial flange adjacent a first end of the annular region, a prosthetic valve mechanism having an outflow orifice adjacent a second end of the annular region opposite the first end, a ventricular skirt adjacent the second end, at least one anchor tab and a covering disposed along at least a portion of the annular region;
   radially expanding the frame into engagement with a native valve in the heart of the patient; and
   directing fluid flow through the prosthetic valve mechanism and out the outflow orifice toward a posterior portion of the patient's heart via one or more leaflets disposed within the radially expandable frame;
   wherein:
   the one or more leaflets comprises an anterior leaflet configured to direct blood flow therethrough toward a posterior wall of a heart of a patient;

the one or more leaflets comprises a posterior leaflet that is shorter in length than the anterior leaflet;

one of the posterior leaflet and anterior leaflet is immobile; and another of the posterior leaflet and anterior leaflet is mobile.

14. The method of claim 13, wherein directing fluid flow through the prosthetic valve mechanism and out the outflow orifice toward a posterior portion of the patient's heart via one or more leaflets disposed within the radially expandable frame comprises:

curving the fluid flow with the one or more leaflets.

15. The method of claim 13, wherein directing fluid flow through the prosthetic valve mechanism and out the outflow orifice toward a posterior portion of the patients heart via one or more leaflets disposed within the radially expandable frame comprises:

moving at least one of the one or more leaflets.

16. The method of claim 13, wherein directing fluid flow through the prosthetic valve mechanism and out the outflow orifice toward a posterior portion of the patient's heart via one or more leaflets disposed within the radially expandable frame comprises:

directing fluid flow between the anterior leaflet and the posterior leaflet.

17. The method of claim 16, wherein:

the frame is D-shaped in cross-section when expanded; and the anterior leaflet and posterior leaflet form a circular cross-sectional area.

\* \* \* \* \*